US010370403B2

(12) United States Patent
Savage et al.

(10) Patent No.: US 10,370,403 B2
(45) Date of Patent: Aug. 6, 2019

(54) METHODS FOR THE SYNTHESIS OF CERAGENINS

(71) Applicants: Paul B. Savage, Mapleton, UT (US); Thomas E. Jacks, Hillsborough, NJ (US); Ross A. Miller, Fanwood, NJ (US); Andrew S. Thompson, Mountainside, NJ (US); Jared Lynn Randall, Smyrna, NY (US)

(72) Inventors: Paul B. Savage, Mapleton, UT (US); Thomas E. Jacks, Hillsborough, NJ (US); Ross A. Miller, Fanwood, NJ (US); Andrew S. Thompson, Mountainside, NJ (US); Jared Lynn Randall, Smyrna, NY (US)

(73) Assignee: Brigham Young University, Provo, UT (US)

( * ) Notice: Subject to any disclaimer, the term of this patent is extended or adjusted under 35 U.S.C. 154(b) by 6 days.

(21) Appl. No.: 15/135,969

(22) Filed: Apr. 22, 2016

(65) Prior Publication Data
US 2016/0311851 A1 Oct. 27, 2016

Related U.S. Application Data

(60) Provisional application No. 62/151,002, filed on Apr. 22, 2015, provisional application No. 62/165,006, filed on May 21, 2015, provisional application No. 62/191,922, filed on Jul. 13, 2015.

(51) Int. Cl.
*C07J 41/00* (2006.01)
*C07J 9/00* (2006.01)

(52) U.S. Cl.
CPC ............ *C07J 41/0088* (2013.01); *C07J 9/005* (2013.01); *C07J 41/0055* (2013.01); *C07J 41/0061* (2013.01)

(58) Field of Classification Search
CPC .... C07J 41/00; C07J 41/0088; C07J 41/0061; C07J 9/005; C07J 41/0055
See application file for complete search history.

(56) References Cited

U.S. PATENT DOCUMENTS

| 4,248,236 A | 2/1981 | Linder |
| 4,296,206 A | 10/1981 | Simons |
| 4,661,341 A | 4/1987 | Benedict et al. |
| 4,723,950 A | 2/1988 | Lee |
| 4,842,593 A | 6/1989 | Jordan et al. |
| 4,865,855 A | 9/1989 | Hansen et al. |
| 4,972,848 A | 11/1990 | Di Domenico |
| 5,025,754 A | 6/1991 | Plyler |
| 5,286,479 A | 2/1994 | Garlich et al. |
| 5,310,545 A | 5/1994 | Eisen |
| 5,356,630 A | 10/1994 | Laurencin et al. |
| 5,364,650 A | 11/1994 | Guthery |
| 5,380,839 A | 1/1995 | McCall et al. |
| 5,552,057 A | 9/1996 | Hughes et al. |
| 5,624,704 A | 4/1997 | Darouiche et al. |
| 5,687,714 A | 11/1997 | Kolobow |
| 5,721,359 A | 2/1998 | Dunn et al. |
| 5,763,430 A | 6/1998 | Zasloff |
| 6,117,332 A | 9/2000 | Hatch et al. |
| 6,228,393 B1 | 5/2001 | DiCosmo et al. |
| 6,329,488 B1 | 12/2001 | Terry et al. |
| 6,350,738 B1 | 2/2002 | Savage et al. |
| 6,486,148 B2 | 11/2002 | Savage et al. |
| 6,562,318 B1 | 5/2003 | Filler |
| 6,582,713 B2 | 6/2003 | Newell et al. |
| 6,673,771 B1 | 1/2004 | Greene et al. |
| 6,767,904 B2 | 7/2004 | Savage et al. |
| 6,803,066 B2 | 10/2004 | Traeder |
| 6,872,303 B2 | 3/2005 | Knapp et al. |
| 6,939,376 B2 | 7/2005 | Shulze et al. |
| 7,282,214 B2 | 10/2007 | Wilcox et al. |
| 7,381,439 B2 | 6/2008 | Hilgren et al. |
| 7,598,234 B2 | 10/2009 | Savage et al. |
| 7,659,061 B2 | 2/2010 | Hendl et al. |

(Continued)

FOREIGN PATENT DOCUMENTS

| CN | 101378761 | 3/2009 |
| CN | 102172356 | 9/2011 |

(Continued)

OTHER PUBLICATIONS

Rausch, Virtual Textbook of Organic Chemistry, Heterocyclic Chemistry, 1999, pp. 1-14, recovered from https://www2.chemistry.msu.edu/faculty/reusch /VirtTxtJml/heterocy.htm on Jun. 1, 2017.*
Zaragoza Dorwald, Side Reactions in Organic Synthesis, 2005, WILEY-VCH Verlag GmbH & Co. KGaA, Weinheim, Preface. p. IX.*
U.S. Appl. No. 13/783,007, filed Mar. 1, 2013, Savage.
U.S. Appl. No. 14/866,213, filed Sep. 25, 2015, Savage.
U.S. Appl. No. 15/076,313, filed Mar. 21, 2016, Beus et al.
U.S. Appl. No. 15/135,900, filed Apr. 22, 2016, Savage et al.
U.S. Appl. No. 15/135,928, filed Apr. 22, 2016, Savage et al.
Alafort et al., "Lys and Arg in UBI: A specific site for a stable Tc-99m complex?", Nuclear Medicine and Biology 30 (2003) 605-615.

(Continued)

*Primary Examiner* — Paul A Zucker
(74) *Attorney, Agent, or Firm* — Workman Nydegger

(57) ABSTRACT

Disclosed herein are methods of making ceragnenin compounds for treating, preventing, or diagnosing diseases, disorders, or conditions associated with bacterial or viral infections, cancer, inflammation, and osteogenesis. Ceragenin compounds display broad-spectrum antibacterial activity utilizing a mode of action similar to antimicrobial peptides, but without the high synthesis costs and susceptibility to proteolytic degradation. Ceragenin compounds reproduce the amphiphilic morphology found in many antimicrobial peptides and display potent and diverse biological activities, including anti-bacterial, anti-cancer, anti-inflammatory, bone growth promotion, and wound healing promotion.

27 Claims, No Drawings

(56) References Cited

U.S. PATENT DOCUMENTS

| | | | |
|---|---|---|---|
| 7,754,705 B2 | 7/2010 | Savage et al. |
| 7,854,941 B2 | 12/2010 | Urban et al. |
| 7,993,903 B2 | 8/2011 | Hayakawa et al. |
| 821,187 A1 | 7/2012 | Savage et al. |
| 8,529,681 B1 | 9/2013 | Hibbs et al. |
| 8,623,416 B2 | 1/2014 | Zasloff et al. |
| 8,691,252 B2 | 4/2014 | Savage |
| 8,784,857 B2 | 7/2014 | Savage |
| 8,932,614 B2 | 1/2015 | Savage et al. |
| 8,945,217 B2 | 2/2015 | Savage et al. |
| 8,975,310 B2 | 3/2015 | Savage |
| 9,155,746 B2 | 10/2015 | Genberg et al. |
| 9,161,942 B2 | 10/2015 | Genberg et al. |
| 9,314,472 B2 | 4/2016 | Beus et al. |
| 9,345,655 B2 | 5/2016 | Vazquez et al. |
| 9,387,215 B2 | 7/2016 | Beus et al. |
| 2002/0091278 A1 | 7/2002 | Savage et al. |
| 2003/0018306 A1 | 1/2003 | Bucay-Couto et al. |
| 2003/0099717 A1 | 5/2003 | Cabrera |
| 2003/0170354 A1 | 9/2003 | Beelman et al. |
| 2004/0009227 A1 | 1/2004 | Yao |
| 2004/0011358 A1 | 1/2004 | Smaldone et al. |
| 2004/0018154 A1 | 1/2004 | Pan |
| 2004/0058974 A1 | 3/2004 | Courtney et al. |
| 2004/0071781 A1 | 4/2004 | Chattopadhyay et al. |
| 2004/0126409 A1 | 7/2004 | Wilcox et al. |
| 2004/0134292 A1 | 7/2004 | Roth |
| 2004/0170563 A1 | 9/2004 | Meade |
| 2004/0259445 A1 | 12/2004 | Hilfenhaus et al. |
| 2005/0032765 A1 | 2/2005 | Savage et al. |
| 2005/0075321 A1 | 4/2005 | Ahlem et al. |
| 2005/0244468 A1 | 11/2005 | Huang et al. |
| 2005/0267051 A1 | 12/2005 | Lee et al. |
| 2006/0062742 A1 | 3/2006 | Davis et al. |
| 2006/0269485 A1 | 11/2006 | Friedman et al. |
| 2007/0053788 A1 | 3/2007 | Zhao |
| 2007/0077292 A1 | 4/2007 | Pinsky |
| 2007/0106393 A1 | 5/2007 | Miles et al. |
| 2007/0190066 A1 | 8/2007 | Savage et al. |
| 2007/0190067 A1 | 8/2007 | Savage et al. |
| 2007/0190558 A1 | 8/2007 | Savage et al. |
| 2008/0124376 A1 | 5/2008 | Pruitt et al. |
| 2008/0174035 A1 | 7/2008 | Winterton |
| 2008/0188819 A1 | 8/2008 | Kloke et al. |
| 2008/0279944 A1 | 11/2008 | Sawhney |
| 2009/0016973 A1 | 1/2009 | Ratcliff et al. |
| 2009/0054295 A1 | 2/2009 | Vicari et al. |
| 2009/0068122 A1 | 3/2009 | Pilch et al. |
| 2009/0099531 A1 | 4/2009 | Griesbach, III |
| 2009/0252781 A1 | 10/2009 | Sawhney et al. |
| 2009/0324517 A1 | 12/2009 | Kline |
| 2010/0022481 A1 | 1/2010 | Wang et al. |
| 2010/0092398 A1 | 4/2010 | Reynolds |
| 2010/0226884 A1 | 9/2010 | Chang et al. |
| 2010/0310478 A1 | 12/2010 | Fitzgerald et al. |
| 2010/0330086 A1 | 12/2010 | Savage et al. |
| 2011/0091376 A1 | 4/2011 | Savage et al. |
| 2011/0123624 A1 | 5/2011 | Zasloff |
| 2011/0135742 A1 | 6/2011 | Kim et al. |
| 2011/0230589 A1 | 9/2011 | Maggio et al. |
| 2012/0088733 A1 | 4/2012 | Kim et al. |
| 2012/0107382 A1 | 5/2012 | Savage et al. |
| 2012/0128793 A1 | 5/2012 | Miller et al. |
| 2013/0004586 A1 | 1/2013 | Vachon |
| 2013/0022651 A1 | 1/2013 | Savage |
| 2013/0040265 A1 | 2/2013 | Park et al. |
| 2013/0137668 A1 | 5/2013 | Fein et al. |
| 2013/0236619 A1 | 9/2013 | Savage |
| 2013/0243823 A1 | 9/2013 | Genberg et al. |
| 2013/0243842 A1 | 9/2013 | Genberg et al. |
| 2013/0280312 A1 | 10/2013 | De Szalay |
| 2013/0280391 A1 | 10/2013 | Savage |
| 2014/0194401 A1 | 7/2014 | Genberg et al. |
| 2014/0219914 A1 | 8/2014 | Govindan et al. |
| 2014/0271761 A1 | 9/2014 | Savage et al. |
| 2014/0274913 A1 | 9/2014 | Savage et al. |
| 2014/0305461 A1 | 10/2014 | Pimenta et al. |
| 2014/0336131 A1 | 11/2014 | Savage et al. |
| 2014/0363780 A1 | 12/2014 | Vazquez et al. |
| 2015/0093423 A1 | 4/2015 | Savage et al. |
| 2015/0110767 A1 | 4/2015 | Savage et al. |
| 2015/0140063 A1 | 5/2015 | Savage |
| 2015/0203527 A1 | 7/2015 | Savage |
| 2015/0239928 A1 | 8/2015 | Savage |
| 2015/0258121 A1 | 9/2015 | Darien et al. |
| 2015/0258122 A1 | 9/2015 | Beus et al. |
| 2015/0258123 A1 | 9/2015 | Savage et al. |
| 2015/0314342 A1 | 11/2015 | Beus et al. |
| 2015/0366880 A1 | 12/2015 | Genberg et al. |
| 2015/0374719 A1 | 12/2015 | Genberg et al. |
| 2015/0374720 A1 | 12/2015 | Genberg et al. |
| 2016/0022702 A1 | 1/2016 | Savage et al. |
| 2016/0045421 A1 | 2/2016 | Vazquez et al. |
| 2016/0052959 A1 | 2/2016 | Savage |
| 2016/0096864 A1 | 4/2016 | Savage |
| 2016/0193232 A1 | 7/2016 | Beus et al. |
| 2017/0035677 A1 | 2/2017 | Vazquez et al. |
| 2017/0080128 A1 | 3/2017 | Genberg et al. |
| 2017/0137459 A1 | 5/2017 | Savage |
| 2017/0210776 A1 | 7/2017 | Savage |
| 2017/0232004 A1 | 8/2017 | Savage et al. |
| 2017/0258963 A1 | 9/2017 | Savage et al. |

FOREIGN PATENT DOCUMENTS

| | | |
|---|---|---|
| DE | 1037074 | 8/1958 |
| EP | 0341951 | 11/1989 |
| EP | 1208844 | 5/2002 |
| EP | 1219631 | 7/2002 |
| JP | 02014741 | 1/1990 |
| JP | H0474026 | 11/1992 |
| JP | 06153779 | 6/1994 |
| JP | 07501826 | 2/1995 |
| JP | 09248454 | 9/1997 |
| JP | 2002505292 | 2/2002 |
| JP | 2002255771 | 9/2002 |
| JP | 2002534532 | 10/2002 |
| JP | 2002538093 | 11/2002 |
| JP | 2004506645 | 3/2004 |
| JP | 2010533051 | 10/2010 |
| JP | 2010538074 | 12/2010 |
| JP | 2011527702 | 11/2011 |
| JP | 2014500741 | 1/2014 |
| WO | WO 1995024415 | 9/1995 |
| WO | WO9827106 | 6/1998 |
| WO | WO 1999044616 | 9/1999 |
| WO | WO 2000042058 | 7/2000 |
| WO | WO 2002014342 | 2/2002 |
| WO | WO2002067979 | 9/2002 |
| WO | WO2003015757 | 2/2003 |
| WO | WO03090799 | 11/2003 |
| WO | WO2004082588 | 9/2004 |
| WO | WO 2004112852 | 12/2004 |
| WO | WO 2007/089903 A2 * | 8/2007 |
| WO | WO 2007089903 | 8/2007 |
| WO | WO 2007089906 | 8/2007 |
| WO | WO 2007089907 | 8/2007 |
| WO | WO 2007134176 | 11/2007 |
| WO | 2009049370 | 4/2009 |
| WO | WO 2008038965 | 4/2009 |
| WO | WO 2009079066 | 6/2009 |
| WO | WO2009144708 | 12/2009 |
| WO | WO2010006192 | 1/2010 |
| WO | WO2010036427 | 4/2010 |
| WO | WO2010062562 | 6/2011 |
| WO | WO2011066260 | 6/2011 |
| WO | WO2011109704 | 9/2011 |
| WO | WO2012061651 | 5/2012 |
| WO | WO2013029055 | 2/2013 |
| WO | WO2013029059 | 2/2013 |
| WO | WO2013040269 | 3/2013 |
| WO | WO 2013109236 | 7/2013 |

(56) References Cited

FOREIGN PATENT DOCUMENTS

| WO | 2013167743 | 11/2013 |
|---|---|---|
| WO | 2014062960 | 4/2014 |
| WO | 2016186821 | 11/2016 |

OTHER PUBLICATIONS

Alhanout K et al: "Squalamine as an example of a new potent antimicrobial agents class: a critical review.", Current Medicinal Chemistry 2010, vol. 17, No. 32, 2010, pp. 3909-3917.
Atiq-Ur-Rehman Li C et al: "Preparation of Amino Acid-Appended Cholic Acid Derivatives as Sensitizers of Gram-Negative Bacteria", Tetrahedron Letters, Elsevier, Amsterdam, NL, vol. 40, No. 10, Mar. 5, 1999 (Mar. 5, 1999), pp. 1865-1868, XP004155984, ISSN: 0040-4039, DOI: 10.1016/S0040-4039(99)00075-1.
Bellini et al., "Cholic and deoxycholic acids derivatives (Part I). Antimicrobial activity of cholane compounds", European J. of Medicinal Chem., 18(2), pp. 185-190, 1983.
Bellini et al., "Cholic and deoxycholic acids derivatives (Part II). Antimicrobial activity of cholane compounds", European J. of Medicinal Chem., 18(2), pp. 191-195, 1983.
Berge et al., "Pharmaceutical Salts", Journal of Pharmaceutical Sciences, Jan. 1977, vol. 66, No. 1, pp. 1-19.
Bridot et al., "Hybrid Gadolinium Oxide Nanoparticles: Multimodal Contrast Agents for in Vivo Imaging", Journal of American Chemical Society, vol. 129, No. 16, pp. 5076-5084, Mar. 31, 2007.
Britton et al, "Imaging bacterial infection with 99mTc-ciprofloxacin (Infection)", Journal of Clinical Pathology, vol. 55, pp. 817-823, Apr. 6, 2015.
Brown, "Bioisosteres in Medicinal Chemistry, First Edition", edited by Nathan Brown, 2012, Ch. 2 Classical Bioisosteres, pp. 1-52.
Bucki et al., "Resistance of the antibacterial agent ceragenin CSA-13 to inactivation by DNA or F-actin and its activity in cystic fibrosis sputum", Journal of Antimicrobial Chemotherapy (2007) 60: 535-545, 11 pages.
Bucki et al., "Salivary mucins inhibit antibacterial activity of the cathelicidin-derived LL-37 peptide but not the cationic steroid CSA-13", Journal of Antimicrobial Chemotherapy (2008) 62: 329-335, 7 pages.
Chin et al, "Antimicrobial Activities of Ceragenins against Clinical Isolates of Resistant *Staphylococcus aureas*", Antimicrobial Agents and Chemotherapy, vol. 51, No. 4, Apr. 2007, p. 1268-1273.
Clara et al., "Preclinical evaluation of magainin-A as a contraceptive antimicrobial agent", Fertility and Sterility 81 (5), pp. 1357-1365, 2004.
Ding, et al., "Origins of cell selectivity of cationic steroid antibiotics", Journal of American Chemical Society, Oct. 2004, pp. 13642-13648.
Dörwald, "Side reactions in organic synthesis", 2005, Wiley-VCH Verlag GmbH & co., KGAA Weinhelm, Preface. p. IX.
Epand et al., "Bacterial lipid composition and the antimicrobial efficacy of cationic steroid compounds (Ceragenins)", BBA, 2007, pp. 65-78.
Fichna et al., "Synthesis of Target-Specific Radiolabeled Peptides for Diagnostic Imaging", Bioconjugate Chem., 2003, 14, 3-17, American Chemical Society.
Fritsch et al, "In Vitro Activity of Nine Developmental Cationic Steroid Compounds (Ceragenins) against Clinical Isolates of Clostridium difficile", The 46th Interscience Conference on Antimicrobial Agents and Chemotherapy, Sep. 27, 2006, pp. 1-1.
Guan et al: "Preparation and Characterization of Cholic Acid-Derived Antimicrobial Agents with Controlled Stabilities", Organic Letters, American Chemical Society, US, vol. 2, No. 18, Sep. 7, 2000 (Sep. 7, 2000), pp. 2837-2840.
Guan et al: "Supporting Information: Preparation and Characterization of Cholic Acid-Derived Antimicrobial Agents with Controlled Stabilities", Organic Letters, Aug. 17, 2000 (Aug. 17, 2000), pp. 1-7, XP55017313, Retrieved from the Internet: URL:http://pubs.acs.org/doi/suppl/10.1021/ol0062704/suppl_file/ol0062704_sl.pdf.

Howell et al., "Ceragenins: A 1-18, class of Antiviral Compounds to Treat Orthopox Infections", Journal of Investigative Dermatology, vol. 129, No. 11, Jun. 11, 2009, pp. 2688-2675.
Isogai E et al: "Ceragenin CSA-13 exhibits antimicrobial activity against cariogenic and periodontopathic bacteria", Oral Microbiology and Immunology, vol. 24, No. 2, Apr. 2009 (Apr. 2009), pp. 170-172.
International Search Report for PCT Application No. PCT/US2009/047485 dated Feb. 17, 2010.
International Search Report for PCT Application No. PCT/US2011/059225 dated Jan. 31, 2012.
International Search Report for PCT Application No. PCT/US2012/047750, dated Oct. 5, 2012.
International Search Report for PCT Application No. PCT/US2012/055244 dated Dec. 5, 2012.
International Search Report for PCT Application No. PCT/US2012/055248 dated Feb. 14, 2013.
International Search Report for PCT Application No. PCT/US2013/038090, dated Jul. 24, 2013.
International Search Report for PCT Application No. PCT/US2014/034986 dated Aug. 28, 2014.
International Search Report for PCT Application No. PCT/US2013/065510 dated Apr. 30, 2015.
International Search Report for PCT Application No. PCT/US2015/020166 dated Sep. 2, 2015.
International Search Report for PCT Application No. PCT/US2015/038029 dated Sep. 29, 2015.
International Search Report for PCT Application No. PCT/US2015/046412 dated Dec. 1, 2015.
International Search Report for PCT Application No. PCT/US2015/054434 dated Dec. 23, 2015.
Iuliano, "Synthesis of four cholic acid-based CSPs containing 2-naphthyl carbamate and 3,5-dinitrophenylcarbamate moieties and their evaluation in the HPLC resolution of racemic compounds", Tetrahedron: Asymmetry 13 (2002) 1265-1275.
Lai, et al., "Controlled Released of a Bactericidal Ceragenin-Polymer Conjugate", Sep. 27, 2006, p. 1, 46th Annual Interscience Conference on Antimicrobial Agents and Chemotherapy.
Lankinen et al., "Ga-Dota-Peptide Targeting VAP-1 for in Vivo Evaluation of Inflammatory and Infectious Bone Conditions", 52nd Annual Meeting of the Orthopaedic Research Society.
Leszczynska et al., "Potential of ceragenin CSA-13 and its mixture with pluronic F-127 as treatment of topical bacterial infections", Journal of Applied Microbiology, vol. 110, No. 1, Oct. 21, 2010, pp. 229-238.
Li, et al., "Antimicrobial Activities of Amine- and Guanidine-functionalized Cholic Acid Derivatives", Antimicrobial Agents and Chemotherapy, American Society for Microbiology, Washington DC, US, vol. 43, No. 6, Jun. 1999, pp. 1347-1349.
Li et al., "Incremental conversion of Outer-Membrane Permeabilizers into Potent Antibiotics for Gram-Negative Bacteria", J. Am. Chem. Soc. 1999, 121, 931-940.
Lowe et al., "Effect of Hydrophobicity of a Drug on its Release from Hydrogels with Different Topological Structures" Journal of Polymer Science (1999) 73: 1031-1039 (9 pages).
Massoud et al., "Molecular imaging in living subjects: seeing fundamental biological processes in a new light", Genes & Development 17: 545-580 2003, Cold Spring Harbor Laboratory Press.
Muñoz-Juárez et al., "Wide-Lumen Stapled Anastomosis vs. Conventional End-to-End Anastomosis in the Treatment of Crohn's Disease", Dis Colon Rectum 2001; 44: No. 1, 20-26).
Perry et al., "Assessing peri-implant tissue infection prevention in a percutaneous model", Journal of Biomedical Materials Research Part B: Applied Biomaterials, vol. 02B, Nov. 19, 2009, pp. 397-408.
Pitten F-A, et al., "Efficacy of Cetylpyridinium Chloride Used as Oropharyngeal Antiseptic" Arzenimittel Forschung. Drug Research, ECV Editio Cantor Verlag, Aulendorf, DE, vol. 51, No. 7, Jan. 1, 2001, pp. 588-595.
Roohi et al., Prepration, quality control and biological evaluation of 99m-Tc-labelled cationic steroid antibiotic (CSA-13), Radiochim. Acta 197, 57-62 (2009).

(56) References Cited

OTHER PUBLICATIONS

Savage, et al., "Antibacterial Activities of Thin Films Containing Ceragenins", Microbial Surfaces: Structure, Interactions and Reactivity, ACS, May 30, 2008, pp. 65-78.
Paul B. Savage, et al: "Antibacterial Properties of cationic steroid antibiotics", FEMS Microbiology Letters, vol. 217, Nov. 2002, pp. 1-7.
Savage et al, "Thin Films Containing Ceragenins Prevent Biofilm Formation on Endotracheal Tubes", 9th International Federation of Infection Control Congress, Oct. 14, 2008, pp. 1-1.
P. B. Savage, et al., "Use of a Ceragenin-Based Coating to Prevent Bacterial Colonization of Urinary Catheters", 48th Annual Interscience Conference on Anti-Microbial Agents & Chemotherapy, Oct. 26, 2008, pp. 1-1.
Schmidmaier et al., "Local Application of Growth Factors (Insulin-Like Growth Factor-1 and Transforming Growth Factor-β1) From a Biodegradable Poly(D, L-lactide) Coating of Osteosynthetic Implants Accelerates Fracture Healing in Rats", Bone vol. 28 No. 4, Apr. 2001.
Shi et al., "Multi-center randomized double-blind clinical trial on efficacy of a mouthwash containing 0.1% cetylpiridinium chloride on gingivitis and plaque and its safety", Chinese Journal of Evidence-Based Medicine (Sep. 2003, vol. 3, No. 3, pp. 171-177).
Sinclair et al., "Development of a broad spectrum polymer-released antimicrobial coating for the prevention of resistant strain bacterial infections", Journal of Biomedical Materials Research Part A, vol. 100A, No. 10, May 24, 2012, pp. 2732-2738.
Steeneveld et al., "Cow-specific treatment of clinical mastitis: an economic approach", Journal of Dairy Science vol. 94, Jan. 2011, pp. 174-188.
Suzuki et al., "Molecular Genetics of Plant Sterol Backbone Synthesis", 2007; Lipids; 42: 47-54.
Van Bambeke et al: "The bacterial envelope as a target for novel anti-MRSA antibiotics", Trends in Pharmacological Sciences, Elsevier, Haywarth, GB, vol. 29, No. 3, Feb. 11, 2008 (Feb. 11, 2008), pp. 124-134.
Van Den Bogaard et al., "Antibiotic Usage in Animals: Impact on Bacterial Resistance and Public Health"; 1999; Drugs; 58 (4): 589-607.
Welling et al., "Radiochemical and biological characteristics of 99m-Tc-UBI 29-41 for imaging of bacterial infections", Nuclear Medicine and Biology 29 (2002) 413-422.
Williams et al., "In vivo efficacy of a silicone-cationic steroid antimicrobial coating to prevent implant-related infection", Biomaterials, Nov. 2012: 33(33): 8641-8656 (Department of Brigham Young University).
Wu et al., "Biodegradable hydrophobic-hydrophilic hybrid hydrogels: swelling behavior and controlled drug release", Journal of Biomaterials Science Polymer Edition (J. Biomatter. Sci. Polymer Ed.) (2008) 19 (4): 411-429 (20 pages, including copyright information).
Xin-Zhong Lai et al., "Ceragenins: Cholic Acid-Based Mimics of Antimicrobial peptides", Account of Chemical Research vol. 41, No. 10, Oct. 21, 2008, pp. 1233-1240.
Yin, et al., "Antiangiogenic Treatment Delays Chondrocyte Maturation and Cone Formation During Lim Skeletogenesis", Journal of Bone and Mineral Research, American Society for Bone and Mineral Research, New York, NY, US, vol. 17, No. 1, Jan. 1, 2002.
Zanger et al., "Structure-Activity Relationship and Drug Design", Remington's Pharmaceutical Sciences, Chapter 27, 16th Edition, 1980, pp. 420-425.
BASF, Pluronic® Block Copolymer NF Grades (Poloxamer NF Grades), Technical Bulletive (2004).
Bush, "*Staphylococcal* Infections", Merck Manuals Professional Edition, http://www.merckmanuals.com/professional/infectious-diseases/gram-positive-cocci/staphylococcalinfections.
Cipolla et al., "Inhaled antibiotics to treat lung infection", Pharm Pat Anal., Sep. 2013.

Dennison et al., "Anticancer α-Helical Peptides and Structure/Function Relationships Underpinning their Interactions with Tumour Cell Membranes", Current Protein and Peptide Science, 2006, 7, No. 6, pp. 1-13.
Derakhshandeh et al., "Thermosensitive Pluronic hydrogel: prolonged injectable formulation for drug abuse", Drug Design, Development and Therapy, 2010, 255-262.
Elder et al., "The Utility of Sulfonate Salts in Drug Development", Journal of Pharmaceutical Sciences 99(7): 2948-2961.
Food definition, Merriam Webster, https://www.merriam-webster.com/dictionary/food, Accessed Feb. 12, 2018.
Jones et al, "Physicochemical Characterization of Hexetidine-Impregnated Endotracheal Tube Poly(Vinyl Chloride) and Resistance to Adherence of Respiratory Bacterial Pathogens", Pharmaceutical Research 19(6): 818-824.
Journal of Ocular Pharmacology and Therapeutics, vol. 27, Issue 1, Table of Contents (Mary Ann Liebert, Inc. publishers), Retrieved from internet <URL:http://online.libertpub.com/toc/jop/27/1>, Downloaded Dec. 1, 2017, 5 pages.
K. Leszczynska et al., "Antibacterial activity of the human host defence peptide LL-37 and selected synthetic cationic lipids against bacteria associated with oral and upper respiratory tract infections", Journal of Antimicrobial Chemotherapy Advance Access, Published Nov. 7, 2012.
Louw et al., "Recueil des Travaux Chimiques des Pays-Bas et la Belgique", vol. 73, pp. 667-676, 1954.
Papo et al., "Host peptides as new weapons in cancer treatment", CMLS Cell. Mol. Life Sci. 62 (2005), 784-790.
Polat et al., "In Vitro Amoebicidal Activity of a Ceragenin, Cationic Steroid Antibiotic-13, Against Acanthamoeba castellanii and Its Cytotoxic Potential", Journal of Ocular Pharmacology and Therapeutics, vol. 27, No. 1, 2011.
Press release (Ceragenix Pharmaceuticals, Wayne State University, Brigham Young University, Systemic Anti-Infectives, Preclinical Title—Ceragenin™ Compound demonstrates potent activity multidrug resistant bacterial strains of Pseudomonas, Denver, Co-Published Dec. 20, 2007).
Pycock, "The Dirty Mare", https://www.equine-reproduction.com/articles/DirtyMare.shtml, 2003.
Survey Research on Behcet's Disease, 2005 to 2007 Comprehensive Survey Reports, 2008, pp. 34-39.
U.S. Appl. No. 15/934,534, filed Mar. 23, 2018, Savage, Paul B.
U.S. Appl. No. 15/895,848, filed Feb. 13, 2018, Genberg, et al.
U.S. Appl. No. 15/926,534, filed Mar. 20, 2018, Savage.
U.S. Appl. No. 15/926,577, filed Mar. 20, 2018, Savage et al.
Huang L. et al.: "Synthesis and characterization of organometallic rhenium(I) and technetium(I) bile acid complexes" Journal of organometallic chemistry, Elsevier-Sequoia S.A. Lausanne, CH, col. 694, No. 20, Sep. 15, 2009, pp. 3247-3253.
International Search Report for PCT Application No. PCT/US2018/023566 dated Mar. 21, 2018.
Piktel et al. Sporicidal Activity of Ceragenin CSA-13 Against Bacillus Subtillis, Scientific Reports, vol. 7, Mar. 15, 2017 [retrieved on Apr. 24, 2018. Retreived from the internet: <URL:https://www.nature.com/articles/srep44452.pdf> Entire Document.
Uncategorized: CSA Biotechnologies LLC, Apr. 5, 2011.
"Martindale: the complete drug reference, Cetrimide; Cetylpyridinium chloride ED-PARFITT K", Jan. 1, 2000, pp. 1105-1106.
Barton, Journal of Clinical Investigation, vol. 118, No. 2, Feb. 2008, Review Series, pp. 413-420.
Feng, Theses Brigham Young University, BYU Scholars Archive, dated Dec. 19, 2011, 892.
Chen et al, J Drug Target, Dec. 2012; 20(10):856-63, 892.
Ogata et al. Intramammary application of ozone therapy to acute clinical mastitis in dairy cows. J. Vet. Med. Sci. 62(7): 681-686, 2000.
de Haas et al. Associations between pathogen-specific cases of clinical mastitis and somatic cell count patterns. J. Dairy Sci. 87: 95-105.

\* cited by examiner

METHODS FOR THE SYNTHESIS OF CERAGENINS

CROSS-REFERENCE TO RELATED APPLICATIONS

This application claims the benefit of U.S. Provisional Patent Application No. 62/151,002, filed on Apr. 22, 2015, U.S. Provisional Patent Application No. 62/165,006, filed on May 21, 2015, and U.S. Provisional Patent Application No. 62/191,922, filed on Jul. 13, 2015, the disclosures of which are incorporated herein in their entirety.

BACKGROUND OF THE INVENTION

1. Field

The present application relates to the fields of pharmaceutical chemistry, biochemistry, and medicine. In particular, the present application relates to methods of making cationic steroidal antimicrobials ("CSAs" or "ceragenins").

2. Related Technology

Endogenous antimicrobial peptides, such as the human cathelicidin LL-37, play key roles in innate immunity. LL-37 is found in airway mucus and is believed to be important in controlling bacterial growth in the lung. Antimicrobial peptides are found in organisms ranging from mammals to amphibians to insects to plants. The ubiquity of antimicrobial peptides has been used as evidence that these compounds do not readily engender bacterial resistance. In addition, considering the varied sequences of antimicrobial peptides among diverse organisms, it is apparent that they have evolved independently multiple times. Thus, antimicrobial peptides appear to be one of "Nature's" primary means of controlling bacterial growth. However, clinical use of antimicrobial peptides presents significant issues including the relatively high cost of producing peptide-based therapeutics, the susceptibility of peptides to proteases generated by the host and by bacterial pathogens, and deactivation of antimicrobial peptides by proteins and DNA in lung mucosa.

An attractive means of harnessing the antibacterial activities of antimicrobial peptides without the issues delineated above is to develop non-peptide mimics of antimicrobial peptides that display the same broad-spectrum antibacterial activity utilizing the same mechanism of action. Non-peptide mimics would offer lower-cost synthesis and potentially increased stability to proteolytic degradation. In addition, control of water solubility and charge density may be used to control association with proteins and DNA in lung mucosa.

With over 1,600 examples of antimicrobial peptides known, it is possible to categorize the structural features common to them. While the primary sequences of these peptides vary substantially, morphologies adopted by a vast majority are similar. Those that adopt alpha helix conformations juxtapose hydrophobic side chains on one face of the helix with cationic (positively charged) side chains on the opposite side. As similar morphology is found in antimicrobial peptides that form beta sheet structures: hydrophobic side chains on one face of the sheet and cationic side chains on the other.

We have developed small molecule, non-peptide mimics of antimicrobial peptides, termed ceragenins or CSAs. These compounds reproduce the amphiphilic morphology in nti-microbial peptides, represented above by CSA-13, and display potent, as well as diverse, biological activities (including, but not limited to anti-bacterial, anti-cancer, anti-inflammatory, promoting bone growth, promoting wound healing, etc.). Lead ceragenins can be produced at a large scale, and because they are not peptide based, they are not substrates for proteases. Consequently, the ceragenins represented an attractive compound class for producing pharmaceutically-relevant treatments.

SUMMARY

Certain embodiments described herein relate to methods of making a compound of Formula (I) or Formula (III), comprising the steps of:

(a) reacting a compound of Formula (1) and $R_1R_2$—NH

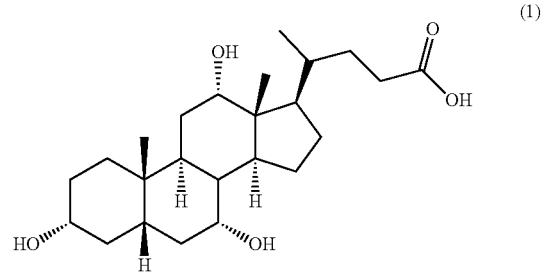

to form a compound of Formula (2):

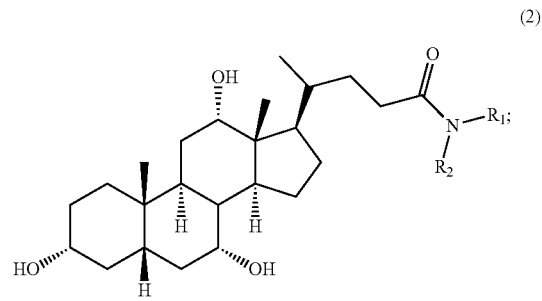

(b) optionally reducing a compound of Formula (2) to form a compound of Formula (3):

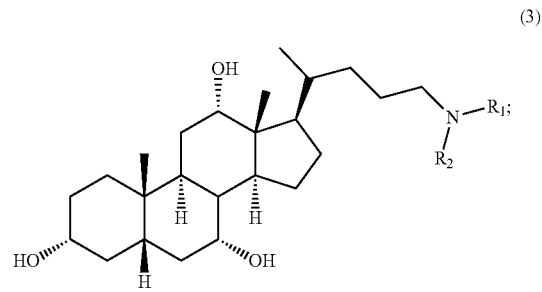

(c1) optionally protecting a compound of Formula (3) with an amine protecting group (PG) to form a compound of Formula (4):

(4)

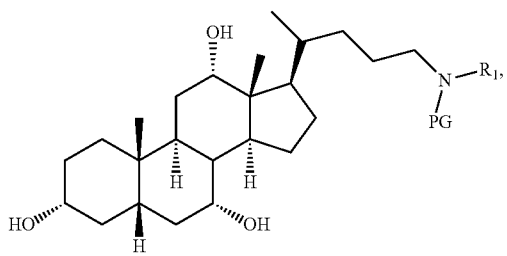

or (c2) optionally protecting a compound of Formula (2) with an amine protecting group (PG) to form a compound of Formula (10):

(10)

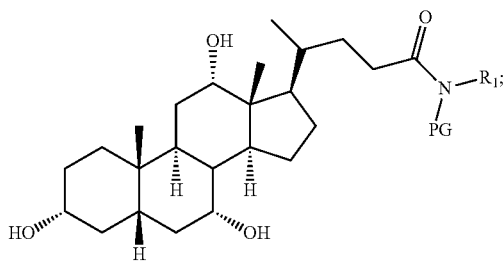

(d1) reacting a compound of Formula (3) or Formula (4) with a compound of Formula (A)

(A)

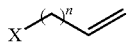

to form a compound of Formula (5a) or (5b):

(5a)

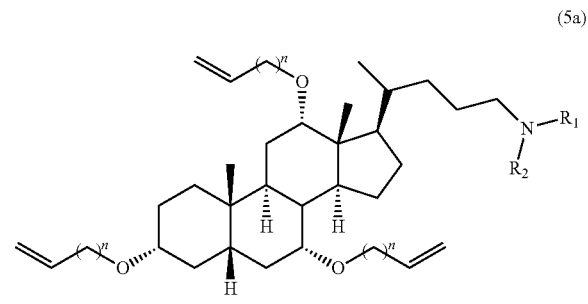

or (5b)

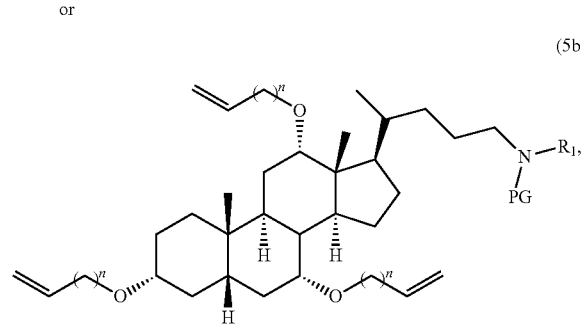

or (d2) reacting a compound of Formula (2) or Formula (10) with a compound of Formula (A) to form a compound of Formula (11a) or (11b):

(11a)

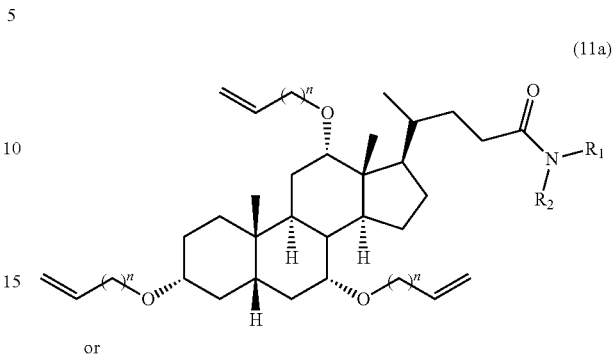

or (11b)

(e1) subjecting a compound of Formula (5a) or (5b) to hydroboration and oxidation conditions, followed by reaction with a compound of Formula (B)

$R_3\text{—}SO_2Cl$ (B)

to form a compound of Formula (6a) or (6b):

(6a)

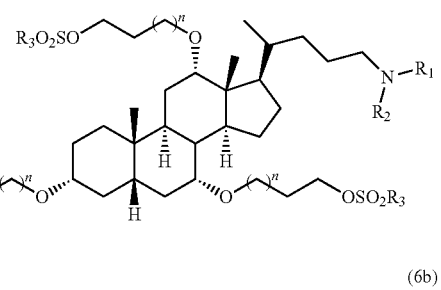

or (6b)

or (e2) subjecting a compound of Formula (11a) or (11b) to hydroboration and oxidation conditions, followed by reaction with a compound of Formula (B) to form a compound of Formula (12a) or (12b):

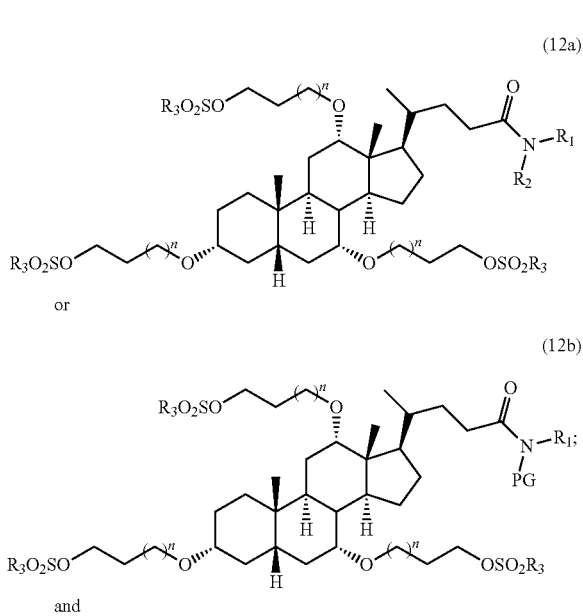

(f1) reacting a compound of Formula (6a) or (6b) and R₄R₅—NH, followed by optional deprotection to form a compound of Formula (I):

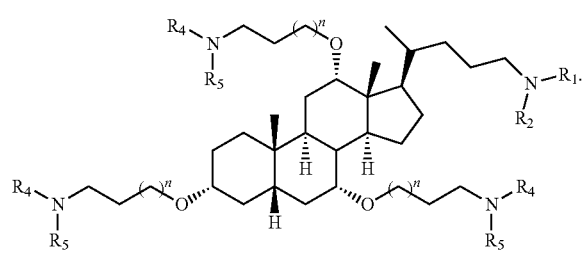

or (f2) reacting a compound of Formula (12a) or (12b) and R₄R₅—NH, followed by optional deprotection to form a compound of Formula (III):

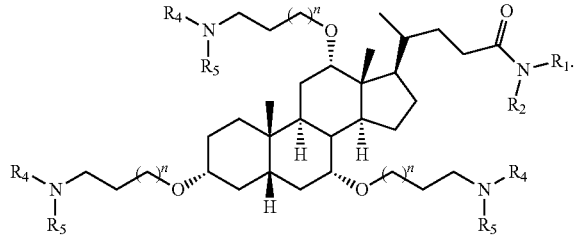

In some embodiments, X is independently selected from the group consisting of —F, —Cl, —Br, —I, tosylate, brosylate, nosylate, mesylate, and triflate.

In some embodiments, n is an integer from 1 to 25.

In some embodiments, $R_1$, $R_2$, $R_4$, and $R_5$ are independently selected from the group consisting of hydrogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, optionally substituted (5 to 10 membered heterocyclyl)-$C_1$-$C_6$ alkyl, a suitable amine protecting group, and an optionally substituted amide, wherein $R_1$, $R_2$, $R_4$, and $R_5$, together with the nitrogen to which they are attached, form an optionally substituted amide (—NR—C(=O)—R).

In some embodiments, $R_3$ is selected from the group consisting of optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, optionally substituted amido, and optionally substituted (5 to 10 membered heterocyclyl)-$C_1$-$C_6$ alkyl.

In some embodiments, $R_1$ and $R_2$, together with the atoms to which they are attached form an optionally substituted 5 to 10 membered heterocyclyl ring.

In some embodiments, $R_4$ and $R_5$, together with the atoms to which they are attached form an optionally substituted 5 to 10 membered heterocyclyl ring.

Some embodiments relate to a method of making a compound of Formula (II) or a compound of Formula (IV), comprising:

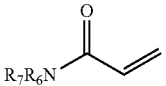

(a) reacting a compound of Formula (2) with

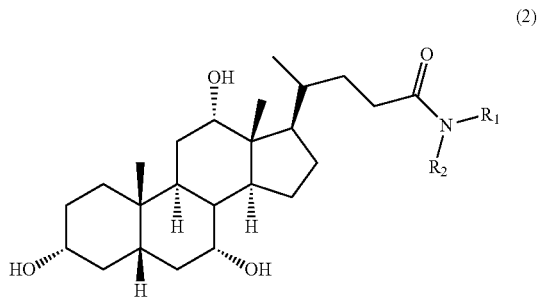

to form a compound of Formula (8):

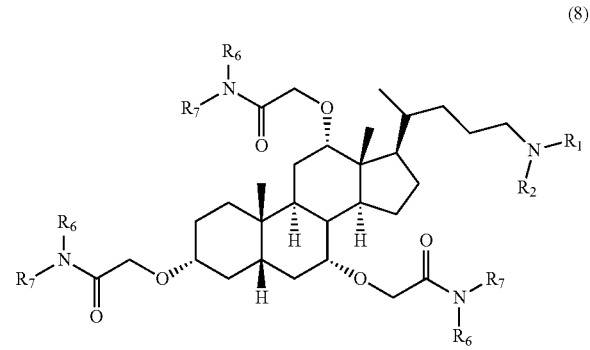

or a compound of Formula (14):

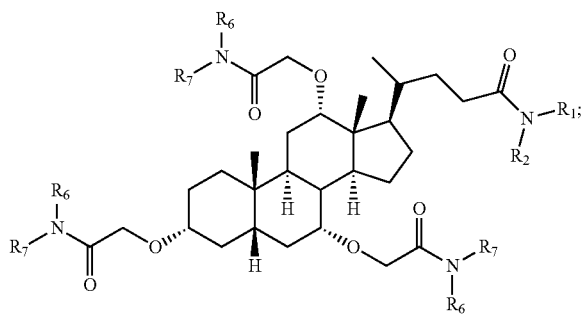

and (b) subjecting a compound of Formula (8) to reducing conditions, followed by optional deprotection, to provide a compound of Formula (II):

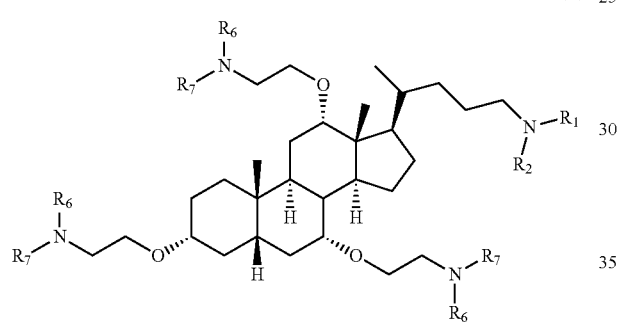

or subjecting a compound of Formula (14) to reducing conditions, followed by optional deprotection, to provide a compound of Formula (IV):

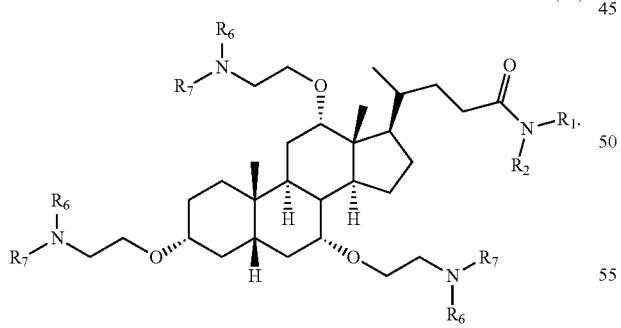

In some embodiments, $R_1$, $R_2$, $R_6$, and $R_7$ are independently selected from the group consisting of hydrogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, optionally substituted (5 to 10 membered heterocyclyl)-$C_1$-$C_6$ alkyl, a suitable amine protecting group, and an optionally substituted amide, wherein $R_1$, $R_2$, $R_4$, and $R_5$, together with the nitrogen to which they are attached, form an optionally substituted amide (—NR—C(=O)—R).

In some embodiments, $R_1$ and $R_2$, together with the atoms to which they are attached form an optionally substituted 5 to 10 membered heterocyclyl ring.

In some embodiments, $R_6$ and $R_7$, together with the atoms to which they are attached form an optionally substituted 5 to 10 membered heterocyclyl ring.

Certain embodiments relate to a method of making a compound of Formula (I), comprising hydroborating a compound of Formula (5), followed by reaction with $R_4R_5N$—$OR_8$ and optional deprotection

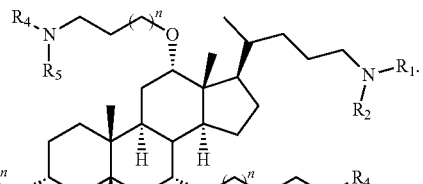

to form a compound of Formula (I):

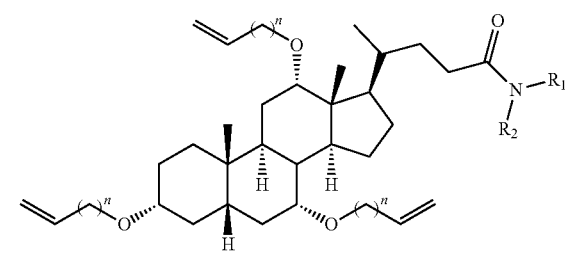

Certain embodiments relate to a method of making a compound of Formula (III), comprising hydroborating a compound of Formula (11), followed by reaction with $R_4R_5N$—$OR_8$ and optional deprotection to form a compound of Formula (III):

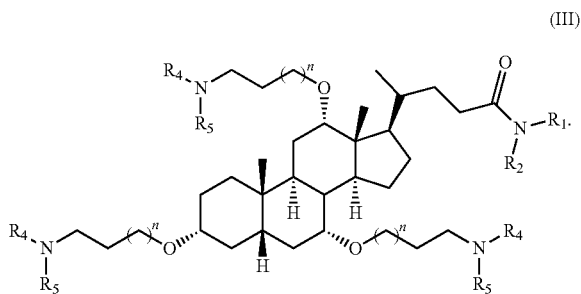

(III)

In some embodiments for making a compound of Formula (I) or Formula (III), n is an integer from 1 to 25.

In some embodiments for making a compound of Formula (I) or Formula (III), $R_1$, $R_2$, $R_4$, and $R_5$ are independently selected from the group consisting of hydrogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, optionally substituted (5 to 10 membered heterocyclyl)-$C_1$-$C_6$ alkyl, a suitable amine protecting group, and an optionally substituted amide, wherein $R_1$, $R_2$, $R_4$, and $R_5$, together with the nitrogen to which they are attached, form an optionally substituted amide (—NR—C(=O)—R).

In some embodiments for making a compound of Formula (I) or Formula (III), $R_3$ is selected from the group consisting of optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, and optionally substituted (5 to 10 membered heterocyclyl)-$C_1$-$C_6$ alkyl.

In some embodiments for making a compound of Formula (I) or Formula (III), $R_8$ is selected from the group consisting of hydrogen, halogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, and optionally substituted (5 to 10 membered heterocyclyl)-$C_1$-$C_6$ alkyl.

In some embodiments, $R_1$ and $R_2$, together with the atoms to which they are attached form an optionally substituted 5 to 10 membered heterocyclyl ring.

In some embodiments, $R_4$ and $R_5$, together with the atoms to which they are attached form an optionally substituted 5 to 10 membered heterocyclyl ring.

Advantanges of the CSA compounds disclosed herein include, but are not limited to, comparable and/or improved antimicrobial activity, stability, and/or pharmaceutical administerability compared to existing CSA compounds and/or simplified synthetis of final CSA compounds and/or intermediate CSA compounds compared to existing synthetic routes.

Additional features and advantages will be set forth in part in the description that follows, and in part will be obvious from the description, or may be learned by practice of the embodiments disclosed herein. It is to be understood that both the foregoing brief summary and the following detailed description are exemplary and explanatory only and are not restrictive of the embodiments disclosed herein or as claimed.

DETAILED DESCRIPTION

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise. As used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. The use of "or" or "and" c means "and/or" unless stated otherwise. Furthermore, use of the term "including" as well as other forms, such as "include", "includes," and "included," is not limiting. As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least." When used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components.

The section headings used herein are for organizational purposes only and are not to be construed as limiting the subject matter described.

As used herein, "$C_a$ to $C_b$" or "$C_{a-b}$" in which "a" and "b" are integers refer to the number of carbon atoms in the specified group. That is, the group can contain from "a" to "b", inclusive, carbon atoms. Thus, for example, a "$C_1$ to $C_4$ alkyl" or "$C_{1-4}$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—.

The term "halogen" or "halo," as used herein, means any one of the radio-stable atoms of column 7 of the Periodic Table of the Elements, e.g., fluorine, chlorine, bromine, or iodine, with fluorine and chlorine being preferred.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 4 carbon atoms. The alkyl group may be designated as "$C_{1-4}$ alkyl" or similar designations. By way of example only, "$C_{1-4}$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "alkoxy" refers to the formula —OR wherein R is an alkyl as is defined above, such as "$C_{1-9}$ alkoxy", including but not limited to methoxy, ethoxy, n-propoxy, 1-methylethoxy (isopropoxy), n-butoxy, iso-butoxy, sec-butoxy, and tert-butoxy, and the like.

As used herein, "alkylthio" refers to the formula —SR wherein R is an alkyl as is defined above, such as "$C_{1-9}$ alkylthio" and the like, including but not limited to methylmercapto, ethylmercapto, n-propylmercapto, 1-methylethylmercapto (isopropylmercapto), n-butylmercapto, iso-butylmercapto, sec-butylmercapto, tert-butylmercapto, and the like.

As used herein, "alkenyl" refers to a straight or branched hydrocarbon chain containing one or more double bonds. The alkenyl group may have 2 to 20 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 4 carbon atoms. The alkenyl group may be designated as "$C_{2-4}$ alkenyl" or similar designations. By way of example only, "$C_{2-4}$ alkenyl" indicates that there are two to four carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2,-dienyl, and buta-1,2-dien-4-yl. Typical alkenyl groups include, but are in no way limited to, ethenyl, propenyl, butenyl, pentenyl, and hexenyl, and the like.

As used herein, "alkynyl" refers to a straight or branched hydrocarbon chain containing one or more triple bonds. The alkynyl group may have 2 to 20 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 4 carbon atoms. The alkynyl group may be designated as "$C_{2-4}$ alkynyl" or similar designations. By way of example only, "$C_{2-4}$ alkynyl" indicates that there are two to four carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like.

As used herein, "heteroalkyl" refers to a straight or branched hydrocarbon chain containing one or more heteroatoms, that is, an element other than carbon, including but not limited to, nitrogen, oxygen and sulfur, in the chain backbone. The heteroalkyl group may have 1 to 20 carbon atom, although the present definition also covers the occurrence of the term "heteroalkyl" where no numerical range is designated. The heteroalkyl group may also be a medium size heteroalkyl having 1 to 9 carbon atoms. The heteroalkyl group could also be a lower heteroalkyl having 1 to 4 carbon atoms. The heteroalkyl group may be designated as "$C_{1-4}$ heteroalkyl" or similar designations. The heteroalkyl group may contain one or more heteroatoms. By way of example only, "$C_{1-4}$ heteroalkyl" indicates that there are one to four carbon atoms in the heteroalkyl chain and additionally one or more heteroatoms in the backbone of the chain.

As used herein, "alkylene" means a branched, or straight chain fully saturated di-radical chemical group containing only carbon and hydrogen that is attached to the rest of the molecule via two points of attachment (i.e., an alkanediyl). The alkylene group may have 1 to 20 carbon atoms, although the present definition also covers the occurrence of the term alkylene where no numerical range is designated. The alkylene group may also be a medium size alkylene having 1 to 9 carbon atoms. The alkylene group could also be a lower alkylene having 1 to 4 carbon atoms. The alkylene group may be designated as "$C_{1-4}$ alkylene" or similar designations. By way of example only, "$C_{1-4}$ alkylene" indicates that there are one to four carbon atoms in the alkylene chain, i.e., the alkylene chain is selected from the group consisting of methylene, ethylene, ethan-1,1-diyl, propylene, propan-1,1-diyl, propan-2,2-diyl, 1-methyl-ethylene, butylene, butan-1,1-diyl, butan-2,2-diyl, 2-methyl-propan-1,1-diyl, 1-methyl-propylene, 2-methyl-propylene, 1,1-dimethyl-ethylene, 1,2-dimethyl-ethylene, and 1-ethyl-ethylene.

As used herein, "alkenylene" means a straight or branched chain di-radical chemical group containing only carbon and hydrogen and containing at least one carbon-carbon double bond that is attached to the rest of the molecule via two points of attachment. The alkenylene group may have 2 to 20 carbon atoms, although the present definition also covers the occurrence of the term alkenylene where no numerical range is designated. The alkenylene group may also be a medium size alkenylene having 2 to 9 carbon atoms. The alkenylene group could also be a lower alkenylene having 2 to 4 carbon atoms. The alkenylene group may be designated as "$C_{2-4}$ alkenylene" or similar designations. By way of example only, "$C_{2-4}$ alkenylene" indicates that there are two to four carbon atoms in the alkenylene chain, i.e., the alkenylene chain is selected from the group consisting of ethenylene, ethen-1,1-diyl, propenylene, propen-1,1-diyl, prop-2-en-1,1-diyl, 1-methyl-ethenylene, but-1-enylene, but-2-enylene, but-1,3-dienylene, buten-1,1-diyl, but-1,3-dien-1,1-diyl, but-2-en-1,1-diyl, but-3-en-1,1-diyl, 1-methyl-prop-2-en-1,1-diyl, 2-methyl-prop-2-en-1,1-diyl, 1-ethyl-ethenylene, 1,2-dimethyl-ethenylene, 1-methyl-propenylene, 2-methyl-propenylene, 3-methyl-propenylene, 2-methyl-propen-1,1-diyl, and 2,2-dimethyl-ethen-1,1-diyl.

The term "aromatic" refers to a ring or ring system having a conjugated pi electron system and includes both carbocyclic aromatic (e.g., phenyl) and heterocyclic aromatic groups (e.g., pyridine). The term includes monocyclic or fused-ring polycyclic (i.e., rings which share adjacent pairs of atoms) groups provided that the entire ring system is aromatic.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some embodiments, the aryl group has 6 to 10 carbon atoms.

The aryl group may be designated as "$C_{6-10}$ aryl," "$C_6$ or $C_{10}$ aryl," or similar designations. Examples of aryl groups include, but are not limited to, phenyl, naphthyl, azulenyl, and anthracenyl.

As used herein, "aryloxy" and "arylthio" refers to RO— and RS—, in which R is an aryl as is defined above, such as "$C_{6-10}$ aryloxy" or "$C_{6-10}$ arylthio" and the like, including but not limited to phenyloxy.

An "aralkyl" or "arylalkyl" is an aryl group connected, as a substituent, via an alkylene group, such as "$C_{7-14}$ aralkyl" and the like, including but not limited to benzyl, 2-phenylethyl, 3-phenylpropyl, and naphthylalkyl. In some cases, the alkylene group is a lower alkylene group (i.e., a $C_{1-4}$ alkylene group).

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-7 membered heteroaryl," "5-10 membered heteroaryl," or similar designations. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl.

A "heteroaralkyl" or "heteroarylalkyl" is heteroaryl group connected, as a substituent, via an alkylene group. Examples include but are not limited to 2-thienylmethyl, 3-thienylmethyl, furylmethyl, thienylethyl, pyrrolylalkyl, pyridylalkyl, isoxazollylalkyl, and imidazolylalkyl. In some cases, the alkylene group is a lower alkylene group (i.e., a $C_{1-4}$ alkylene group).

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation provided that at least one ring in a ring system is not aromatic. Thus, carbocyclyls include cycloalkyls, cycloalkenyls, and cycloalkynyls. The carbocyclyl group may have 3 to 20 carbon atoms, although the present definition also covers the occurrence of the term "carbocyclyl" where no numerical range is designated. The carbocyclyl group may also be a medium size carbocyclyl having 3 to 10 carbon atoms. The carbocyclyl group could also be a carbocyclyl having 3 to 6 carbon atoms. The carbocyclyl group may be designated as "$C_{3-6}$ carbocyclyl" or similar designations. Examples of carbocyclyl rings include, but are not limited to, cyclopropyl, cyclobutyl, cyclopentyl, cyclohexyl, cyclohexenyl, 2,3-dihydro-indene, bicycle[2.2.2]octanyl, adamantyl, and spiro[4.4]nonanyl.

A "(carbocyclyl)alkyl" is a carbocyclyl group connected, as a substituent, via an alkylene group, such as "$C_{4-10}$ (carbocyclyl)alkyl" and the like, including but not limited to, cyclopropylmethyl, cyclobutylmethyl, cyclopropylethyl, cyclopropylbutyl, cyclobutylethyl, cyclopropylisopropyl, cyclopentylmethyl, cyclopentylethyl, cyclohexylmethyl, cyclohexylethyl, cycloheptylmethyl, and the like. In some cases, the alkylene group is a lower alkylene group.

As used herein, "cycloalkyl" means a fully saturated carbocyclyl ring or ring system. Examples include cyclopropyl, cyclobutyl, cyclopentyl, and cyclohexyl.

As used herein, "cycloalkenyl" means a carbocyclyl ring or ring system having at least one double bond, wherein no ring in the ring system is aromatic. An example is cyclohexenyl.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations. In preferred six membered monocyclic heterocyclyls, the heteroatom(s) are selected from one up to three of O, N or S, and in preferred five membered monocyclic heterocyclyls, the heteroatom(s) are selected from one or two heteroatoms selected from O, N, or S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

A "(heterocyclyl)alkyl" is a heterocyclyl group connected, as a substituent, via an alkylene group. Examples include, but are not limited to, imidazolinylmethyl and indolinylethyl.

As used herein, "acyl" refers to —C(=O)R, wherein R is hydrogen, hydrogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, optionally substituted (5 to 10 membered heterocyclyl)-$C_1$-$C_6$ alkyl, as defined herein. Non-limiting examples include formyl, acetyl, propanoyl, benzoyl, and acryl.

An "O-carboxy" group refers to a "—OC(=O)R" group in which R is selected from hydrogen, hydrogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, optionally substituted (5 to 10 membered heterocyclyl)-$C_1$-$C_6$ alkyl, as defined herein.

A "C-carboxy" group refers to a "—C(=O)OR" group in which R is selected from hydrogen, hydrogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, optionally substituted (5 to 10 membered heterocyclyl)-$C_1$-$C_6$ alkyl, as defined herein. A non-limiting example includes carboxyl (i.e., —C(=O)OH).

A "cyano" group refers to a "—CN" group.

A "cyanato" group refers to an "—OCN" group.

An "isocyanato" group refers to a "—NCO" group.

A "thiocyanato" group refers to a "—SCN" group.

An "isothiocyanato" group refers to an "—NCS" group.

A "sulfinyl" group refers to an "—S(=O)R" group in which R is selected from hydrogen, hydrogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, optionally substituted (5 to 10 membered heterocyclyl)-$C_1$-$C_6$ alkyl, as defined herein.

A "sulfonyl" group refers to an "—SO$_2$R" group in which R is selected from hydrogen, hydrogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, optionally substituted (5 to 10 membered heterocyclyl)-$C_1$-$C_6$ alkyl, as defined herein.

An "S-sulfonamido" group refers to a "—SO$_2$NR$_A$R$_B$" group in which R$_A$ and R$_B$ are each independently selected from hydrogen, hydrogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, optionally substituted (5 to 10 membered heterocyclyl)-$C_1$-$C_6$ alkyl, as defined herein.

An "N-sulfonamido" group refers to a "—N(R$_A$)SO$_2$R$_B$" group in which R$_A$ and R$_b$ are each independently selected from hydrogen, hydrogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, optionally substituted (5 to 10 membered heterocyclyl)-$C_1$-$C_6$ alkyl, as defined herein.

An "O-carbamyl" group refers to a "—OC(=O)NR$_A$R$_B$" group in which R$_A$ and R$_B$ are each independently selected from hydrogen, hydrogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, optionally substituted (5 to 10 membered heterocyclyl)-$C_1$-$C_6$ alkyl, as defined herein.

An "N-carbamyl" group refers to an "—N(R$_A$)OC(=O)R$_B$" group in which R$_A$ and R$_B$ are each independently selected from hydrogen, hydrogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, optionally substituted (5 to 10 membered heterocyclyl)-$C_1$-$C_6$ alkyl, as defined herein.

An "O-thiocarbamyl" group refers to a "—OC(=S)NR$_A$R$_B$" group in which R$_A$ and R$_B$ are each independently selected from hydrogen, hydrogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, optionally substituted (5 to 10 membered heterocyclyl)-$C_1$-$C_6$ alkyl, as defined herein.

An "N-thiocarbamyl" group refers to an "—N(R$_A$)OC(=S)R$_B$" group in which R$_A$ and R$_B$ are each independently selected from hydrogen, hydrogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, optionally substituted (5 to 10 membered heterocyclyl)-$C_1$-$C_6$ alkyl, as defined herein.

A "C-amido" group refers to a "—C(=O)NR$_A$R$_B$" group in which R$_A$ and R$_B$ are each independently selected from hydrogen, hydrogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, optionally substituted (5 to 10 membered heterocyclyl)-$C_1$-$C_6$ alkyl, as defined herein.

An "N-amido" group refers to a "—N(R$_A$)C(=O)R$_B$" group in which R$_A$ and R$_B$ are each independently selected from hydrogen, hydrogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, or optionally substituted (5 to 10 membered heterocyclyl)-$C_1$-$C_6$ alkyl, as defined herein.

An "amino" group refers to a "—$NR_AR_B$" group in which $R_A$ and $R_B$ are each independently selected from hydrogen, hydrogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, optionally substituted (5 to 10 membered heterocyclyl)-$C_1$-$C_6$ alkyl, or a suitable amine protecting group, as defined herein. A non-limiting example includes free amino (i.e., —$NH_2$).

An "amide" or "amido" group refers to a "—NR—C(=O)—R group in which each R is independently selected from hydrogen, hydrogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, optionally substituted (5 to 10 membered heterocyclyl)-$C_1$-$C_6$ alkyl, or a suitable amine protecting group, as defined herein.

An "aminoalkyl" group refers to an amino group connected via an alkylene group.

An "alkoxyalkyl" group refers to an alkoxy group connected via an alkylene group, such as a "$C_{2-8}$ alkoxyalkyl" and the like.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from $C_1$-$C_{24}$ alkyl, $C_1$-$C_{24}$ alkenyl, $C_1$-$C_{24}$ alkynyl, $C_1$-$C_{24}$ heteroalkyl, $C_3$-$C_{10}$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, $C_1$-$C_6$ alkoxy($C_1$-$C_6$)alkyl (i.e., ether), aryloxy, sulfhydryl (mercapto), halo($C_1$-$C_6$) alkyl (e.g., —$CF_3$), halo($C_1$-$C_6$)alkoxy (e.g., —$OCF_3$), $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, amido, S-sulfonamido, N-sulfonamido, C-carboxy, O-carboxy, acyl, cyanato, isocyanato, thiocyanato, isothiocyanato, sulfinyl, sulfonyl, and oxo (=O). Wherever a group is described as "optionally substituted" that group can be substituted with the above substituents.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —$CH_2$—, —$CH_2CH_2$—, —$CH_2CH(CH_3)CH_2$—, and the like. Other radical naming conventions clearly indicate that the radical is a di-radical such as "alkylene" or "alkenylene."

When two R groups are said to form a ring (e.g., a carbocyclyl, heterocyclyl, aryl, or heteroaryl ring) "together with the atom to which they are attached," it is meant that the collective unit of the atom and the two R groups are the recited ring. The ring is not otherwise limited by the definition of each R group when taken individually. For example, when the following substructure is present:

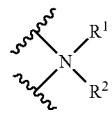

and $R^1$ and $R^2$ are defined as selected from the group consisting of hydrogen and alkyl, or $R^1$ and $R^2$ together with the nitrogen to which they are attached form a heterocyclyl, it is meant that $R^1$ and $R^2$ can be selected from hydrogen or alkyl, or alternatively, the substructure has structure:

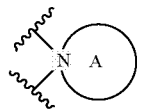

where ring A is a heteroaryl ring containing the depicted nitrogen.

Similarly, when two "adjacent" R groups are said to form a ring "together with the atom to which they are attached," it is meant that the collective unit of the atoms, intervening bonds, and the two R groups are the recited ring. For example, when the following substructure is present:

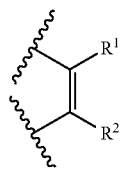

and $R^1$ and $R^2$ are defined as selected from the group consisting of hydrogen and alkyl, or $R^1$ and $R^2$ together with the atoms to which they are attached form an aryl or carbocylyl, it is meant that $R^1$ and $R^2$ can be selected from hydrogen or alkyl, or alternatively, the substructure has structure:

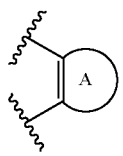

where A is an aryl ring or a carbocylyl containing the depicted double bond.

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

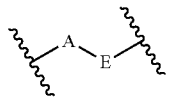

includes the substituent being oriented such that the A is attached at the leftmost attachment point of the molecule as well as the case in which A is attached at the rightmost attachment point of the molecule.

Where the compounds disclosed herein have at least one chiral center, they may exist as individual enantiomers and diastereomers or as mixtures of such isomers, including racemates. Separation of the individual isomers or selective synthesis of the individual isomers is accomplished by application of various methods which are well known to practitioners in the art. Unless otherwise indicated, all such isomers and mixtures thereof are included in the scope of the compounds disclosed herein. Furthermore, compounds disclosed herein may exist in one or more crystalline or amorphous forms. Unless otherwise indicated, all such forms are included in the scope of the compounds disclosed herein including any polymorphic forms. In addition, some of the compounds disclosed herein may form solvates with water (i.e., hydrates) or common organic solvents. Unless otherwise indicated, such solvates are included in the scope of the compounds disclosed herein.

The skilled artisan will recognize that some structures described herein may be resonance forms or tautomers of compounds that may be fairly represented by other chemical structures, even when kinetically; the artisan recognizes that such structures may only represent a very small portion of a sample of such compound(s). Such compounds are considered within the scope of the structures depicted, though such resonance forms or tautomers are not represented herein.

Isotopes may be present in the compounds described. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

Unless otherwise defined, all technical and scientific terms used herein have the same meaning as commonly understood by one of ordinary skill in the art to which these embodiments belong. The terminology used in the description herein is for describing particular embodiments only and is not intended to be limiting of the embodiments. As used in the specification and the appended claims, the singular forms "a," "an," and "the" are intended to include the plural forms as well, unless the context clearly indicates otherwise. All publications, patent applications, patents, and other references mentioned herein are incorporated by reference in their entirety.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' preferred,"desired," or 'desirable,' and words of similar meaning should not be understood as implying that certain features are critical, essential, or even important to the structure or function of the invention, but instead as merely intended to highlight alternative or additional features that may or may not be utilized in a particular embodiment. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present embodiments. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the embodiments are approximations, the numerical values set forth in the specific examples are reported as precisely as possible. Any numerical value, however, inherently contains certain errors necessarily resulting from the standard deviation found in their respective testing measurements. Every numerical range given throughout this specification and claims will include every narrower numerical range that falls within such broader numerical range, as if such narrower numerical ranges were all expressly written herein. Where a range of values is provided, it is understood that the upper and lower limit, and each intervening value between the upper and lower limit of the range is encompassed within the embodiments.

CSA Compound Synthesis:

The methods disclosed herein may be as described below, or by modification of these methods. Ways of modifying the methodology include, among others, temperature, solvent, reagents etc., known to those skilled in the art. In general, during any of the processes for preparation disclosed herein, it may be necessary and/or desirable to protect sensitive or reactive groups on any of the molecules concerned. This may be achieved by means of conventional protecting groups, such as those described in *Protective Groups in Organic Chemistry* (ed. J. F. W. McOmie, Plenum Press, 1973); and P. G. M. Green, T. W. Wutts, *Protecting Groups in Organic Synthesis* (3rd ed.) Wiley, New York (1999), which are both hereby incorporated herein by reference in their entirety. The protecting groups may be removed at a convenient subsequent stage using methods known from the art. Synthetic chemistry transformations useful in synthesizing applicable compounds are known in the art and include e.g. those described in R. Larock, Comprehensive Organic Transformations, VCH Publishers, 1989, or L. Paquette, ed., *Encyclopedia of Reagents for Organic Synthesis*, John Wiley and Sons, 1995, which are both hereby incorporated herein by reference in their entirety. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

An exemplary but non-limiting general synthetic scheme for preparing a compound of Formula (I) is shown in Scheme A-1, below. Unless otherwise indicated, the variable definitions are as above for Formula (I). This process starts with a cholic acid (1). Treatment of (1) with secondary amine $R_1R_2NH$ under amide bond forming conditions affords intermediate (2). Amide bond forming reagents include, but are not limited to, EDAC [N-(3-Dimethylaminopropyl)-N'-ethylcarbodiimide hydrochloride] in the presence of HOBT (I-hydroxybenzotriazole), or HATU [N,N,N',N'-Tetramethyl-O-(7-azabenzotriazol-1-yl)uronium hexafluorophosphate) in the presence of diisopropylethylamine, and the like.

In some embodiments, $R_1$ and $R_2$ are independently selected from the group consisting of hydrogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, optionally substituted (5 to 10 membered heterocyclyl)-$C_1$-$C_6$ alkyl, and a suitable amine protecting group, provided that at least one of $R_1$ or $R_2$ is not a hydrogen.

Compound (2) can then be subjected to reducing conditions to afford the amine derivative (3). In some embodiments, suitable reducing agents include, but are not limited to, RedAl, lithium aluminum hydride, lithium borohydride, or treatment with hydrogen in the presence of a suitable metal catalyst or treatment with silyl hydrides in the presence of a suitable metal catalyst. Suitable metal catalysts are known in the art. In some embodiments, this step can be omitted.

Compound (3) is subsequently optionally protected with a suitable amine protecting group to provide Compound (4).

Compound (4) is then treated with

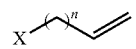

in the presence of a base to afford a compound of Formula (5). In some embodiments, X is a leaving group. In some embodiments, X is halogen. In some embodiments, X is a sulfonate. In some embodiments, n is an integer between 1 and 25. In some embodiments, n is an integer between 1 and 10. In some embodiments, n is 2, 3, or 4.

Compound (5) is then treated with a boron-containing reagent and subsequently subjected to oxidizing conditions. Suitable boron reagents and oxidizing conditions are known in the art, and include, but are not limited to, THF-borane, dimethylsulfide borane, disiamylborane, 9-BBN, pinacol borane, pyridine borane, catechol borane, molecular oxygen, hydrogen peroxide, water, Oxone®, ozone, and sodium perborate.

The oxidized intermediate is then treated with a sulfonating reagent $R_3$—$SO_2Cl$ to provide Compound (6). In some embodiments, $R_3$ is selected from the group consisting of optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, and optionally substituted (5 to 10 membered heterocyclyl)-$C_1$-$C_6$ alkyl.

Compound (6) is then treated with $R_4R_5NH$ and is optionally deprotected to afford compounds of Formula (I). In some embodiments $R_4$ and $R_5$ are independently selected from the group consisting of hydrogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, optionally substituted (5 to 10 membered heterocyclyl)-$C_1$-$C_6$ alkyl, and a suitable amine protecting group.

Scheme A-1
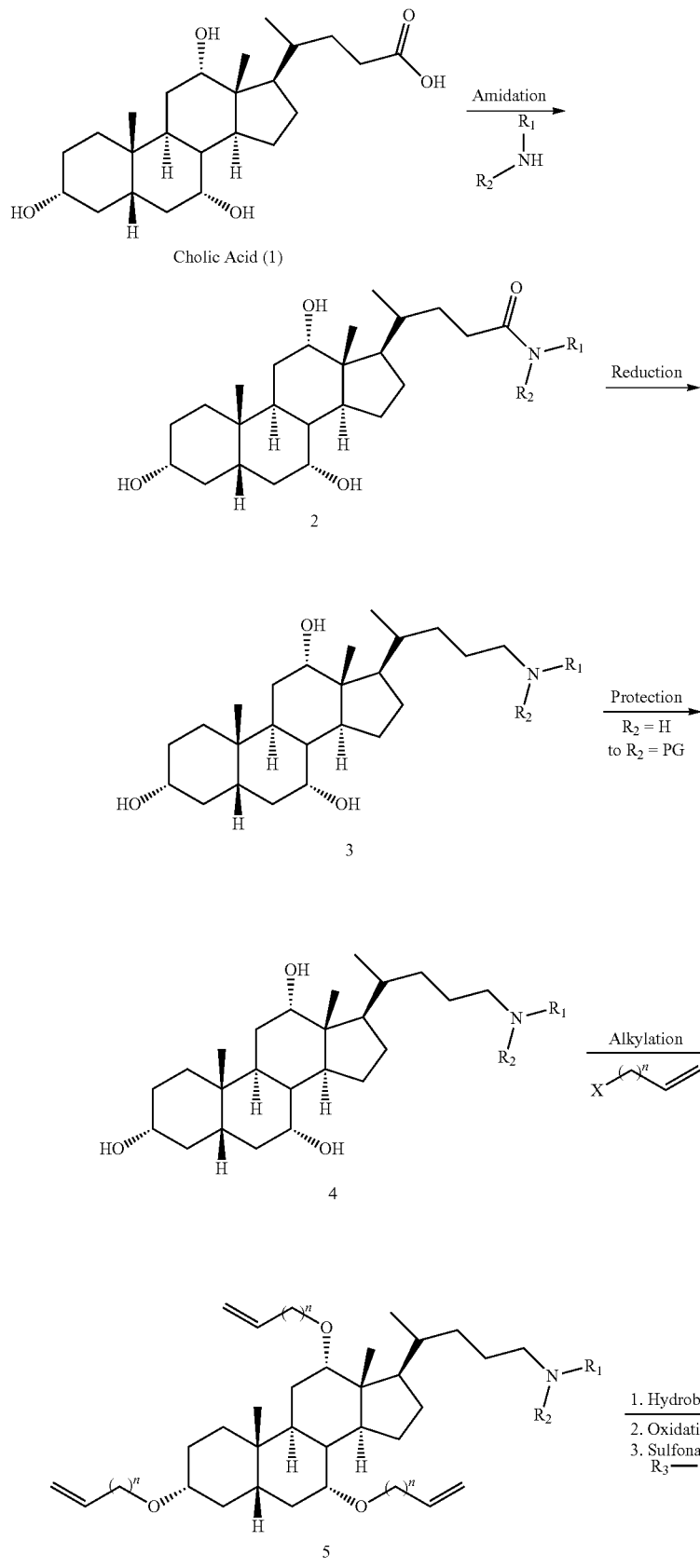

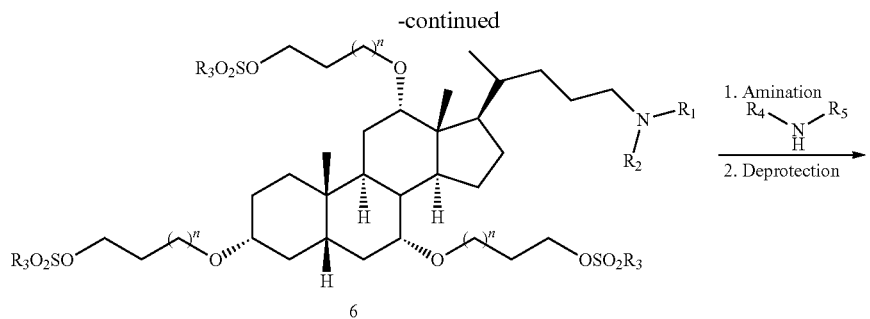

6

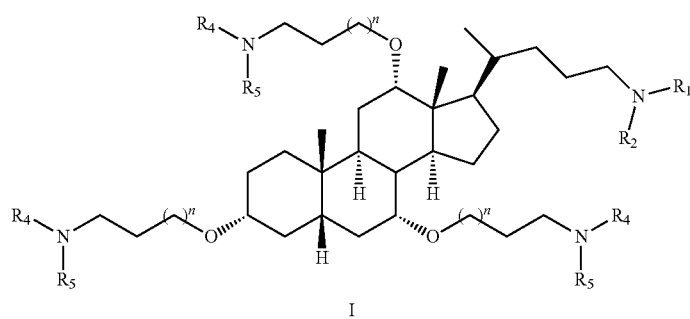

I

In some embodiments, production of a compound of Formula (III) can proceed according to Scheme A-2, shown below. Scheme A-2 can proceed as in Scheme A-1, with the exception that compound (2) is not converted to an amine derivative compound (3). Instead, compound (2) is subsequently optionally protected with a suitable amine protecting group to provide Compound (10).

Compound (10) is then treated with

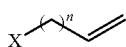

in the presence of a base to afford a compound of Formula (11). In some embodiments, X is a leaving group. In some embodiments, X is halogen. In some embodiments, X is a sulfonate. In some embodiments, n is an integer between 1 and 25. In some embodiments, n is an integer between 1 and 10. In some embodiments, n is 2, 3, or 4.

Compound (11) is then treated with a boron-containing reagent and subsequently subjected to oxidizing conditions. Suitable boron reagents and oxidizing conditions are known in the art, and include, but are not limited to, THF-borane, dimethylsulfide borane, disiamylborane, 9-BBN, pinacol borane, pyridine borane, catechol borane, molecular oxygen, hydrogen peroxide, water, Oxone®, ozone, and sodium perborate.

The oxidized intermediate is then treated with a sulfonating reagent $R_3$—$SO_2Cl$ to provide Compound (12). In some embodiments, $R_3$ is selected from the group consisting of optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, and optionally substituted (5 to 10 membered heterocyclyl)-$C_1$-$C_6$ alkyl.

Compound (12) is then treated with $R_4R_5NH$ and is optionally deprotected to afford compounds of Formula (III). In some embodiments $R_4$ and $R_5$ are independently selected from the group consisting of hydrogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, optionally substituted (5 to 10 membered heterocyclyl)-$C_1$-$C_6$ alkyl, and a suitable amine protecting group.

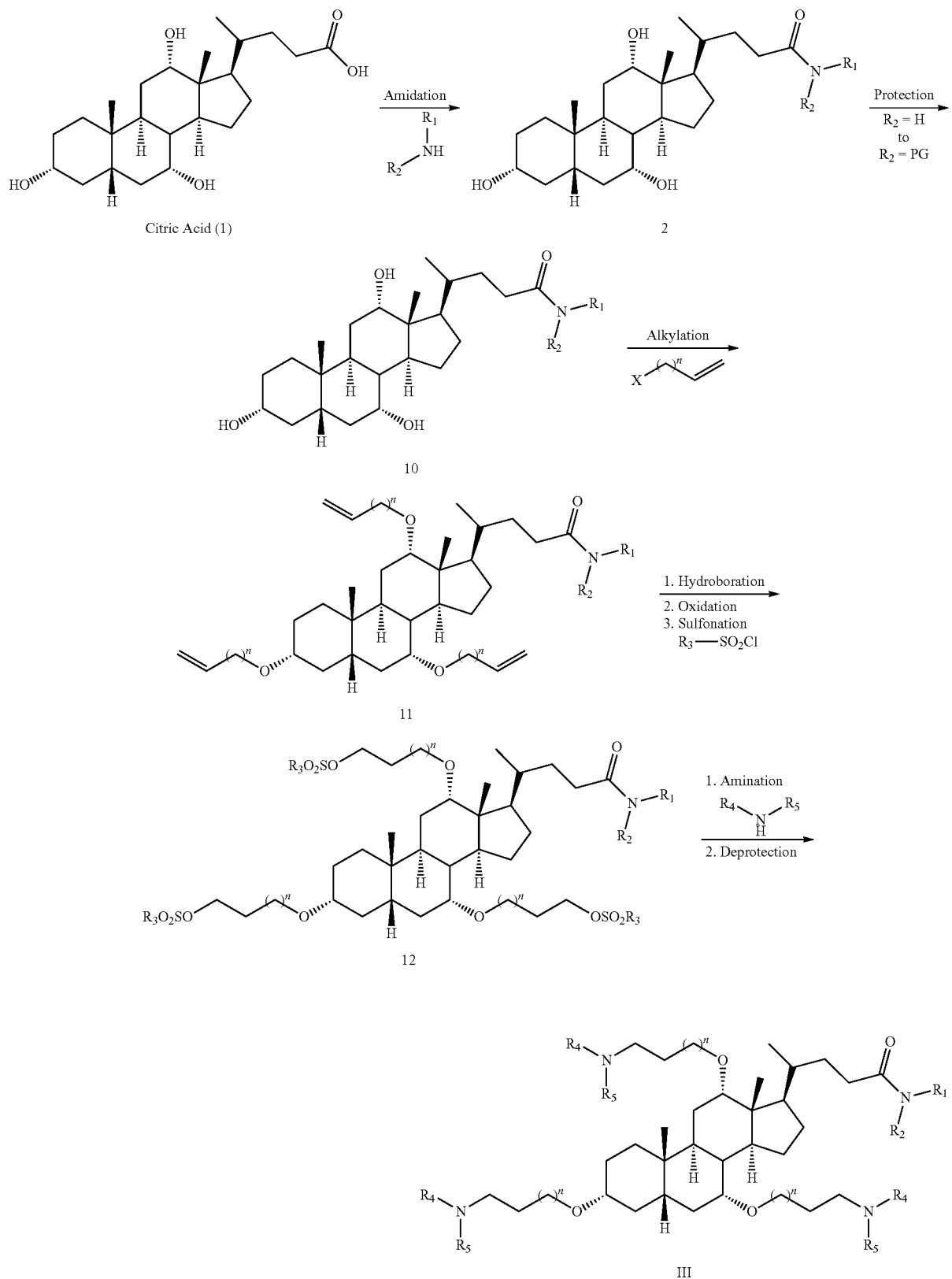

An exemplary but non-limiting general synthetic scheme for preparing a compound of Formula (II) is shown in Scheme B-1, below. Unless otherwise indicated, the variable definitions are as above for Formula (I). In some embodiments, Compound (2) is treated with

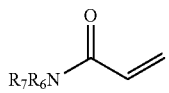

to afford a compound of Formula (8). In some embodiments $R_6$ and $R_7$ are independently selected from the group consisting of hydrogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, optionally substituted (5 to 10 membered heterocyclyl)-$C_1$-$C_6$ alkyl, and a suitable amine protecting group. Compound (8) is then subjected to reducing conditions and optionally deprotected to afford a compound of Formula (II).

In some embodiments, Step 1 in Scheme B-1 is optionally performed in the presence of a phase transfer catalyst. Suitable phase transfer catalysts include, but are not limited to, tetrabutylammonium bromide and tetrabutylammonium chloride.

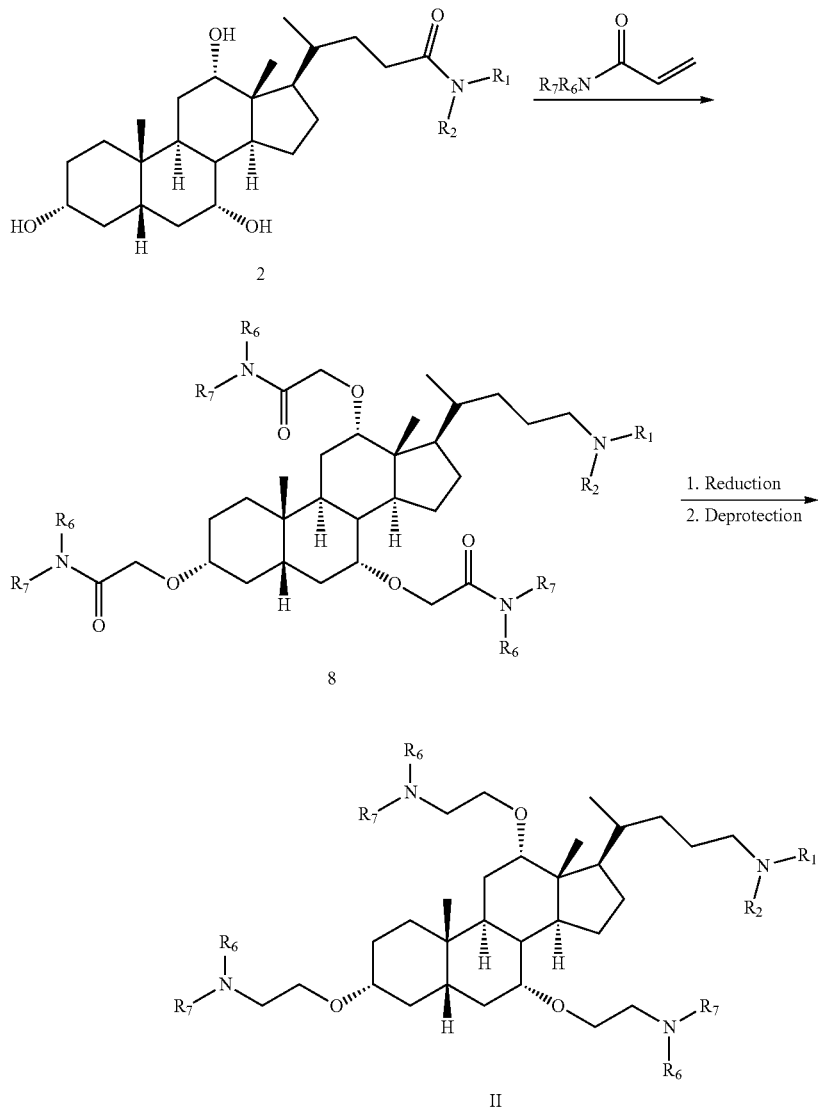

Scheme B-1

In some embodiments, production of a compound of Formula (IV) can proceed according to Scheme B-2, shown below. Scheme B-2 can proceed as in Scheme B-1, with the exception that compound (2) is not converted to an amine derivative compound (8). Instead, compound (2) is treated with

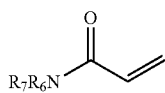

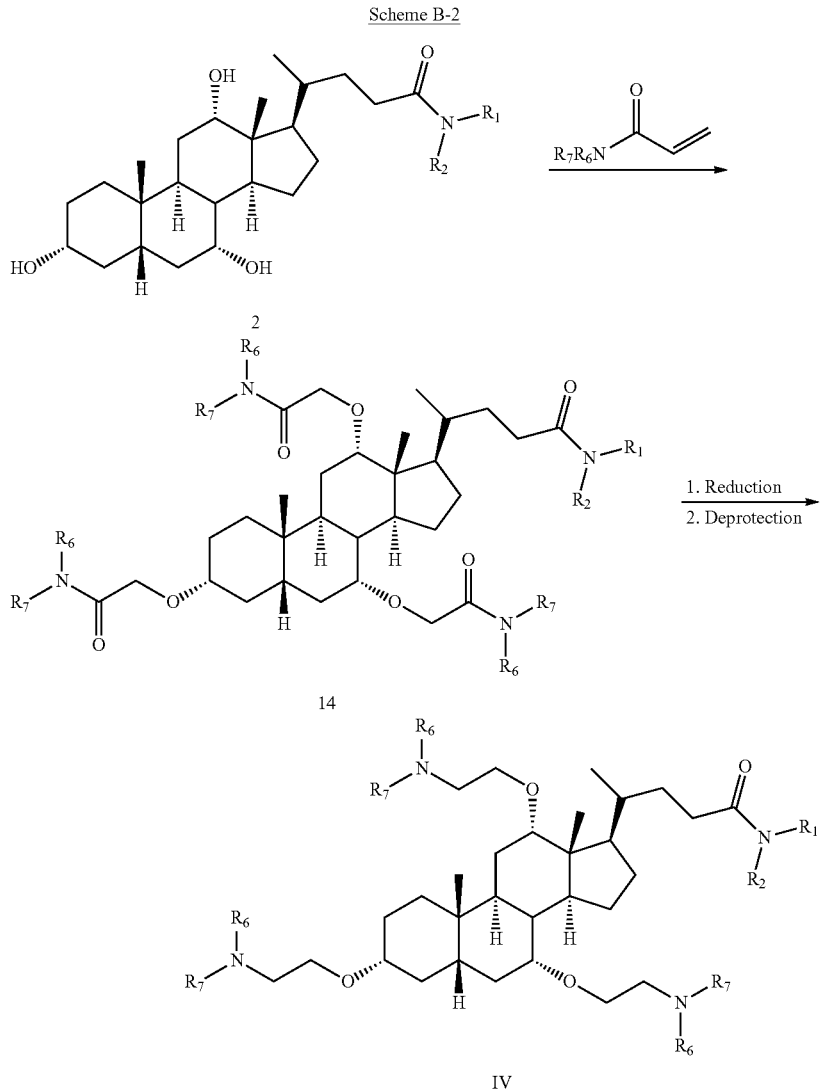

In some embodiments, Step 1 in Scheme B-2 is optionally performed in the presence of a phase transfer catalyst. Suitable phase transfer catalysts include, but are not limited to, tetrabutylammonium bromide and tetrabutylammonium chloride.

to afford a compound of Formula (14). In some embodiments $R_6$ and $R_7$ are independently selected from the group consisting of hydrogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, optionally substituted (5 to 10 membered heterocyclyl)-$C_1$-$C_6$ alkyl, and a suitable amine protecting group. Compound (8) is then subjected to reducing conditions and optionally deprotected to afford a compound of Formula (II).

An exemplary but non-limiting general synthetic scheme for preparing a compound of Formula (I) from a Compound of Formula (5) is shown in Scheme C-1, below. Unless otherwise indicated, the variable definitions are as above for Formulas (5) and (I). In some embodiments, Compound (5) is treated with a boron-containing reagent following by treatment with $R_4R_5N$—$OR_8$ in the presence of a suitable metal catalyst, followed by optional deprotection to afford compounds of Formula (I). Suitable metal catalysts include, but are not limited to, copper catalysts, palladium catalysts, rhodium catalysts, and gold catalysts.

$R_4$ and $R_5$ are independently selected from the group consisting of hydrogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, optionally substituted (5 to 10 membered heterocyclyl)-$C_1$-$C_6$ alkyl, and a suitable amine protecting group.

$R_8$ is selected from the group consisting of hydrogen, halogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, and optionally substituted (5 to 10 membered heterocyclyl)-$C_1$-$C_6$ alkyl.

In some embodiments, suitable metals for the metal catalyst include, but are not limited to, scandium, titanium, vanadium, iron, nickel, copper, ruthenium, rhodium, palladium, silver, rhenium, osmium, iridium, platinum, and gold. Suitable ligands for the metal catalyst are known in the art.

$R_4$ and $R_5$ are independently selected from the group consisting of hydrogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, optionally substituted (5 to 10 membered heterocyclyl)-$C_1$-$C_6$ alkyl, and a suitable amine protecting group.

$R_8$ is selected from the group consisting of hydrogen, halogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, and optionally substituted (5 to 10 membered heterocyclyl)-$C_1$-$C_6$ alkyl.

In some embodiments, suitable metals for the metal catalyst include, but are not limited to, scandium, titanium, vanadium, iron, nickel, copper, ruthenium, rhodium, palladium, silver, rhenium, osmium, iridium, platinum, and gold. Suitable ligands for the metal catalyst are known in the art.

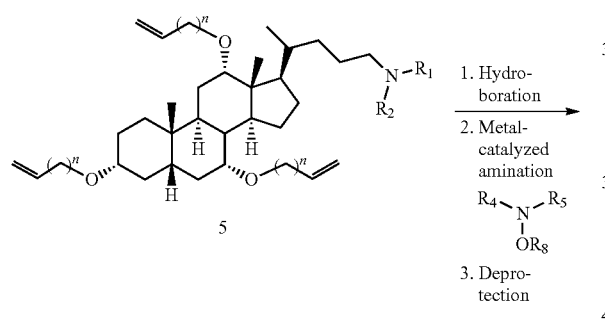

Scheme C-1

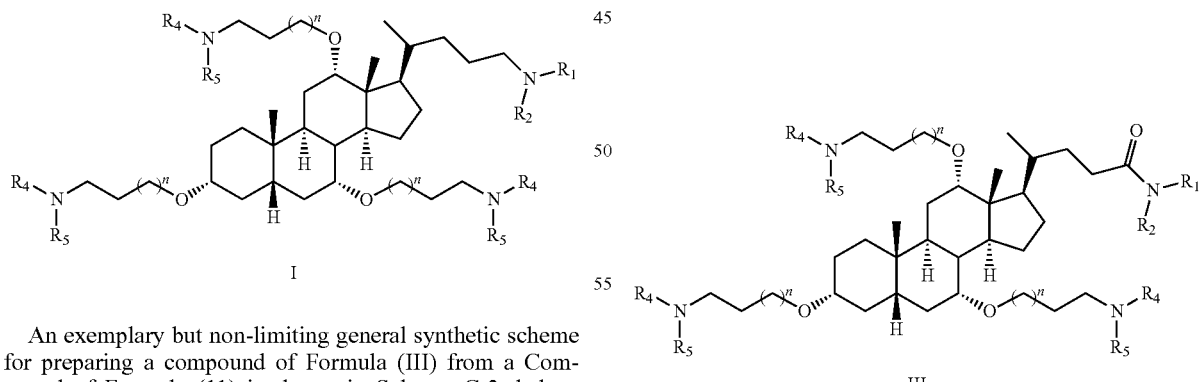

Scheme C-2

An exemplary but non-limiting general synthetic scheme for preparing a compound of Formula (III) from a Compound of Formula (11) is shown in Scheme C-2, below. Unless otherwise indicated, the variable definitions are as above for Formulas (11) and (III). In some embodiments, Compound (11) is treated with a boron-containing reagent following by treatment with $R_4R_5N$—$OR_8$ in the presence of a suitable metal catalyst, followed by optional deprotection to afford compounds of Formula (III). Suitable metal catalysts include, but are not limited to, copper catalysts, palladium catalysts, rhodium catalysts, and gold catalysts.

EXAMPLES

Additional embodiments are disclosed in further detail in the following examples, which are not in any way intended to limit the scope of the claims.

Example 1

Preparation of CSA-54

Step 1: Preparation of Octylamide 47

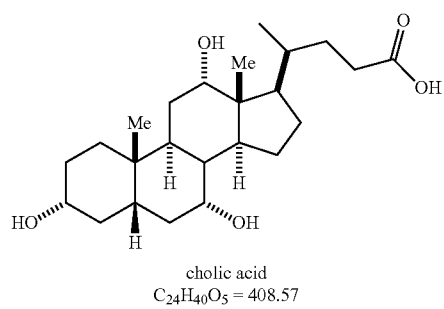

cholic acid
$C_{24}H_{40}O_5 = 408.57$

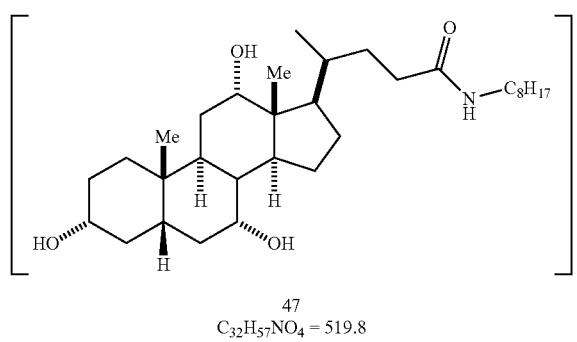

47
$C_{32}H_{57}NO_4 = 519.8$

Step 2: Preparation of Octylamine 48

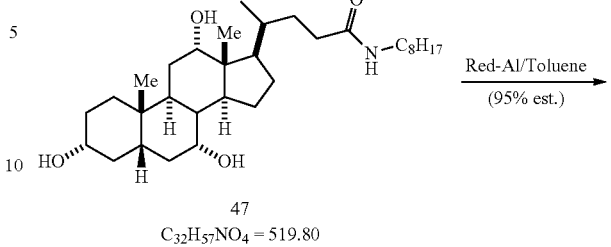

47
$C_{32}H_{57}NO_4 = 519.80$

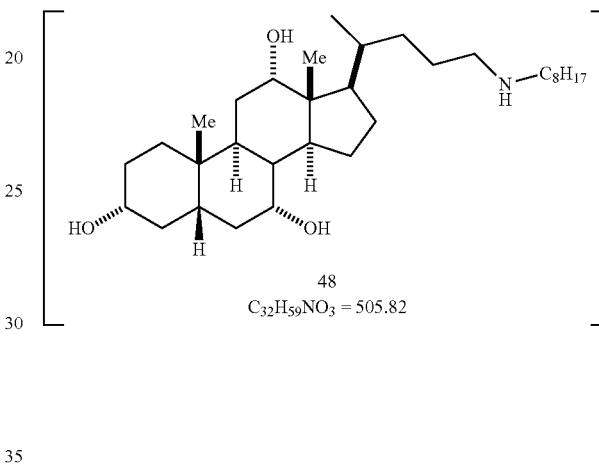

48
$C_{32}H_{59}NO_3 = 505.82$

To a 5 L Round Bottom Flask equipped with an overhead mechanical stirrer, addition funnel, thermocouple and inert gas inlet was charged cholic acid (181.7 g, 445 mmole, 1.0 eq), HOBt (3.00 g, 22.2 mmole, 0.05 eq.), EDCI (93.9 g, 490 mmole, 1.1 eq) and DMAc (450 mL). Agitation was begun and N-methylmorpholine (113 g, 1.113 mole, 2.5 eq.) was added, followed by n-octylamine (69.0 g, 534 mmole, 1.2 eq.), added over about 45 minutes, keeping the temperature of the reaction mixture between 15-25° C. during the addition. The reaction mixture was then stirred under nitrogen for 60-64 hours.

The mixture was then diluted with 2-MeTHF (1.59 L) and cooled to 10° C. The reaction was quenched by addition of 3M HCl (0.68 L, 170 mL of 37% HCl required) over approximately 35 minutes, keeping the temperature of the mixture below 30° C. during the addition. The mixture was stirred for an additional 15 minutes then the contents transferred to a separatory funnel and the layers allow to separate. The aqueous phase was removed and the organic layer washed with water (800 mL), 8% NaHCO₃(aq) (600 mL, prepared with 48 g NaHCO₃), dilute brine (500 mL). The mixture was diluted with toluene (500 mL) the solvent was evaporated under reduced pressure to a thick syrup (approximately 325 g). The syrup was diluted with toluene (500 mL) and the solvent was evaporated under reduced pressure to a thick syrup (Compound 47, approximately 450 g) and held for use directly in the next step without additional processing.

To a 20 L jacketed reactor equipped with an overhead mechanical stirrer, addition funnel, thermocouple and inert gas inlet was charged octyl amide 47 (100 g, 192 mmole) from a previously prepared batch as a solid. To this was transferred the octylamide 1 from the previous step (assumed to be 231 g, 444 mmole) in hot (50-60° C.) toluene (12 L) in portions until all octylamide 47 was transferred (636 mmole total). The contents were then heated to 65-75° C. to obtain a homogeneous solution. Red-Al, as a 60-65 wt. % solution in toluene (1156 g, 3.43 mole, 5.4 eq) was diluted with toluene (1.0 L) and added over 75 minutes to the amide at 65-80° C. with vigorous agitation. Once all Red-Al was added the batch was stirred at 80-85° C. until LC/MS indicated that all octylamide 47 had been consumed (about 1 hour). The reaction mixture was then cooled to ambient temperature overnight.

The reaction mixture was cooled to 10° C. and quenched by slow addition of 5% NaOH solution (60 g NaOH, 1.5 mole, in 1.2 L water). Note: an exotherm with significant off-gassing occurs. The reaction mixture was then warmed to ambient temperature and stirred for an additional 3 hours. Agitation was stopped and the layers allowed to separate. The lower aqueous layer was separated (should contain no product) and the upper organic product layer washed with 5% NaOH(aq) (1.2 L). The layers were separated and the organic product layer stirred at ambient temperature with water (2.5 L) for 10 minutes then the agitation stopped and the layers separated. The organic product layer was reduced in volume to 7 L±0.2 L by vacuum distillation and the solution of octylamine 48 was carried on directly to the next step in the synthetic sequence.

Step 3: Preparation of Cbz Protected Octylamine 49

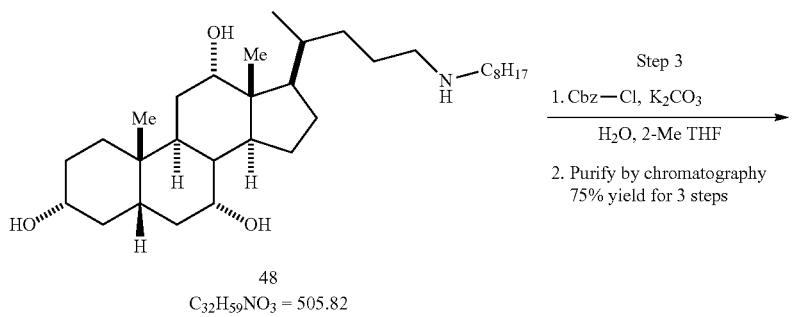

48
$C_{32}H_{59}NO_3 = 505.82$

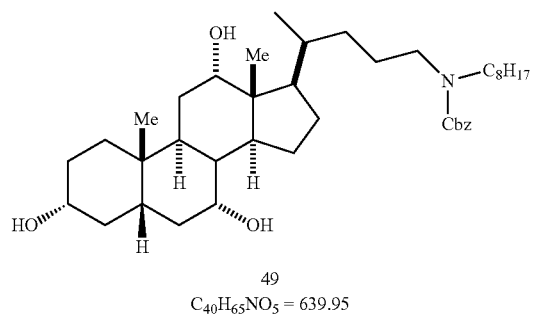

49
$C_{40}H_{65}NO_5 = 639.95$

To the toluene solution of the octylamine 48 from the previous step, was added 2-MeTHF (2.0 L) and cooled to 5-10° C. Aqueous potassium carbonate (446 gm, 3.23 moles, 5.0 eq in 2.35 L) was added and then slowly added CbzCl (114 g, 0.668 mole) added over 20 minutes at 5-10° C. The reaction was stirred overnight at 10° C. and the following morning the mixture was assayed. Octylamine 48 was still present by LC/MS analysis so additional Cbz-Cl (12.5 g, 73 mmole) was added.

After no octylamine 48 was detected by LC/MS, the reaction was quenched with NH$_4$Cl(aq) (460 g in 1.5 L water) and stirred while warming the reaction mixture to 18-25° C. The layers were separated and the organic product layer washed with 3M HCl (1 L; 250 mL 37% HCl/750 mL water), water (1.5 L), and brine (0.80 L; 285 g NaCl). The solvent was removed under reduced pressure to produce crude N-Cbz protected octylamine 49 as an orange oil.

To the crude Cbz protected octylamine 49 syrup (approximately 400 g) was charged SiO$_2$ (860 g Silicycle brand Siliflash 60, 230-400 mesh) and CH$_2$Cl$_2$ (1.5 L) to wet the silica gel and to adsorb the crude material onto the gel. The mixture was then stripped to dryness and added to the top of a flash column that had been packed with silica gel (2.8 kg) and wetted with heptane. The column was eluted with the following solvent gradients, collecting 2 L fractions: 9/1 Heptane/Ethyl acetate: 13 L (3 Column volumes; CV); 8/2 Heptane/Ethyl acetate: 3CV; 7/3 Heptane/Ethyl acetate: 3CV; 6/4 Heptane/Ethyl acetate: 3CV; 1/1 Heptane/Ethyl acetate: 3CV; 4/6 Heptane/Ethyl acetate: 3CV; 3/7 Heptane/Ethyl acetate: 3CV; 2/8 Heptane/Ethyl acetate: 3CV; EtOAc 7 CV (to the end).

The desired fractions (Rf of product: 0.45, developed with EtOAc, PMA visualization) were pooled and the solvent was removed under reduced pressure to provide 265 g of Cbz protected octylamine 49 as a white foam (65% yield from cholic acid).

Step 4: Preparation of Triallyl Derivative 50:

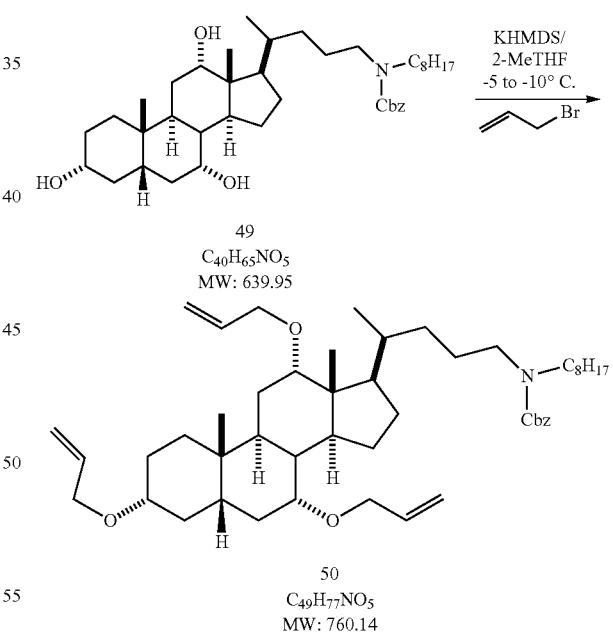

49
$C_{40}H_{65}NO_5$
MW: 639.95

50
$C_{49}H_{77}NO_5$
MW: 760.14

To a 1 L round bottom flask was charged Compound 49 (75.0 g, 119 mmole) and 2-MeTHF (500 mL). The contents of the flask were stirred to obtain a homogeneous solution then analyzed for water content (by KF). The solution of Compound 49 was transferred to the 5 L reaction flask, using additional 2-MeTHF (250 mL) to aid transfer and dilute the solution to the desired concentration. The contents of the 5 L flask were cooled to −10 to −15° C. at which point 1M KHMDS in THF (703 mL, 703 mmole) was added using an addition funnel over 35 minutes, keeping the temperature below −10° C. during the addition. The addition funnel was rinsed with 2-MeTHF (12 mL) and the allylbromide (in 2-MeTHF, 350 mL) charged to the funnel. The allyl bromide was then added drop-wise over 3 hours. When the reaction was complete, it was quenched by slow addition of 1M HCl. After stirring for 10 minutes the agitation was stopped to allow the layers to separate overnight at ambient temperature. The aqueous phase was cut away and the organic layer was washed with water (500 mL). The combined aqueous layers were back-extracted with 2-MeTHF (125 mL) and the layers separated. The combined organic layers were washed with 8% NaHCO$_3$(40 g NaHCO$_3$ in 500 mL water), brine (66 g NaCl in 250 mL water) and the organic solvent removed by distillation under vacuum to provide a thick oil (123 g). The oil was diluted with 2-MeTHF (150 mL) and distilled to provide 93.3 g of Triallyl Derivative 50 as a viscous oil (Theory: 88.9 g). HPLC purity: 91.3% (AUC).

Step 5: Preparation of Triol 51:

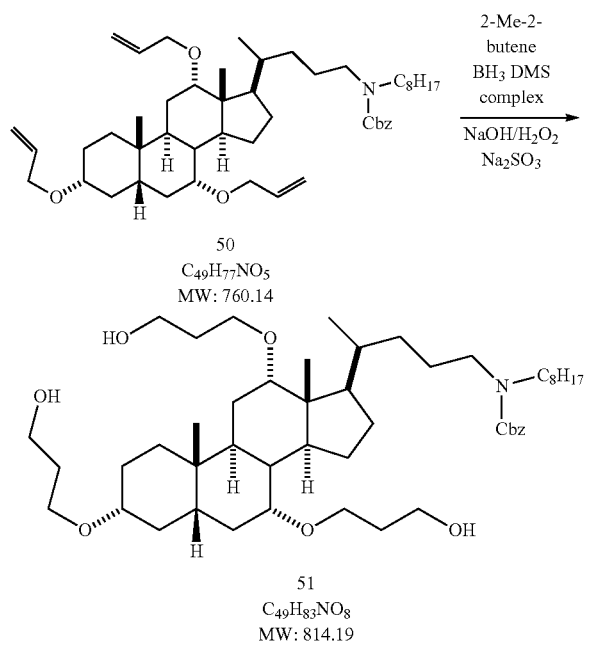

To a 5 L reaction flask was charged 2-MeTHF (850 mL) and cooled to 10° C. 2-Methyl-2-butene (246 g, 3.51 mole, 30 eq.) was added to the flask using the addition funnel, rinsing the funnel with 2-MeTHF (30 mL) which was added to the 5 L reaction flask. Borane-dimethyl sulfide complex was added using the funnel over 50 minutes at 5-15° C. and the mixture stirred at 5-15° C. for 4 hours.

Meanwhile, the triallyl 50 syrup was dissolved in 2-MeTHF (325 mL). The triallyl 50 solution was added to the 5 L reaction vessel over about 45 minutes keeping the temperature between 5-15° C. during the course of the addition. The mixture was then stirred overnight in this temperature range.

The reaction mixture was then cooled to 0-5° C. and a solution of 25% NaOH(aq) (prepared by dissolving 281 g NaOH, 7.03 mole, in 750 mL water) carefully added over about 60 minutes, keeping the temperature ≤15° C. during the course of the addition. H$_2$O$_2$ (625 mL, 7.1 mole) was then added over about 2 hours, keeping the temperature below 25° C. during the addition. After all peroxide had been added the reaction mixture was stirred for an additional 30 minutes. The reaction mixture was quenched by slow addition of Na$_2$SO$_3$ (162 g, 1.29 mole; in water 1.4 L) over 30 minutes at ≤30° C. The reaction mixture was stirred for an additional 30 minutes then agitation halted for an overnight phase period.

The phases were separated and the organic layer was washed with water (750 mL) and brine. The organic layer was then distilled to provide a viscous oil; 148 g: theory: 95.3 g. The oil was diluted with toluene (250 mL) and distilled again to a thick oil, mass: 139 g. This process (addition of toluene, 250 mL, and distillation of the batch to an oil) was repeated two more times to provide 116.5 g triol 51 as a viscous oil. The oil was diluted with MeOH (750 mL) and heated to 60-65° C. for approximately 60 minutes at which time the batch was cooled to 25-35° C. and the solvent removed by vacuum distillation. The residue was taken up in MeOH (100 mL) and the solvent removed. This procedure was repeated two more times then the oil taken up in toluene (100 mL) and stripped to provide Triol 51 as a viscous oil (111.6 g, 117% yield, HPLC purity: 87.0%). HPLC weight/weight of analysis of Triol 51 oil (compared to a purified standard) was determined to be 75% to provide a corrected yield of 83.7 g (88% from Compound 49).

Step 6: Preparation of Tritosylate 52:

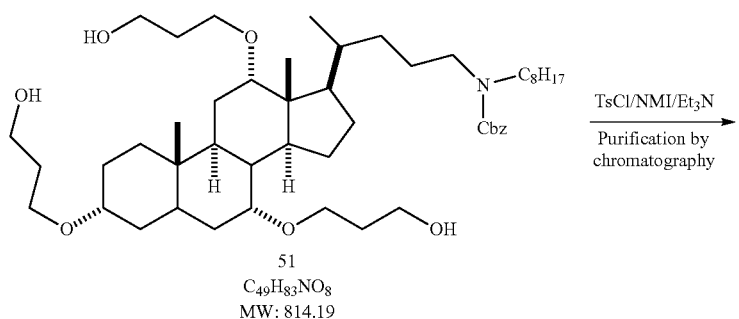

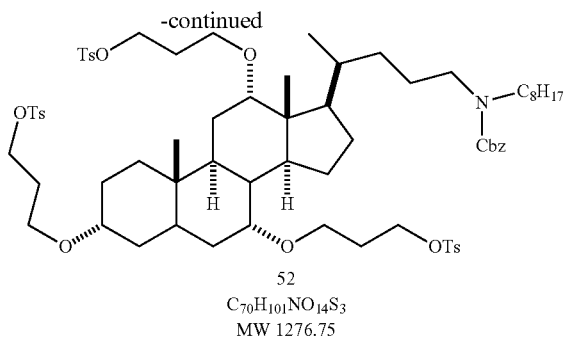

52
C$_{70}$H$_{101}$NO$_{14}$S$_3$
MW 1276.75

The crude triol 51 (95.3 g, 117 mmole) was dissolved in 2-MeTHF (750 mL) and transferred to a 5 L Reaction Vessel. The contents of the vessel were cooled to 15±2° C. and N-methylimidazole (NMI) (43.2 g, 527 mmole, 4.5 eq.) and Et$_3$N (65.1 g, 644 mmole, 5.5 eq.) added to the reaction vessel. In a separate flask, p-toluenesulfonyl chloride (156 g, 819 mmole) was dissolved in 2-MeTHF (415 mL) and transferred to the addition funnel on the 5 L Reaction Flask. The TsCl solution was added slowly over 3.25 hours, while maintaining the reaction temperature at 15-22° C. during the addition. At the end of the TsCl addition, the contents of the 5 L Reaction flask were stirred at 15±2° C. overnight (14-16 hours). Analysis of the reaction mixture indicated that the reaction was complete and the reaction mixture cooled to 5-10° C. A 2 M HCl solution was prepared (125 mL 37% HCl in water sufficient to prepare 750 mL of solution, 1.5 moles) and cooled briefly in an ice bath and slowly added to the reaction mixture in the 5 L Reaction Vessel. At the end of the addition the mixture was stirred for an additional 10-15 minutes then agitation stopped to allow for the phases to separate and the temperature to warm to approximately 15° C. The aqueous phase was cut away and back extracted with 2-MeTHF (200 mL). The combined organic layers were then cooled to 5-10° C. and stirred at this temperature with 5% NaOH(aq) (prepared by dissolving 15 g NaOH in 300 mL water) for about 15 minutes. Agitation was stopped and the layers allowed to separate. The lower aqueous phase was cut away and the organic layer (containing the product) was washed with water (500 mL), brine (300 mL; from 100 g NaCl in water). The organic layer was then reduced in volume using a rotary evaporator to provide crude 52 as viscous, orange oil.

A glass column was charged with SiO$_2$ (2.00 kg) and the gel wetted with 10% EtOAc in hexanes. The crude tritosylate 52 was dissolved in approximately 200 mL of 2/1 hexanes/EtOAc and loaded onto the top of the column. The tritosylate was then eluted with the following mobile phase gradient, collecting 1 L fractions (1 CV=4 L): 10% EtOAc/hexanes: 16 fractions, 4 column volumes (CV); 15% EtOAc/hexanes: 21 fractions, 5 CV; 20% EtOAc/hexanes: 31 fractions, 7.5 CV.

The product containing fractions were pooled and the solvent removed using a rotary evaporator, followed by placing the oil under a high vacuum source for at least 4 hours to provide purified tritosylate 52 (101.3 g, 67.8% yield from Compound 49; 3 synthetic steps) with an HPLC purity of 98.6% (but there a shoulder is on the main peak).

Step 7: Preparation of tris-Dibenzylamine Derivative 53:

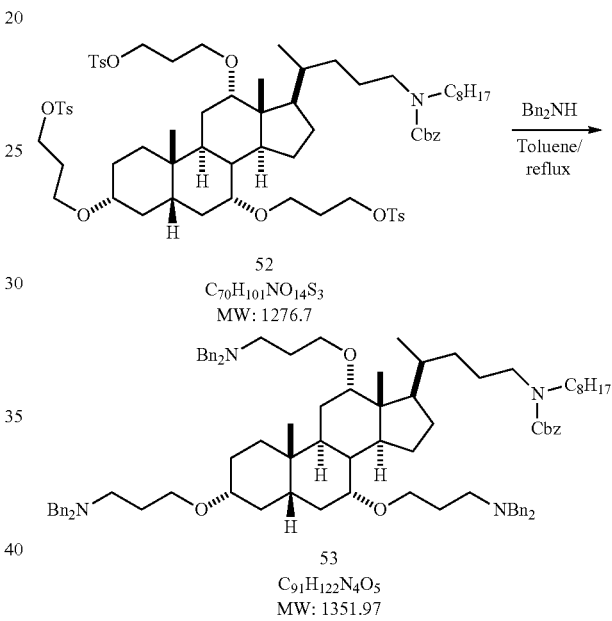

The tritosylate 52 oil (101 g, 79.1 mmole) was dissolved in toluene (450 mL) and transferred to a 2 L reaction flask. Dibenzylamine was added to the reaction flask and the contents of the flask heated to 110±2° C. under nitrogen overnight (18-24 hours). The next morning the batch was sampled and analyzed by LC/MS. Monotosylate was still observed so an additional 21.5 g (109 mmole) of Bn$_2$NH was added and the mixture heated at 110±2° C. for 4 hours followed by overnight at 85° C. (16-18 hours). The next morning the batch was analyzed, then reheated to 110±2° C. for 3 hour then cooled to ambient temperature. The batch was diluted with 2-MeTHF (800 mL), stirred for approximately 60 minutes then filtered to remove the solids. The solids were rinsed with 2-MeTHF (300 mL) and the product solution transferred to a 3 L reaction flask and diluted with 2-MeTHF (500 mL). The solution was cooled to 5-10° C. at which time HCl, 37% was added (60 mL, 720 mmole), until water-wet pH paper indicated that the pH was <3. The solids were filtered off and rinsed with 2-MeTHF (3×150 mL). The volume of the product solution was reduced by distillation (approx. 650 mL removed) and the solution transferred back to the reaction flask and cooled to 10-15° C. A solution of 1M NaOH(aq) (30 g NaOH in 750 mL water) was added over 30 minutes, keeping the temperature of the batch at 10-15° C. during the addition. After stirring for 45 minutes at 10-20° C. agitation was stopped and the layers allowed to separate. The organic, product layer was washed with water (350 mL), brine (250 mL) and the solvent removed under reduced pressure to provide an oil (Mass: 123 g). The oil was taken up in 6/1 hexane/EtOAc (250 mL) and filtered through silica gel (230-420 mesh, 75 g) eluting with 6/1 hexane/EtOAc, collecting 4×100 mL fractions then 4×200 mL fractions. The product containing fractions were pooled and the solvent removed under reduced pressure to provide tris-dibenzylamine derivative 53 as a colorless, viscous oil (102.4 g, Yield: 96%) with an HPLC purity of 85.4% (AUC).

Step 8: Preparation of CSA 54:

The CSA-54 solution was transferred to a flask containing Norit A decolorizing carbon (4.5 g) and stirred for approximately 30 minutes under $N_2$ at ambient temperature. The contents of the flask were filtered on a fritted funnel through a pad of filter agent and the flask/cake washed with 2-MeTHF (2×50 mL). The solvent was removed by distillation using a rotary evaporator and the residue diluted with EtOH (75 mL) and stripped again to provide CSA 54 as viscous, colorless oil. Yield (based on weight/weight analysis): 24.0 g (theory: 22.6 g). HPLC purity: 99.7% (AUC).

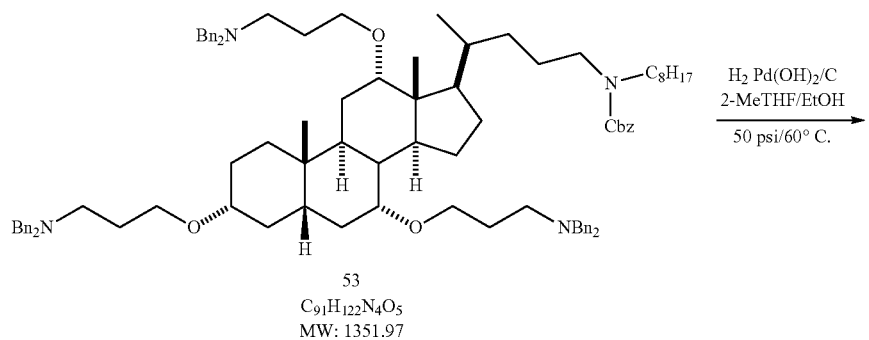

53
$C_{91}H_{122}N_4O_5$
MW: 1351.97

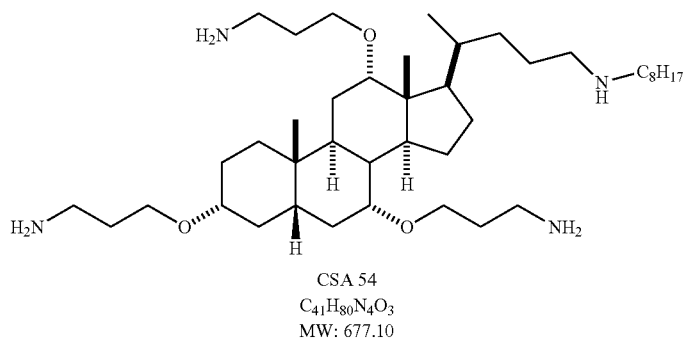

CSA 54
$C_{41}H_{80}N_4O_3$
MW: 677.10

A 2 L pressure flask was purged with $N_2$ and charged with Pd(OH)2/C (8.5 g). The crude tris-dibenzylamine derivative 53 (45.0 g, 0.0333 mole) was dissolved in 2-MeTHF (200 mL) and transferred to the pressure flask. The flask was diluted with EtOH (400 mL) and the contents of the flask stirred and heated to 60±2° C. while pressure purging with 4×50 psi N2, then 4×50 psi $H_2$. The reaction mixture was then hydrogenated at 50 psi $H_2$ and 60±2° C. for 3.5 hours at which time a sample analyzed by LC/MS indicated that the reaction was complete. The mixture was cooled to ambient temperature and filtered on a fritted funnel through a pad of filter agent. The flask and cake were rinsed with 2-MeTHF (2×50 mL) to provide a crude CSA-54 solution.

Example 2

Preparation of CSA-61

Step 1: Preparation of Compound 57 from Cholic acid

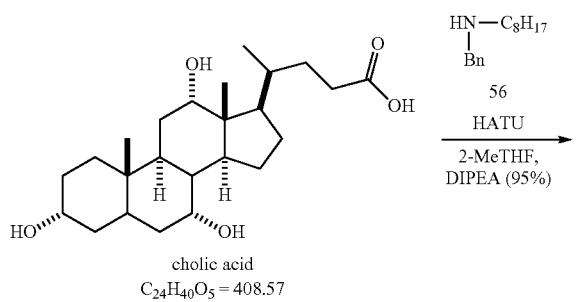

cholic acid
$C_{24}H_{40}O_5 = 408.57$

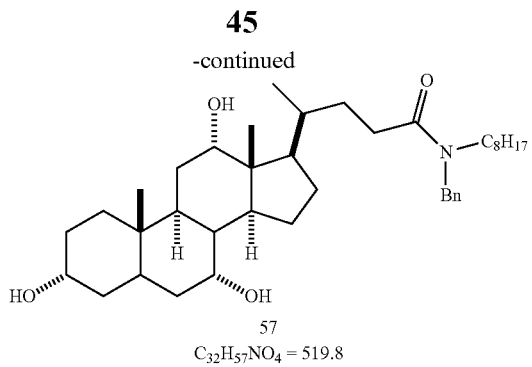

57
$C_{32}H_{57}NO_4 = 519.8$

To cholic acid (14.2 g) and 2-MeTHF (115 mL) was added octylbenzylamine 56 (7.63 g) and then DIPEA (7.1 mL). HATU (13.6 g) was then added and the slurry was aged at RT for an hour and then warmed to 50° C. overnight. Slowly added 3M HCl (50 mL) with ice bath cooling and cut the layers. The organic layer was washed sequentially with water (2×100 mL), sodium bicarbonate (8 wt %, 50 mL) and water (50 mL). The organic layer was concentrated to a foam, then azeotropically dried with toluene (150 mL) on the rotovap. A total of 25 g of octylbenzylamine 57 as a thick oil (21 g theoretical) was obtained upon evaporation. Due to the syrupy nature of the triol, it is more convenient to keep as a toluene solution and use directly in the next step.

Step 1a: Preparation of Octylbenzylamine 56

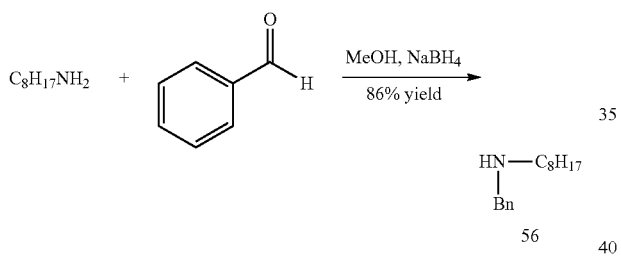

56

In a 2 L flask with an overhead stirrer, nitrogen line and thermocouple was added methanol (540 mL) and benzaldehyde (52 mL). With ice water cooling was added octylamine (84 mL) and then warmed to RT and aged overnight. The reaction solution was then cooled to 0-5° C. and sodium borohydride was added portionwise (very exothermic). The reaction was complete as assayed by GC-MS. Added water (50 mL) slowly followed by 2-MeTHF (500 mL). Very little bubbles or exotherm. Added 15 wt % NaCl (300 mL) and then cut the layers. The organic layer was then washed with water (2×200 mL) and concentrated to an oil that was distilled under vacuum (1-4 mm) in two major fractions. A total of 96 g of octylbenzylamine 56 was obtained (86% yield).

Step 1b: Preparation of Dibenzylacrylamide 58

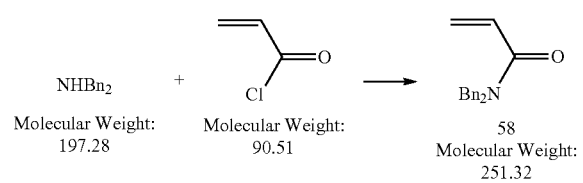

THF (1 L) was cooled to −60° C. and then acryloyl chloride (46.5 mL) was added followed by DIPEA (220 mL). Using a syringe pump, the dibenzylamine (105 mL) was slowly added to the mixture over 40 min. The mixture was allowed to warm to RT and then aged for 1 h. A heavy white precipitate formed during that time (DIPEA-HCl, presumably) which was filtered off and the filtrates concentrated to an oil containing some solids (15.5 g total weight, >100% yield). MTBE (600 mL) was then added to this mixture and some more solids came out of solution. They were again filtered off and the filtrates concentrated to provide dibenzylacrylamide 58 as a pale yellow oil (140 g, 100% isolated crude). Para-methoxyphenol (50 mg) added as a stabilizer and 58 was stored at 0-5° C.

Step 2: Michael Addition with Benzylacrylamide

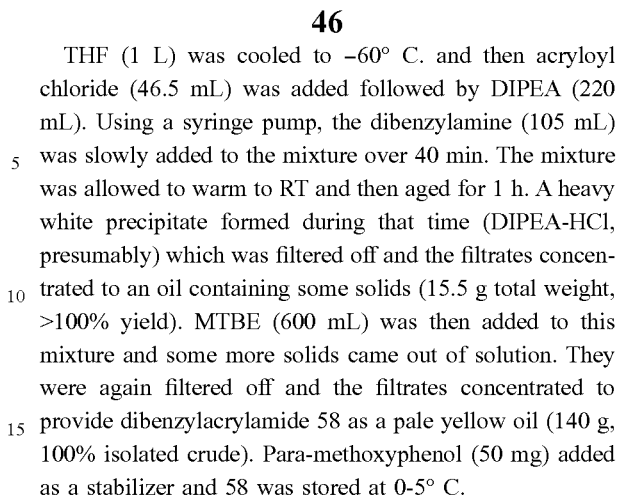

57
$C_{32}H_{57}NO_4 = 519.8$

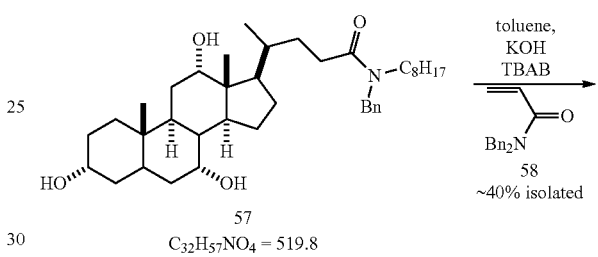

59
$C_{32}H_{57}NO_4 = 519.8$

To the triol 57 in toluene was added KOH (3.4 g), TBAB (0.7 g) and then a solution of the dibenzylacrylamide 58 in toluene (7.9 g in 3 mL) was added over 12 h using a syringe pump. After 20 h the amount of tris was 52%, bis, 31% and the mono Michael adduct 7% as assayed at 210 nm on a Betasil Phenyl-Hexyl column. Added water (50 mL) and then filtered through Solka-Flok. Washed the layers with water and then concentrated the organic layer. Chromatography on silica gel using 25% to 50% ethyl acetate: heptane gave 40% of the desired Michael addition product (59).

Step 3: Reduction of Compound 59

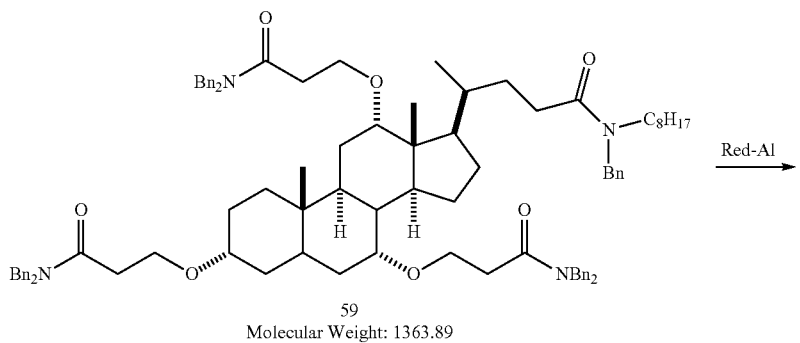

59
Molecular Weight: 1363.89

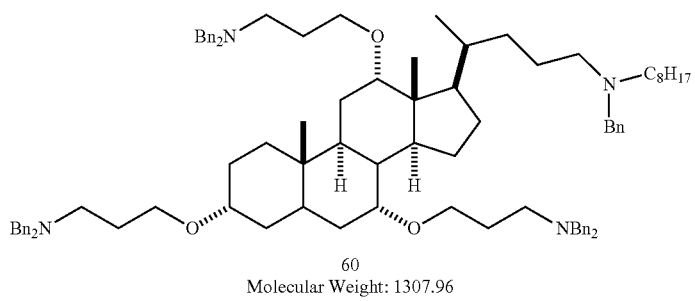

60
Molecular Weight: 1307.96

To Red-Al (6.1 mL) was added toluene (61 mL) and the solution cooled to 5-10° C. with an ice bath. The mixture of tris/bis compounds (59) dissolved in toluene (16 mL) were then added over 1 h to the Red-Al at RT. After assay confirmed the completion of the reaction, 1M Rochelle's salt (20 mL) was SLOWLY added due to the gas that came off. A rag layer was removed by filtration of the reaction mixture through Solka Flok. The layers were then cut and the organic layer washed with water (2×20 mL). The organic layer was concentrated to provide Compound 60 as a colorless oil (2.7 g) as the mixture of tris and bis addition products as assayed by HPLC-MS.

Step 4: Production of CSA 61

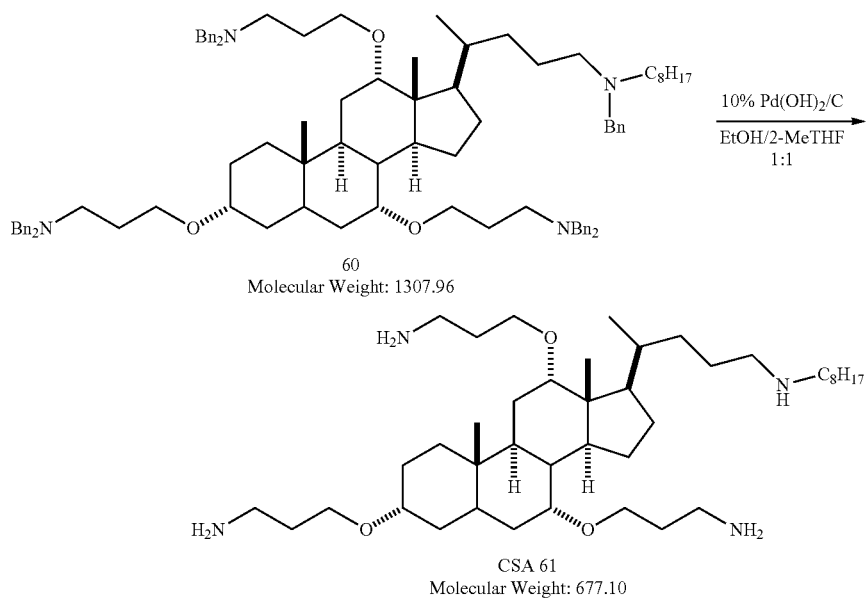

60
Molecular Weight: 1307.96

CSA 61
Molecular Weight: 677.10

The heptabenzyltetraamino steroid 60 (0.17 g) was dissolved in THF:ethanol (1:1, 20 mL/g) and then 10% Pd(OH)$_2$/C (34 mg, 20 wt %) was added. The reaction was placed under 60 psi H$_2$ at 60° C. for 30 h and then the catalyst was filtered off through Solka-Flok. The cake was washed with additional ethanol and the combined filtrates were concentrated to an oil to provide CSA 61 as a colorless oil (79 mg, ~90% pure by NMR, with a small amount of ethanol).

Example 3

Preparation of CSA-192

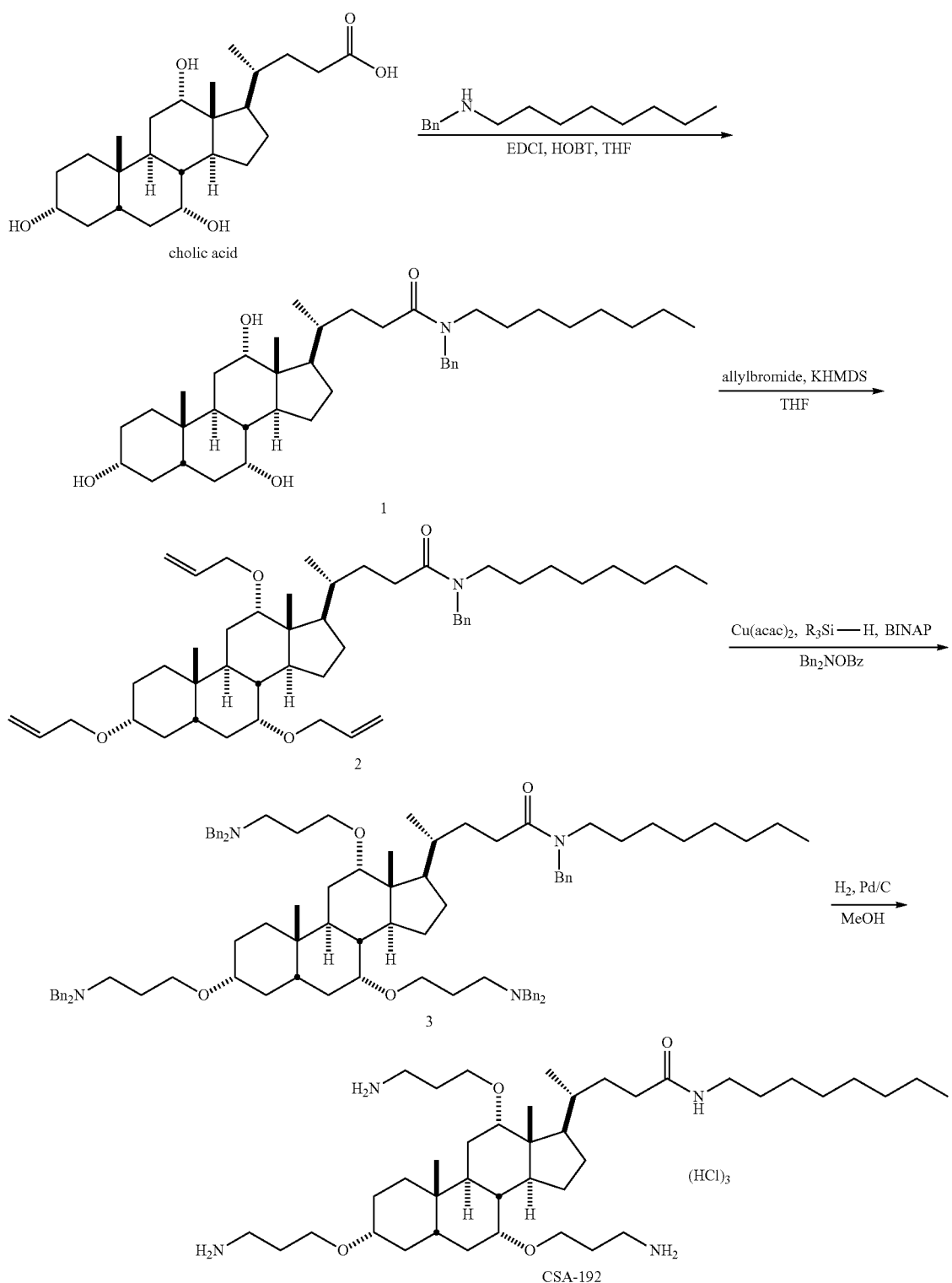

Compound 1

Cholic acid (2.0 g, 4.8 mmol), EDCI (920.2 mg, 4.8 mmol), HOBt (648.6 mg, 4.8 mmol) were combined, followed by addition of THF (40 mL). The mixture was stirred at room temperature for 30 min. Octyl amine (1.4 mL, 5.76 mmol) was added dropwise. The reaction maintained at room temperature for 10 h. A one to one mixture of hexanes and ethyl acetate (100 mL) and water (50 mL) were added. The organic layer was washed with 4 M aqueous HCl (3×50 mL), 20% aqueous NaOH (3×50 mL), and brine (50 mL), dried over anhydrous $Na_2SO_4$, and concentrated to give 2.6 g of a white solid (86% yield).

Compound 2

N-octylcholamide (1) (1.7 g, 2.8 mmol) and KHMDS (2.8 g, 14 mmol) were combined, followed by addition of TFH (20 mL). The mixture was stirred at room temperature for 30 min and then cooled to 3° C. Allyl bromide (1.21 mL, 14 mmol) was added dropwise, and the mixture was allowed to warm to room temperature. After 30 min, hexane (20 mL) was added, and the resulting mixture was washed with aqueous citric acid (40%, 20 mL) and water (2×20 mL). The resulting organic material was concentrated, and the product was isolated after silica gel chromatography (eluent: 2% ethyl acetate in hexanes) as 1.5 g of a clear glass (71% yield).

Compound 3

In a nitrogen-filled glovebox, a 5 mL screw-cap vial was charged with $Cu(OAc)_2$ (10.8 mg, 0.06 mmol, 6.0 mol %) and (R)-DTBM-SEGPHOS (77.7 mg, 0.066 mmol, 6.6 mol %). THF (6.0 mL) was added and the mixture was stirred for 5 min before the dropwise addition of diethoxymethylsilane (DEMS) (810 mg, 6 mmol, 6.0 equiv). Stirring was continued for an additional 10 min before the mixture was added via syringe to a second screw-cap vial, equipped with a magnetic stir bar and charged with 2 (756 mg 1.0 mmol, 1.0 equiv) and dibenzylhydroxylamine benzoyl ester (1.14 g 3.6 mmol, 3.6 equiv). The vial was sealed and removed from the glove box and stirred in an oil bath at 40° C. for 48 h. The reaction mixture was allowed to cool to rt, diluted with a saturated aqueous $Na_2CO_3$ solution (10 mL) and the aqueous phase was extracted with EtOAc (2×20 ml). The combined organic phases were concentrated, and 3 was obtained as white solid (808 mg, 60%) after silica gel chromatography (eluent: 10% EtOAc/hexanes).

Compound 3 (500 mg, 0.38 mmol) was dissolved in a mixture of THF and methanol (10:1). Pd/C (10% Pd, 20 mg) was added, and the mixture was stirred under an atmosphere of $H_2$ for 24 h. Solids were removed via filtration, and filtrate was treated with hydrochloric acid (1 mL). After concentration, CSA-192 HCl salt was isolated as 0.30 g of a white solid (99% yield).

Example 4

Preparation of CSA-65

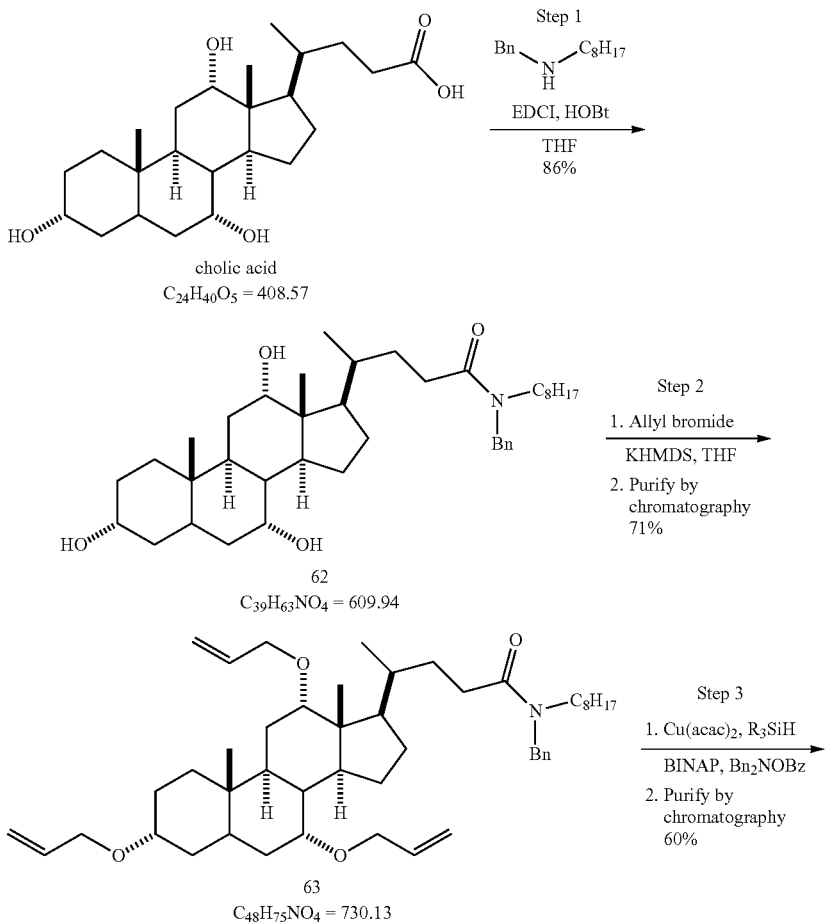

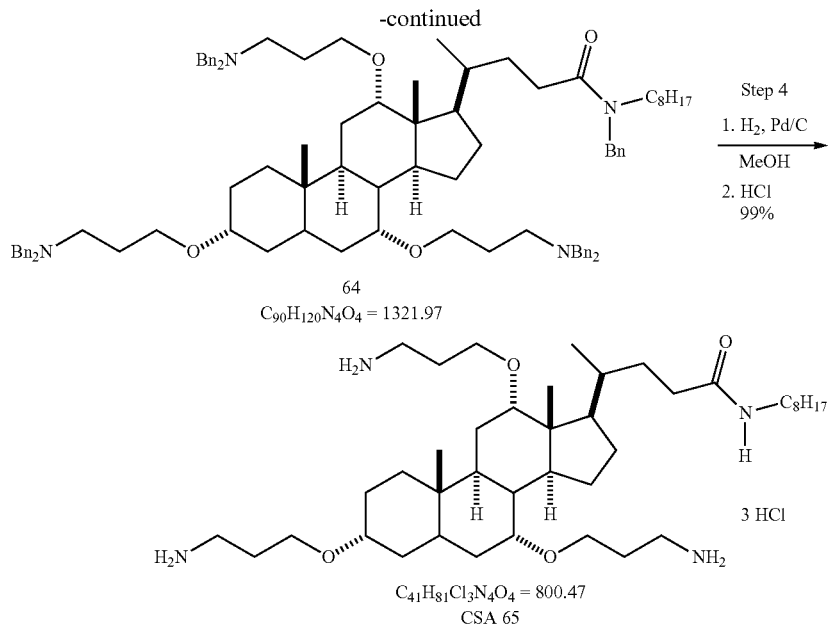

64
$C_{90}H_{120}N_4O_4 = 1321.97$ $C_{41}H_{81}Cl_3N_4O_4 = 800.47$
CSA 65

Compound 62

Cholic acid (2.0 g, 4.8 mmol), EDCI (920.2 mg, 4.8 mmol), HOBt (648.6 mg, 4.8 mmol) were combined, followed by addition of THF (40 mL). The mixture was stirred at g room temperature for 30 min. Octyl amine (1.4 mL, 5.76 mmol) was added dropwise. The reaction maintained at room temperature for 10 h. A one to one mixture of hexanes and ethyl acetate (100 mL) and water (50 mL) were added. The organic layer was washed with 4 M aqueous HCl (3×50 mL), 20% aqueous NaOH (3×50 mL), and brine (50 mL), dried over anhydrous $Na_2SO_4$, and concentrated to give 2.6 g of Compound 62 as aa white solid (86% yield).

Compound 63

N-octylcholamide (62) (1.7 g, 2.8 mmol) and KHMDS (2.8 g, 14 mmol) were combined, followed by addition of TFH (20 mL). The mixture was stirred at room temperature for 30 min and then cooled to 3° C. Allyl bromide (1.21 mL, 14 mmol) was added dropwise, and the mixture was allowed to warm to room temperature. After 30 min, hexane (20 mL) was added, and the resulting mixture was washed with aqueous citric acid (40%, 20 mL) and water (2×20 mL). The resulting organic material was concentrated, and the product was isolated after silica gel chromatography (eluent: 2% ethyl acetate in hexanes) as 1.5 g of Compound 63 as a clear glass (71% yield).

Compound 64

In a nitrogen-filled glovebox, a 5 mL screw-cap vial was charged with $Cu(OAc)_2$ (10.8 mg, 0.06 mmol, 6.0 mol %) and (R)-DTBM-SEGPHOS (77.7 mg, 0.066 mmol, 6.6 mol %). THF (6.0 mL) was added and the mixture was stirred for 5 min before the dropwise addition of diethoxymethylsilane (DEMS) (810 mg, 6 mmol, 6.0 equiv). Stirring was continued for an additional 10 min before the mixture was added via syringe to a second screw-cap vial, equipped with a magnetic stir bar and charged with 63 (756 mg 1.0 mmol, 1.0 equiv) and dibenzylhydroxylamine benzoyl ester (1.14 g 3.6 mmol, 3.6 equiv). The vial was sealed and removed from the glove box and stirred in an oil bath at 40° C. for 48 h. The reaction mixture was allowed to cool to rt, diluted with a saturated aqueous $Na_2CO_3$ solution (10 mL) and the aqueous phase was extracted with EtOAc (2×20 ml). The combined organic phases were concentrated, and Compound 64 was obtained as white solid (808 mg, 60%) after silica gel chromatography (eluent: 10% EtOAc/hexanes).

CSA-65

Compound 64 (500 mg, 0.38 mmol) was dissolved in a mixture of THF and methanol (10:1). Pd/C (10% Pd, 20 mg) was added, and the mixture was stirred under an atmosphere of $H_2$ for 24 h. Solids were removed via filtration, and filtrate was treated with hydrochloric acid (1 mL). After concentration, CSA-65 HCl salt was isolated as 0.30 g of a white solid (99% yield).

Example 5

Preparation of CSA-70

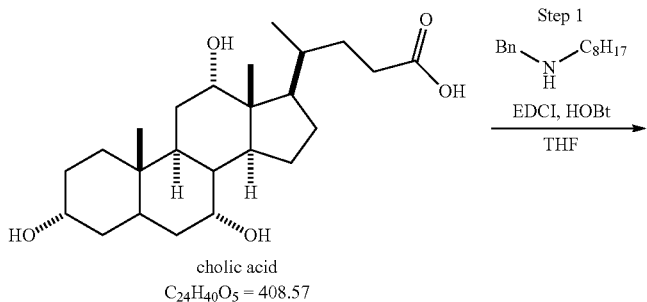

cholic acid
$C_{24}H_{40}O_5 = 408.57$

-continued
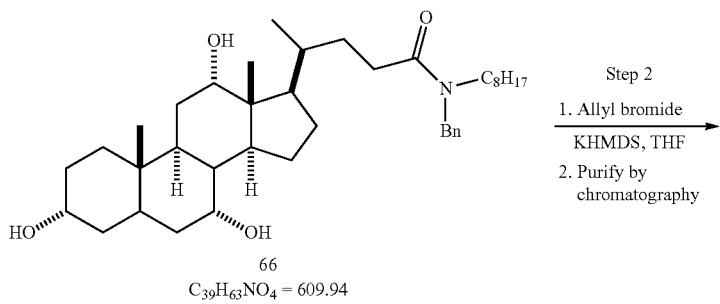
66
C₃₉H₆₃NO₄ = 609.94
Step 2
1. Allyl bromide, KHMDS, THF
2. Purify by chromatography
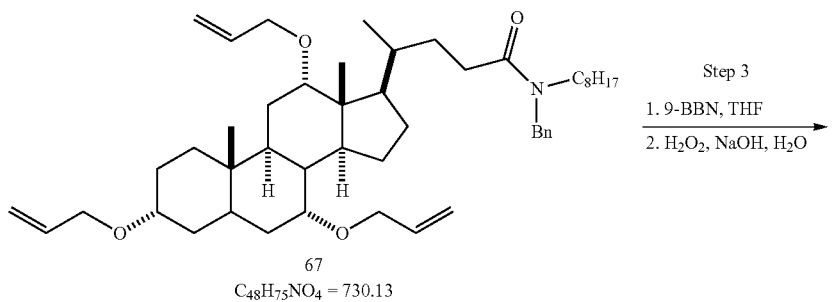
67
C₄₈H₇₅NO₄ = 730.13
Step 3
1. 9-BBN, THF
2. H₂O₂, NaOH, H₂O
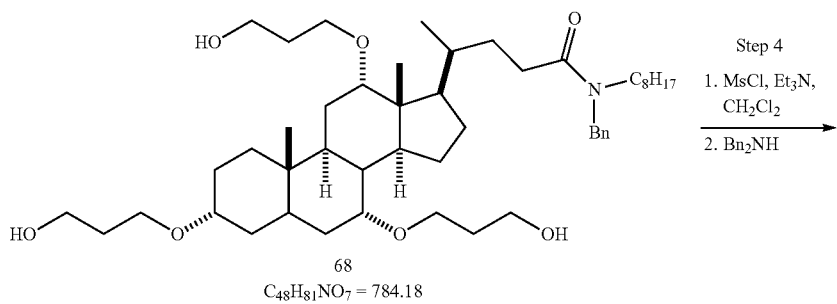
68
C₄₈H₈₁NO₇ = 784.18
Step 4
1. MsCl, Et₃N, CH₂Cl₂
2. Bn₂NH
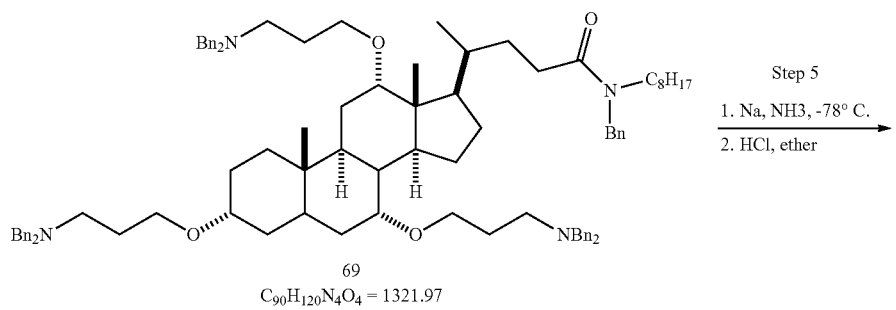
69
C₉₀H₁₂₀N₄O₄ = 1321.97
Step 5
1. Na, NH3, -78° C.
2. HCl, ether
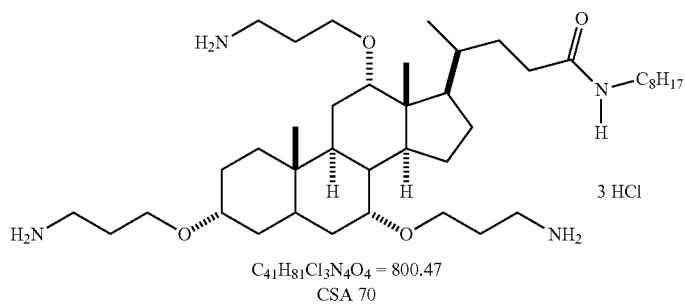
3 HCl
C₄₁H₈₁Cl₃N₄O₄ = 800.47
CSA 70

N-benzyl-N-octylcholamide (66)

EDCI (920.2 mg, 4.8 mmol), and HOBt (648.6 mg, 4.8 mmol) were added to a solution of Cholic acid (2.0 g, 4.8 mmol) in THF (40 mL). The mixture was stirred at room temperature for 30 min. Benzyloctylamine (1.26 g, 5.76 mmol) was added dropwise. The mixture was maintained at room temperature for 10 h. A one to one mixture of hexanes and ethyl acetate (100 mL) and water (50 mL) were added. The organic layer was washed with 4 M aqueous HCl (3×50 mL), 20% aqueous NaOH (3×50 mL), and brine (50 mL), dried over anhydrous $Na_2SO_4$, and concentrated to give Compound 66 as a white solid (2.60 g, 86% yield).

Compound 67

KHMDS (2.8 g, 14 mmol) was added to a solution of Cholamide 66 (1.7 g, 2.8 mmol) in THF (20 mL). The mixture was stirred at room temperature for 30 min and then cooled to 0° C. Allyl bromide (1.21 mL, 14 mmol) was added dropwise, and the mixture was allowed to warm to room temperature. After 30 min, hexane (20 mL) was added, and the resulting mixture was washed with aqueous citric acid (40%, 20 mL) and water (2×20 mL). The resulting organic material was concentrated, and the product was isolated after silica gel chromatography (eluent: 2% ethyl acetate in hexanes) to provide Compound 67 as a clear glass (1.50 g, 71% yield).

Compound 68

Tris-allylether 67 (1.5 g, 2.0 mmol) was dissolved in THF (10 mL) and 9-BBN (14 mL of a 0.5 M solution in THF, 7.0 mmol) was added dropwise. The solution was allowed to stir at room temperature for 4 h. Water (5 mL) was slowly added, followed by an aqueous solution of NaOH (4 M, 5 mL) and and $H_2O_2$ (5 mL, 30% solution in water). The mixture was stirred at room temperature for 1 h. Ether (30 mL) was added, and the aqueous material was discarded. The ether solution was washed with brine (2×20 mL), dried over sodium sulfate, and concentrated. The tri-alcohol (68) was isolated as a clear oil (1.49 g, 95% yield).

Compound 69

Tri-alcohol 68 (1.49 g, 1.9 mmol) was dissolved in dichloromethane (10 mL), and the solution was cooled to 0° C. Triethylamine (1 mL) was added, followed by dropwise addition of mesylchloride (0.53 mL, 6.8 mmol). The resulting mixture was stirred for 1 h, then water (10 mL was added. The organic layer was washed with aqueous HCl (0.1 M, 10 mL) and brine (10 mL), dried over anhydrous $Na_2SO_4$, and concentrated to a clear oil. This oil was immediately dissolved in acetonitrile (10 mL), and dibenzyl amine (1.3 mL, 6.7 mmol) was added. The mixture was stirred at room temperature for 12 h. The dichloromethane was removed under vacuum to give a yellow oil. After silica gel chromatography (dichloromethane:methanol:ammonium hydroxide (9:1:0.1)) gave Compound 69 as a clear oil (2.31 g, 92% yield).

CSA 70

A solution of sodium metal (100 mg) in $NH_3$ (15 mL) at −78° C. was prepared, and to this solution compound 69 (1.32 g, 1.1 mmol) in THF (5 mL) was added dropwise. After 40 min, methanol (10 mL) was slowly added. The mixture was allowed to warm to room temperature and then concentrated to give a clear oil. KIN-219 was obtained as a white solid (0.65 g, 86% yield) after silica gel chromatography (dichloromethane:methanol:ammonium hydroxide (7:3:1)). The trihydrochloride salt was formed by dissolving the freebase in ether (5 mL) and adding hydrogen chloride (2 mL of a 2 M solution in ether). The ether and excess hydrogen chloride were removed under vacuum to give the tri-HCl salt of CSA 70 as a white solid (0.76 g).

Example 6

Preparation of CSA-78

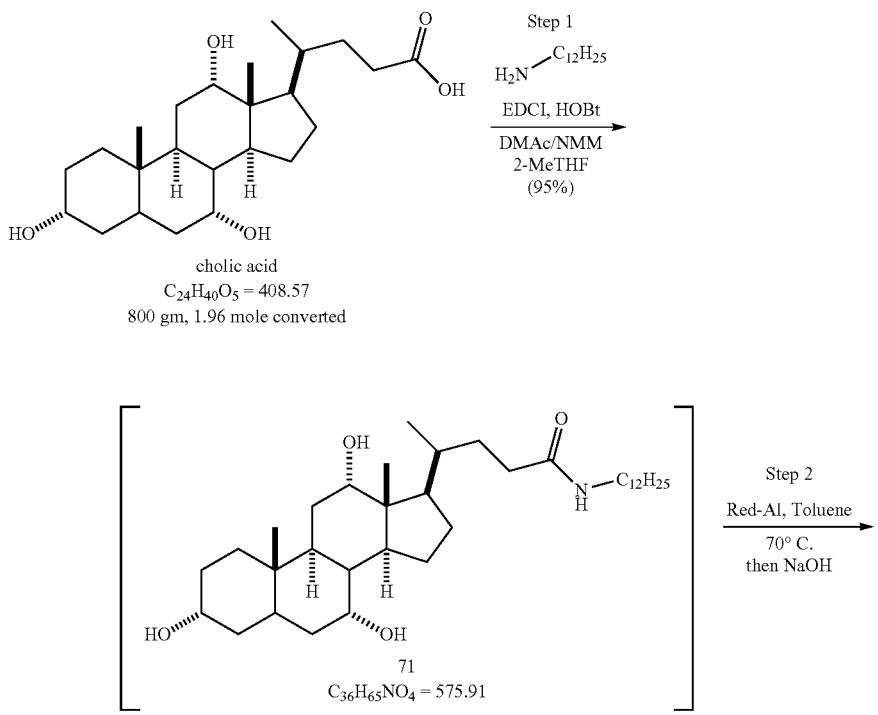

-continued
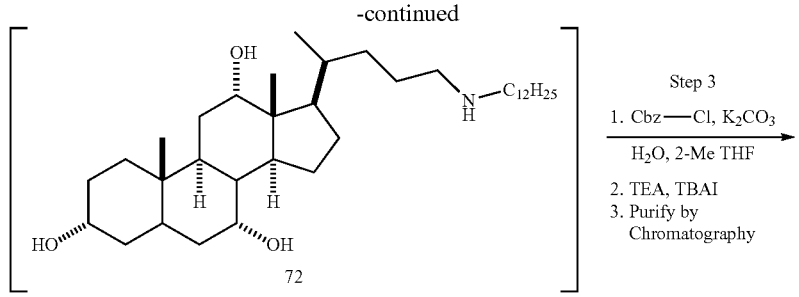
72
$C_{36}H_{67}NO_3 = 561.92$
Step 3
1. Cbz—Cl, $K_2CO_3$
   $H_2O$, 2-Me THF
2. TEA, TBAI
3. Purify by Chromatography
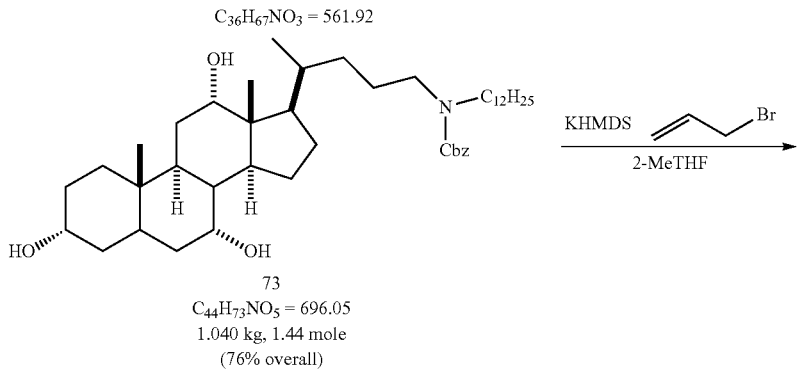
73
$C_{44}H_{73}NO_5 = 696.05$
1.040 kg, 1.44 mole
(76% overall)
KHMDS, allyl bromide
2-MeTHF
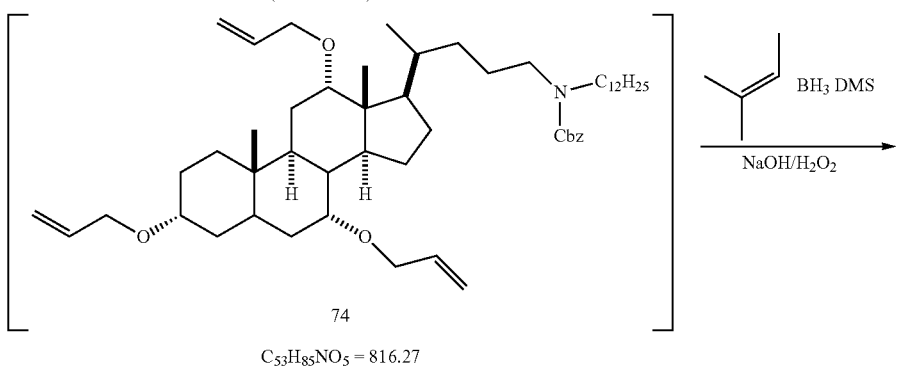
74
$C_{53}H_{85}NO_5 = 816.27$
$BH_3$ DMS
NaOH/$H_2O_2$
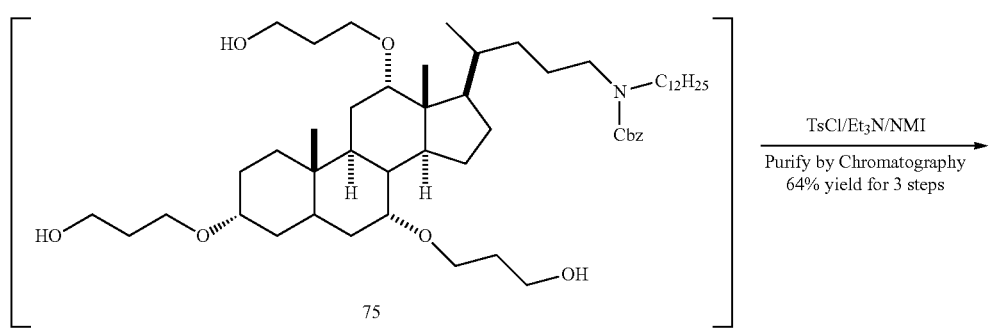
75
$C_{53}H_{91}NO_8 = 870.31$
$TsCl/Et_3N/NMI$
Purify by Chromatography
64% yield for 3 steps
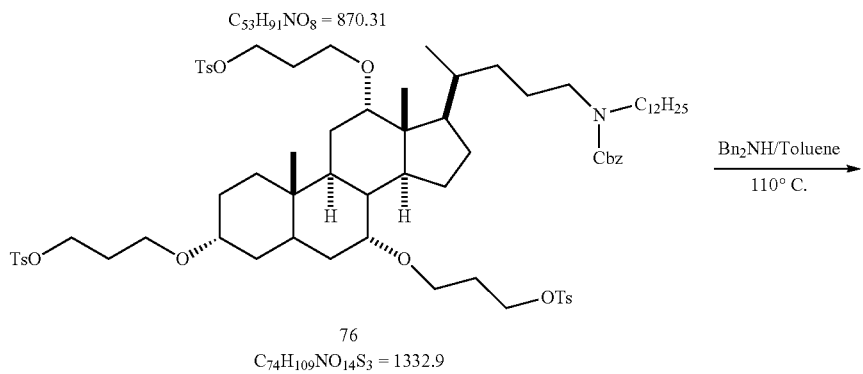
76
$C_{74}H_{109}NO_{14}S_3 = 1332.9$
$Bn_2NH$/Toluene
110° C.

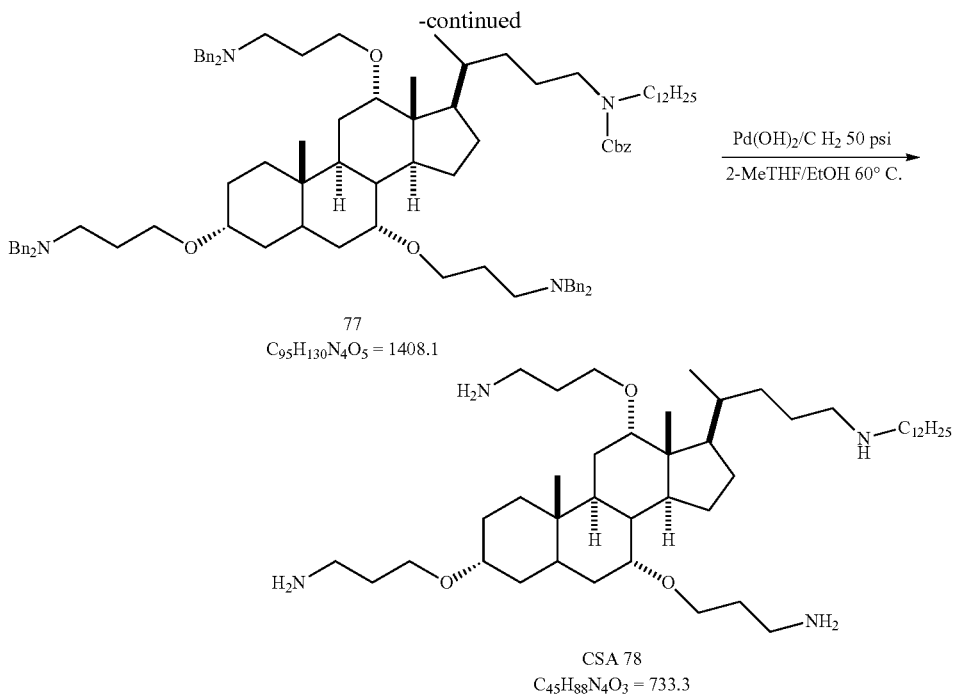

77
$C_{95}H_{130}N_4O_5 = 1408.1$

CSA 78
$C_{45}H_{88}N_4O_3 = 733.3$

Compound 71

To a 20.0 L glass reactor equipped with a mechanical stirrer, thermocouple and inert gas inlet was charged DMAc (1750 mL), cholic acid (700.0 g, 1.713 mole, 1.0 eq), HOBt hydrate (11.6 g, 0.0856 mole, 0.05 eq.), and EDCI (361.3 g, 1.884 mole, 1.1 eq). Agitation was begun and N-methylmorpholine (433.4 g, 4.28 mole, 2.5 eq.) was added, followed by Dodecylamine (381 g, 2.056 mole, 1.2 eq.), added as a solid in portions over about 30 minutes, keeping the temperature of the reaction mixture between 15-25° C. during the addition. The reaction mixture was then stirred under nitrogen warming first from 18° C. to 25° C., then holding overnight at 30° C.

Upon confirmation of product by LC/MS, the mixture was diluted with 2-MeTHF (6125 mL) and cooled to 10° C. The reaction was carefully quenched by slow addition of 3M HCl (2625 mL) over approximately 30-45 minutes, keeping the temperature of the mixture below 30° C. during the addition using external cooling and addition control. The mixture was stirred for an additional 15 minutes then the contents were allowed to separate. The lower aqueous phase was removed and the upper, organic product layer washed with water (3080 mL), ~8% NaHCO$_3$ (aq) (2450 mL), and 5% brine (2450 mL). The crude dodecylamide 71 was confirmed by LC/MS. A theoretical total of 986.6 g of dodecylamide 71 was retained in the 2-methyl THF solution (4699.8 grams total) in order to facilitate handling in the next step. One half of this solution [dodecylamide 71 (493.3 g, 0.857 mole) theoretical dissolved in 2-Methyl THF (2350 mL)] was carried on to the next step.

Compound 72

To a 30 L glass jacketed reactor equipped with an overhead mechanical stirrer, 2 L addition funnel, thermocouple and inert gas inlet, controlled by a chiller, was charged dodecylamide 71 [(493.3 g, 0.857 mole theoretical) dissolved in 2-Methyl THF (2350 mL) from the previous step]. Toluene was added (~19 L) followed by vacuum distillation (200-250 mm Hg) at 70-75° C. to solvent swap toluene for 2-Methyl THF (2.83 kg, 2-MeTHF/water/toluene collected). Additional toluene was added bringing the total to ~19.3 L in the reactor. A dean stark trap was placed on the 30 L reactor and the mixture was heated to 75-80° C. under vacuum (200-250 mm Hg) for ~30 minutes to azeotropically remove the remaining water from the reaction mixture. A total of ~1 L of toluene was removed from the dean stark trap. The contents were then adjusted to 65-75° C. Red-Al, as a 60-65 wt % solution in toluene (1558.3 g/~1505 mL, 4.625 moles, 5.4 eq) was diluted with toluene (1491.4 mL) and added over 90 minutes to the amide at 75° C. with vigorous agitation. Once all Red-Al was added, the batch was stirred at 80-85° C. until LC/MS indicated that all dodecylamide 71 had been consumed (1-2 hours). The reaction mixture was then stirred under N$_2$ at 55° C. overnight. The reaction mixture was cooled to +10° C. and quenched by slow addition of 5% NaOH solution (89.6 g NaOH, in 1792.5 mL water), since an exotherm with significant off-gassing occurs. The reaction mixture was then warmed to ambient temperature and stirred for an additional 3 hours. Agitation was stopped and the layers allowed to separate. The lower aqueous layer was separated and the upper organic product layer washed with 5% NaOH (aq) (89.6 g NaOH in 1792.5 mL water). The layers were separated and the organic product layer stirred at ambient temperature with water (3722 mL) for 10 minutes then the agitation was stopped and the layers separated. The organic product layer was reduced in volume to ~10.5 L by vacuum distillation and the solution of dodecylamine 72 (481.3 g theoretical) was carried on directly to the next step in the synthetic sequence.

Compound 73

To a 30 L, ChemGlass jacketed reactor equipped with an overhead mechanical stirrer, 250 mL addition funnel, thermocouple and inert gas inlet controlled by a chiller was charged the toluene solution (~10.5 L) containing the dodecylamine 72 (481.3 g theoretical) from the previous step, 2-MeTHF (3.01 L) was added and cooled to 5-10° C.

Aqueous potassium carbonate (592 g, 4.28 mole, 5.0 eq in 3.5 L water) was added followed by slow addition of Cbz-Cl (169.5 g, 0.994 mole, 1.16 eq.) over 20 minutes at 5-10° C. The reaction was stirred at 10° C. until no dodecylamine 2 was detected by LC/MS and product formation was confirmed (typically overnight). The reaction mixture was then quenched with aqueous ammonium chloride, (686 g in 2.24 L water), at 10° C. and stirred while warming to 18-25° C. The layers were separated and the organic product layer was stripped of solvent to produce crude Cbz protected dodecylamine 73 675 g (596.2 g theoretical) of a crude yellow/orange syrup.

To a portion of the crude Cbz protected dodecylamine 73 syrup (520.3 g) was charged $SiO_2$ (800 g Silicycle brand Siliflash 60, 230-400 mesh) and $CH_2Cl_2$ (as needed) to wet the silica gel and adsorb the crude material onto the gel. The mixture was then stripped to dryness and added to the top of a flash column that had been packed with silica gel (2.0 Kg) and wetted with hexanes. The column was eluted with the following solvent gradients, collecting 1.0 L fractions as follows:

100% Hexanes: Fractions#: 1-7 (7 L total)
25%, Ethyl acetate/Hexanes: Fractions#: 8-14 (8.0 L total charged to column)
50%, Ethyl acetate/Hexanes: Fractions#: 15-22 (8.0 L total charged to column)
100% Ethyl acetate, Fractions#: 23-45 (25.0 L total charged to column)

A total of 45×1.0 L fractions were collected resulting in a total of ~45 L of solvent used for each of three columns run. Fractions containing product were pooled and stripped of solvent (Rf of product: 0.45, developed with EtOAc, PMA visualization) to provide purified Cbz protected dodecylamine 73 as a white foam. Mixed fractions containing product (Rf=0.45) plus faster moving impurities (Rf=0.76 and 0.88) were also collected for additional purification by chromatography.

Compound 74

Compound 73 (216 g, 310.5 mmole) was azetropically dried using THF to <250 ppm water, then dissolved in 2-MeTHF (2.3 L) and transferred to a 10 L jacketed reactor. This solution was diluted with 2-MeTHF (1.5 L) and cooled to −15±3° C. KHMDS (372 g, 1.86 moles, 6.0 eq.) was then added in 7 portions over about 40 minutes, keeping the temperature in the desired range (no exotherm observed). After an additional stir time of 15 minutes, allyl bromide (225 g, 1.86 mole, 6.0 eq.) in 2-MeTHF (650 mL) was added over 35 minutes at −15±5° C. (slight exotherm during this addition). The reaction was stirred at temperature for 4 hours, then gradually warmed to 10° C., at which time TLC/LC/MS indicated that the reaction was complete (no further change). The reaction mixture was cooled and quenched by addition of 1M HCl(aq) (2.25 L, 2.25 mole). The layers were separated and the aqueous layer back-extracted with 2-MeTHF (550 mL). The combined organic layers were washed with aqueous 1M HCl (375 mL), 8% aqueous $NaHCO_3$ (550 mL), and brine (2×275 mL). The organic phase was then stripped of solvent to provide 250.8 g of triallyl 74 (98.9% yield) as an orange syrup. This material was confirmed by LC/MS and and deemed suitable to carry on to the next step.

Compound 75

To a 20 L jacketed, cylindrical reactor was charged 2-MeTHF (3.00 L) and cooled to 5-10° C. 2-Methyl-2-butene was charged (839 g, 11.97 moles, 30 eq.), followed by $BH_3$ DMS complex (455 g, 5.99 moles, 15 eq.) added over 2 hours (exothermic). After stirring at 5-15° C. for 2.5 hours a solution of triallyl-74 (326 g, 399 mmoles) in 2-MeTHF (1.2 L) was added over 40 minutes at 5-10° C. The reaction was then stirred overnight at 10±2° C. The next morning the oxidative workup began by slowly charging aqueous NaOH (1916 g of 50%, 23.95 moles, 60 eq. diluted to a total volume of 2.3 L) over 35 minutes followed by 30% $H_2O_2$ (2.71 kg, 23.95 moles, 60 eq.) over 4.5 hours (very exothermic reaction). The mixture was stirred for 60 minutes then 8% $Na_2SO_3$ (605 g, 4.8 moles, 12 eq. in water 5.0 L) was slowly added. After stirring for 3 hours at 18° C. the stirring was halted and the layers were allowed to separate overnight. The next morning the phases were separated and the organic product layer washed with water (2×2.5 L) and brine (2×0.75 L). The organic portion was distilled to remove most of the 2-MeTHF solvent. Toluene (1.0 L) was added and the solution distilled again. Methanol was added (1.0 L) and the solution heated to reflux for about 1 hour at which time the solution was cooled and distilled to remove the MeOH. At this point a series of toluene additions/distillations was performed (8×250 mL) to remove the 3-methyl-2-butanol, the by-product from the hydroboration with diisoamylborane. The distillation was monitored by 1H NMR to insure complete removal of the butanol prior to the next step in the synthetic sequence. On the final distillation, the distillate contained only a trace of the 3-methyl-2-butanol and the product oil had no detectable amounts of this by-product by 1H NMR. A solvent exchange with 2-MeTHF (2×250 mL) was performed (to remove toluene and prepare for the next step); a total of 361.2 g of crude triol-75 (>100% yield) was obtained.

Compound 76

To a 10 L jacketed, cylindrical reactor was charged triol 75 (345.5 g crude, 397 mole theory) in 2-MeTHF (2.25 L) and cooled to 5-15° C. 1-Methylimidazole (163 g, 1.985 moles, 5.0 eq.) was charged followed by triethylamine (241 g, 2.382 moles, 6.5 eq.) added using an addition funnel. Meanwhile, a solution of p-toluenenesulfonyl chloride (605 g, 3.176 moles, 8.0 eq.) in 2-MeTHF (1.5 L) was prepared and then added to the 10 L reactor over 45 minutes at 10-15° C. The reaction was then slowly warmed to 25±2° C. for an overnight stir period. The next morning analysis by TLC (Tritosylate: Rf: 0.20; Ditosylate: Rf: 0.08 in 2.5/1 hexane/EtOAc with PMA visualization) and LC/MS indicated that ditosylate was still present. The mixture was stirred for an additional 12 hours at 25±2° C. for 6 hours and analyzed again by TLC and LC/MS. Although the level of ditosylate was dropping it was still present. Thus, an additional 7.5% of reagents (NMI. $Et_3N$ and Ts-Cl; 12 g, 18.2 g, 45.0 g resp.) were added and the reaction mixture stirred overnight at 25±2° C. The next morning, an additional charge of Ts-Cl was made (45 g, 236 mmole) (LC/MS indicated a small amount ditosylate remained). The reaction mixture was stirred for an additional 75 minutes at 25° C., then cooled to 0-10° C. for quench and work up. A solution of 2M HCl (2.5 L) was slowly added over 30 minutes, keeping the temperature below 20° C. The mixture was stirred for an additional 15 minutes then agitation stopped and the phases allowed to separate. The lower, aqueous phase was then back extracted with 2-MeTHF (1.0 L) and then the combined organic phases were cooled to 0-5° C. at which time 5% NaOH (aq)

(1.2 L) was slowly added. The mixture was stirred for 10 minutes then agitation stopped and the phases allowed to separate. The organic phase was washed with water (1.3 L), then brine (2×0.75 L). The basic aqueous, water and brine washes were combined and back extracted with 2-MeTHF (1 L). The organic portion was washed with brine (2×150 mL) and then combined with the main organic portion. The crude tritsoylate 76 solution was distilled under vacuum reducing the volume to about 1.75-2.0 L in preparation for the purification step.

Purification:

A silica gel column was prepared (2.45 kg; 230-400 mesh) and wetted with 10% EtOAc in hexanes. The crude tritosylate 76 was sorbed onto silica gel (1250 g) by adding the tritosylate solution to the gel and distilling under vacuum to get a free-flowing powder. The tritosylate/silica gel was added to the top of the column and then eluted using a 10% EtOAc in hexanes to 25% EtOAc in hexanes gradient. 1 L fractions were collected and the pure (by TLC) fractions were pooled and the solvent removed in vacuo to provide 322.4 g of tritosylate 76 (60.9% yield from Cbz-3) as a colorless oil.

Compound 77

Purified tritosylate-76 (300.0 g, 225 mmoles) was dissolved in toluene (1.35 L) and dibenzylamine (577 g, 2.93 moles, 13 eq.) added. The reaction mixture was heated to 115±2° C. for 40 hours at which time the reaction was considered to be complete. The mixture was cooled to ≤15° C. and the salts filtered off, rinsing the salts with toluene (6×50 mL). The product solution was transferred to a 12 L flask, diluted with 2-MeTHF (4.1 L) and cooled to ≤15° C. The mixture was acidified by slow addition of HCl, 37% (240 mL, 2.88 moles) over 60 minutes, keeping the temperature in the 12-17° C. range. The resulting salts were filtered, and the salt cake washed with 2-MeTHF (8×150 mL). The combined organic product layers were transferred back to the 12 L flask. Dilute NaOH(aq) was prepared (50% NaOH, 185 g, 2.31 moles, in 2.0 L water) and slowly added to the product solution in the 12 L flask over about 45 minutes. The batch was stirred for an additional 15 minutes at 10-15° C., then agitation was stopped and the layers allowed to separate. The lower phase was cut away and the upper, product layer washed with water (2×500 mL), brine (2×250 mL) and the solvent reduced to a mass of 1540 g. Exactly 25% of the batch was removed and stripped to an orange oil (82 g). This oil was diluted with 6/1 hexane/EtOAc (about 80 mL) and filtered through a plug of silica gel (100 g), eluting with 6/1 hexane/EtOAc until elution was complete. The solution was stripped to yield 73.0 g of Compound 77 as a yellow oil (92.6% yield) with 92-94% HPLC purity.

CSA 78

Compound 77 (7.3 g, 5.2 mmole) was dissolved in EtOH/2-MeTHF (75 mL/35 mL) and hydrogenated with Pd(OH)$_2$/C catalyst (1.77 g) at 60° C. under H$_2$ pressure of 50 PSI for 5.5 hours at which time HPLC analysis indicated the reaction was complete. The mixture was cooled and the catalyst filtered off, rinsing the catalyst cake with EtOH (3×10 mL). The colorless solution was stripped to an oil to provide 3.41 g of CSA 78 free base (90% yield) that was 85.6% pure by HPLC.

What is claimed is:

1. A method of making a compound of Formula (I) or (III), comprising the steps of:

(a) reacting a compound of Formula (1) and R$_1$R$_2$—NH

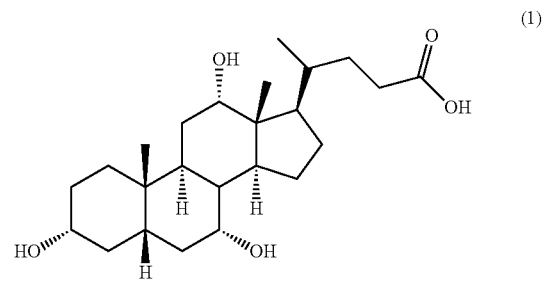

to form a compound of Formula (2):

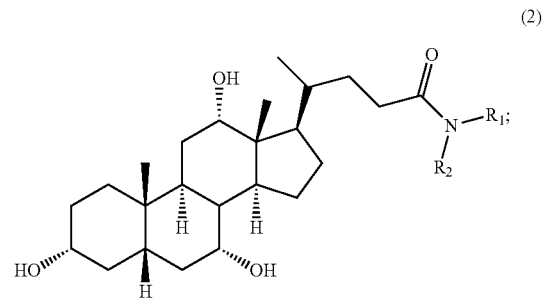

(b) optionally reducing a compound of Formula (2) to form a compound of Formula (3):

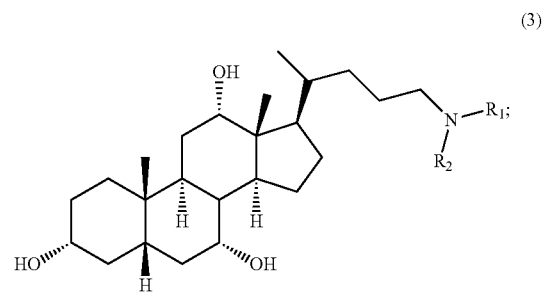

(c1) optionally protecting a compound of Formula (3) with an amine protecting group (PG) to form a compound of Formula (4):

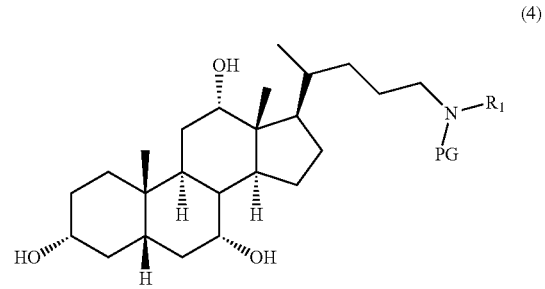

where $R_2$ is a hydrogen and is replaced with the amine protecting group, or (c2) optionally protecting a compound of Formula (2) with an amine protecting group (PG) to form a compound of Formula (10):

(10)
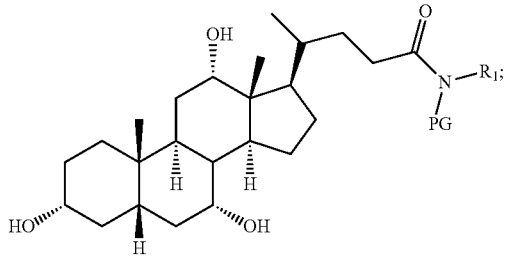

where $R_2$ is a hydrogen and is replaced with the amine protecting group;

(d1) reacting a compound of Formula (3) or Formula (4) with a compound of Formula (A)

(A)
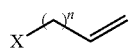

to form a compound of Formula (5a) or (5b):

(5a)
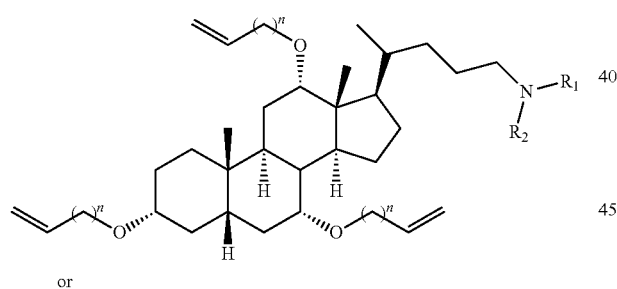

or (5b)
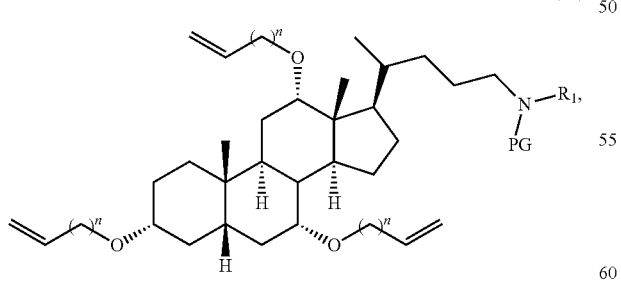

or (d2) reacting a compound of Formula (2) or Formula (10) with a compound of Formula (A) to form a compound of Formula (11a) or (11b):

(11a)

(11b)
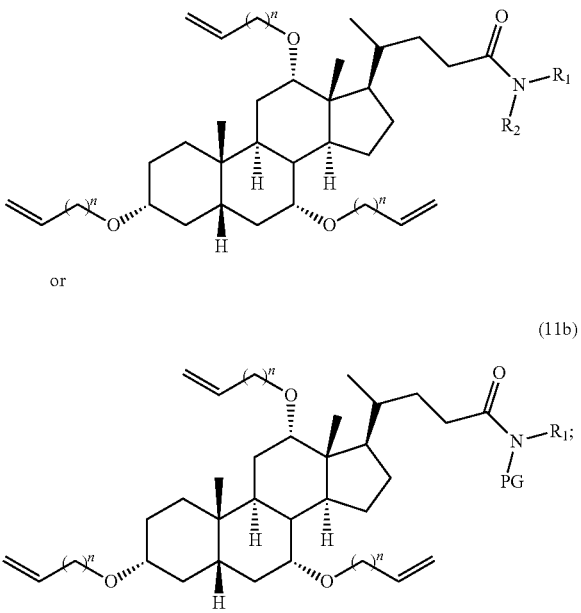

(e1) subjecting a compound of Formula (5a) or (5b) to hydroboration and oxidation conditions, followed by reaction with a compound of Formula (B)

$R_3$—$SO_2Cl$ (B)

to form a compound of Formula (6a) or (6b) having three terminal sulfonate groups:

(6a)
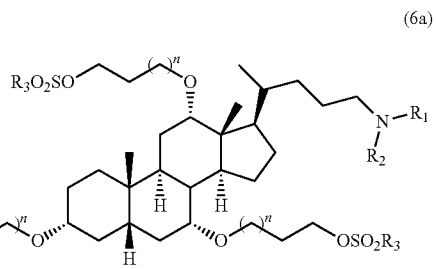

or (6b)
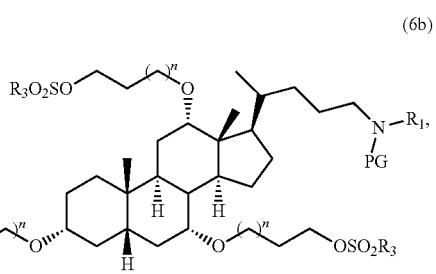

or (e2) subjecting a compound of Formula (11a) or (11b) to hydroboration and oxidation conditions, followed by reaction with a compound of Formula (B) to form a compound of Formula (12a) or (12b) having three terminal sulfonate groups:

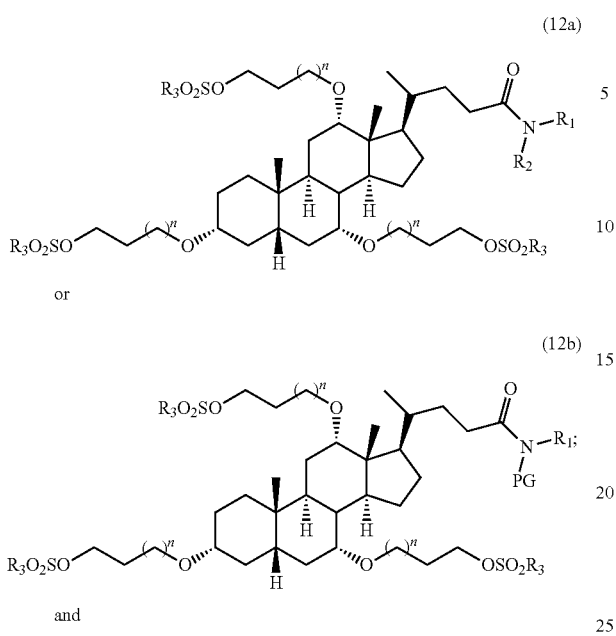

(12a)

(12b)

and (f1) reacting a compound of Formula (6a) or (6b) and $R_4R_5$—NH to thereby directly replace the three terminal sulfonate groups with amino groups, followed by optional deprotection to form a compound of Formula (I):

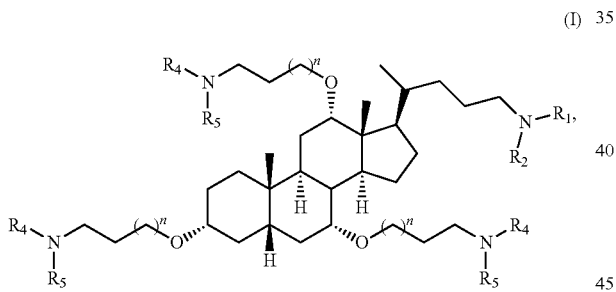

(I)

or (f2) reacting a compound of Formula (12a) or (12b) and $R_4R_5$—NH too thereby directly replace the three terminal sulfonate groups with amino groups, followed by optional deprotection to form a compound of Formula (III):

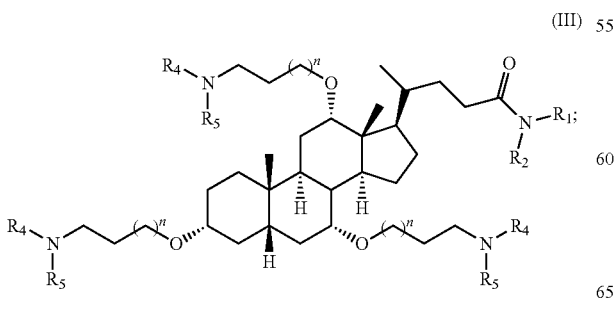

(III)

wherein:

X is independently selected from the group consisting of —F, —Cl, —Br, —I, tosylate, brosylate, nosylate, mesylate, and triflate;

n is an integer from 1 to 25;

$R_1$, $R_2$, $R_4$, and $R_5$ are independently selected from the group consisting of hydrogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, optionally substituted (5 to 10 membered heterocyclyl)-$C_1$-$C_6$ alkyl, an amine protecting group, and an optionally substituted amide;

$R_3$ is selected from the group consisting of optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted heterocyclyl, heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, optionally substituted amido, and optionally substituted (5 to 10 membered heterocyclyl)-$C_1$-$C_6$ alkyl, wherein if substituted, $R_1$, $R_2$, $R_3$, $R_4$ and/or $R_5$ include a substitution selected from the group consisting of $C_1$-$C_{24}$ alkyl, $C_1$-$C_{24}$ alkenyl, $C_1$-$C_{24}$ alkynyl, $C_1$-$C_{24}$ heteroalkyl, $C_3$-$C_{10}$ carbocyclyl, $C_3$-$C_{10}$-carbocyclyl-$C_1$-$C_6$-alkyl, heterocyclyl, heterocyclyl-$C_1$-$C_6$-alkyl, aryl, aryl($C_1$-$C_6$)alkyl, 5-10 membered heteroaryl, 5-10 membered heteroaryl($C_1$-$C_6$)alkyl, halo, cyano, hydroxy, $C_1$-$C_6$ alkoxy, $C_1$-$C_6$ alkoxy($C_1$-$C_6$)alkyl (i.e., ether), aryloxy, sulfhydryl (mercapto), halo($C_1$-$C_6$) alkyl, halo($C_1$-$C_6$)alkoxy, $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, amido, S-sulfonamido, N-sulfonamido, C-carboxy, O-carboxy, acyl, cyanato, isocyanato, thiocyanato, isothiocyanato, sulfinyl, sulfonyl, and oxo (=O), and wherein if one or more of $R_1$, $R_2$, $R_3$, $R_4$, or $R_5$ includes a heterocyclyl, the heterocyclyl is selected from the group consisting of azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

2. The method of claim 1, comprising the steps of:
(a) reacting a compound of Formula (1) and $R_1R_2$—NH

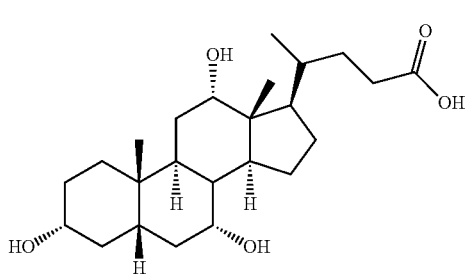
(1)

to form a compound of Formula (2):

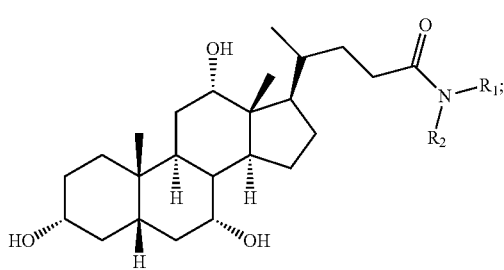
(2)

(b) optionally reducing a compound of Formula (2) to form a compound of Formula (3):

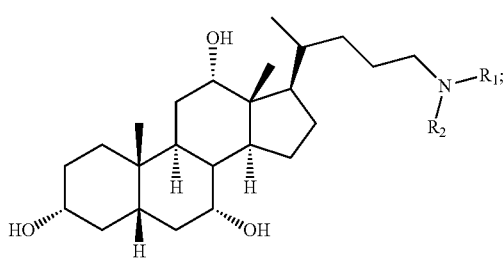
(3)

(c) optionally protecting a compound of Formula (3) with an amine protecting group to form a compound of Formula (4):

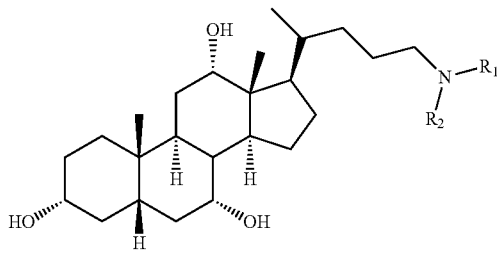
(4)

wherein $R_2$ is a hydrogen and is replaced with the amine protecting group;

(d) reacting a compound of Formula (3) or Formula (4) with a compound of Formula (A)

(A)

to form a compound of Formula (5a) or (5b):

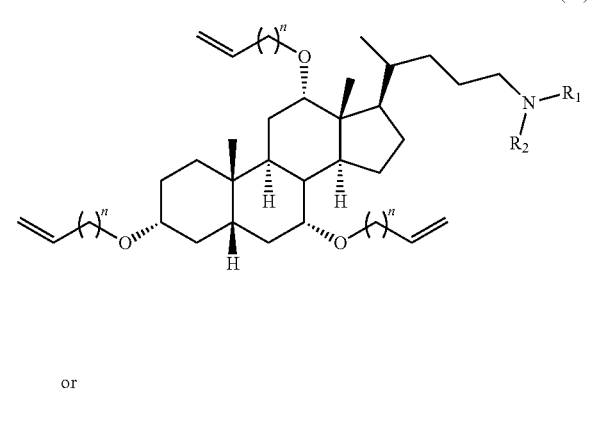
(5a)

or (5b)

(e) subjecting a compound of Formula (5a) or (5b) to hydroboration and oxidation conditions, followed by reaction with a compound of Formula (B)

$R_3$—$SO_2Cl$ (B)

to form a compound of Formula (6a) or (6b):

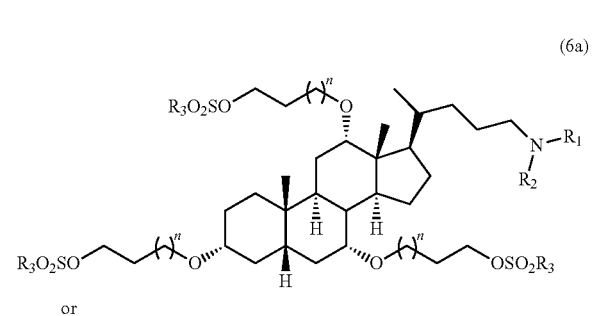
(6a)

or

-continued (6b)

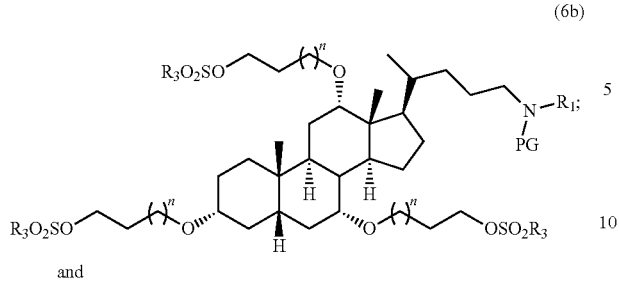

and (f) reacting a compound of Formula (6a) or (6b) and R₄R₅—NH, followed by optional deprotection to form a compound of Formula (I):

(I)

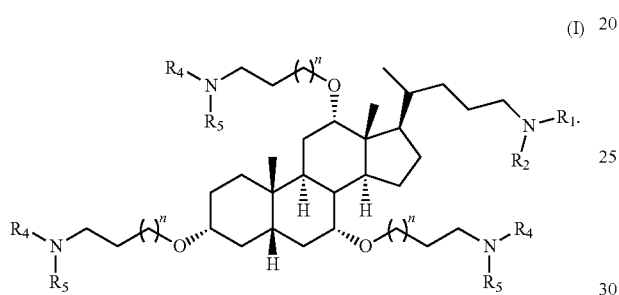

3. The method of claim 1, comprising the steps of:
(a) reacting a compound of Formula (1) and $R_1R_2$—NH (1)

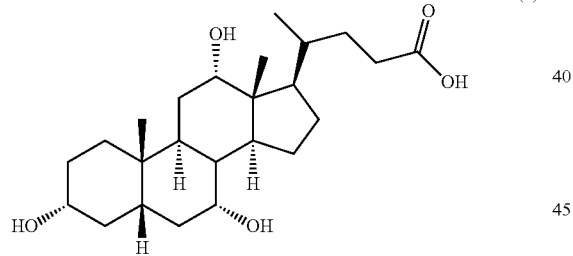

to form a compound of Formula (2):

(2)

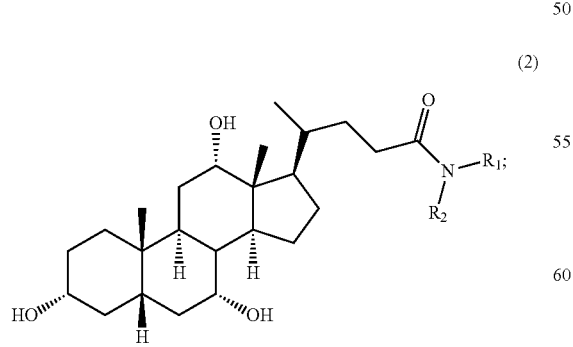

(b) optionally protecting a compound of Formula (2) with an amine protecting group to form a compound of Formula (10):

(10)

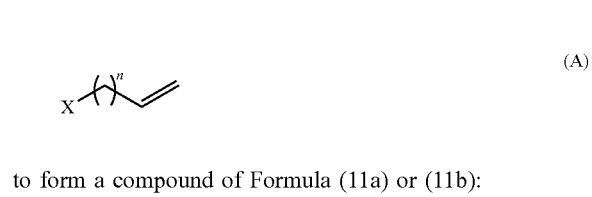

wherein $R_2$ is a hydrogen and is replaced with the amine protecting group;

(c) reacting a compound of Formula (2) or Formula (10) with a compound of Formula (A)

(A)

$$X\!-\!\!\overset{n}{(\phantom{x})}\!\!-\!\!=$$

to form a compound of Formula (11a) or (11b):

(11a)

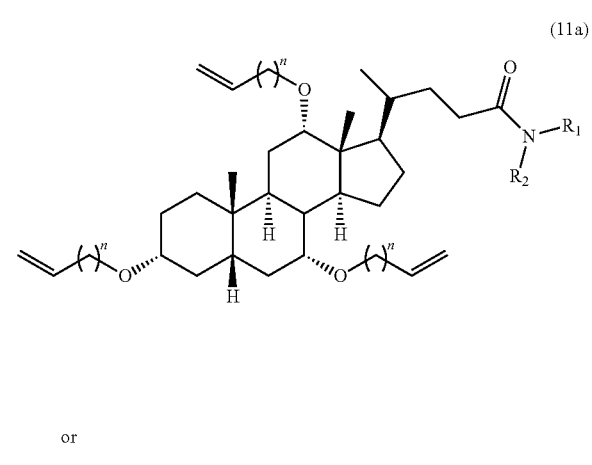

or (11b)

(d) subjecting a compound of Formula (11a) or (11b) to hydroboration and oxidation conditions, followed by reaction with a compound of Formula (B)

$R_3$—$SO_2Cl$ (B)

to form a compound of Formula (12a) or (12b):

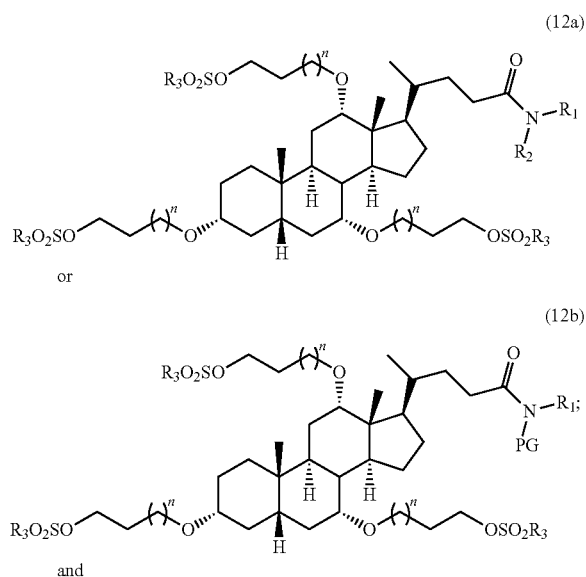

and (e) reacting a compound of Formula (12a) or (12b) and R₄R₅—NH, followed by optional deprotection to form a compound of Formula (III):

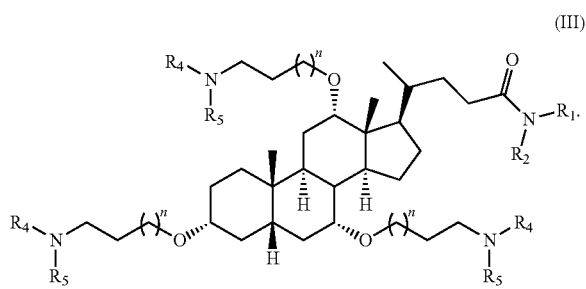

4. The method of claim 1, wherein:
R₁ and R₂, together with the atoms to which they are attached form an optionally substituted 5 to 10 membered heterocyclyl ring; and
R₄ and R₅, together with the atoms to which they are attached form an optionally substituted 5 to 10 membered heterocyclyl ring.

5. The method of claim 1, wherein R₂ is hydrogen and R₁ is selected from the group consisting of hydrogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, optionally substituted (5 to 10 membered heterocyclyl)-$C_1$-$C_6$ alkyl, an amine protecting group, and an optionally substituted amide.

6. The method of claim 1, wherein R₂ is hydrogen and R₁ is selected from the group consisting of optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, an optionally substituted amide, and optionally substituted (5 to 10 membered heterocyclyl)-$C_1$-$C_6$ alkyl.

7. The method of claim 1, wherein R₂ is hydrogen and R₁ is optionally substituted $C_1$-$C_{24}$ alkyl.

8. The method of claim 1, wherein n is 1 or 2.

9. The method of claim 1, wherein R₄ is hydrogen and R₅ is selected from the group consisting of hydrogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, optionally substituted (5 to 10 membered heterocyclyl)-$C_1$-$C_6$ alkyl, and an amine protecting group.

10. The method of claim 1, wherein R₄ is hydrogen and R₅ is selected from the group consisting of hydrogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, and optionally substituted (5 to 10 membered heterocyclyl)-$C_1$-$C_6$ alkyl.

11. The method of claim 1, wherein R₄ is hydrogen and R₅ is hydrogen or optionally substituted $C_1$-$C_{24}$ alkyl.

12. The method of claim 1, wherein R₄ and R₅ are both hydrogen.

13. The method of claim 1, wherein the compound of Formula (I) or the compound of Formula (III) is selected from the group consisting of:

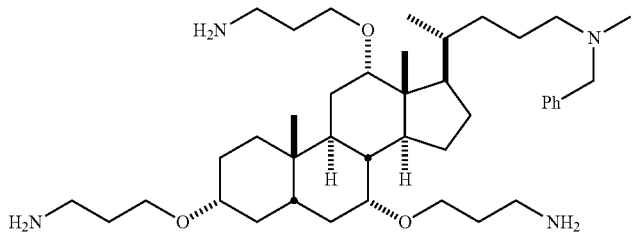

-continued
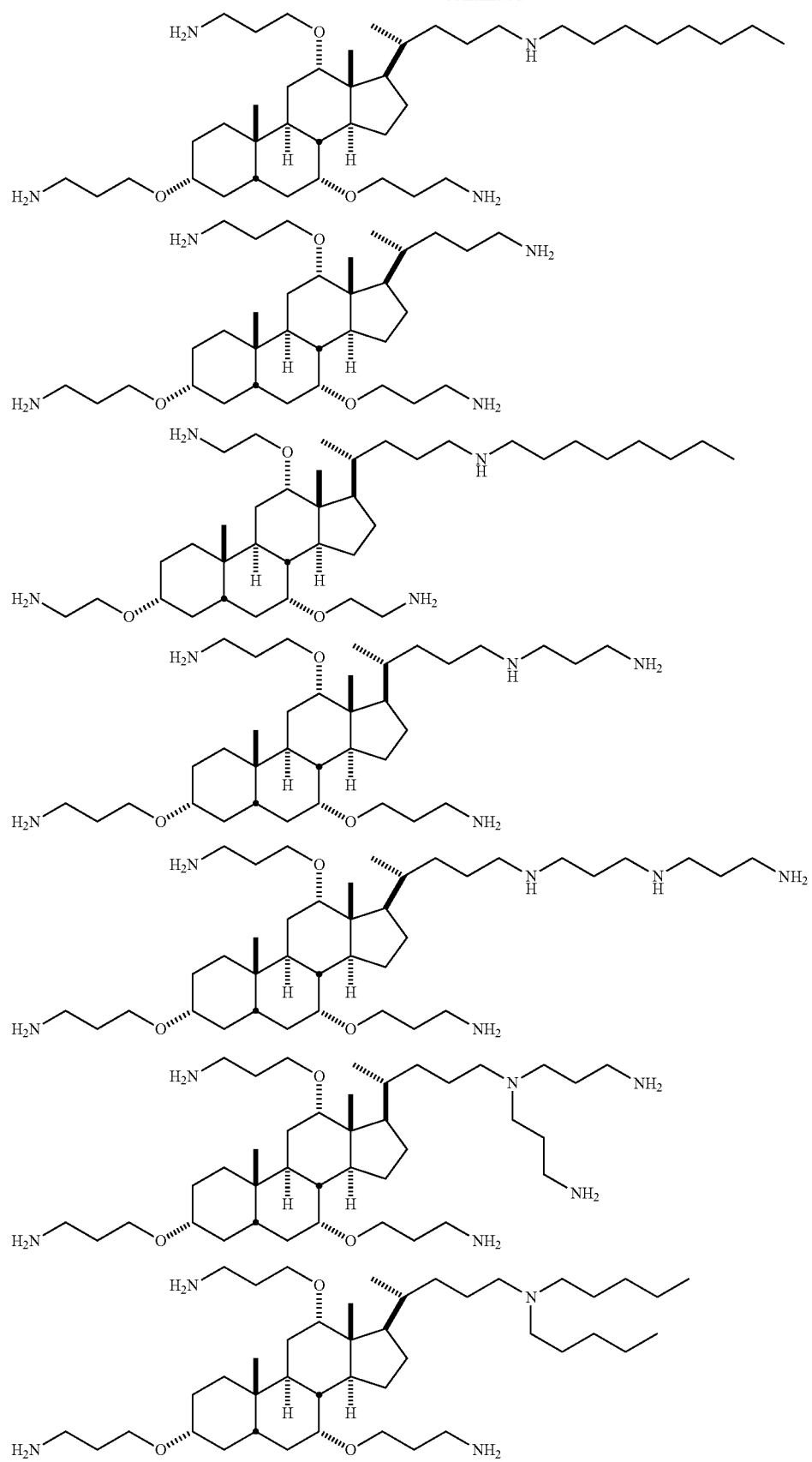

-continued
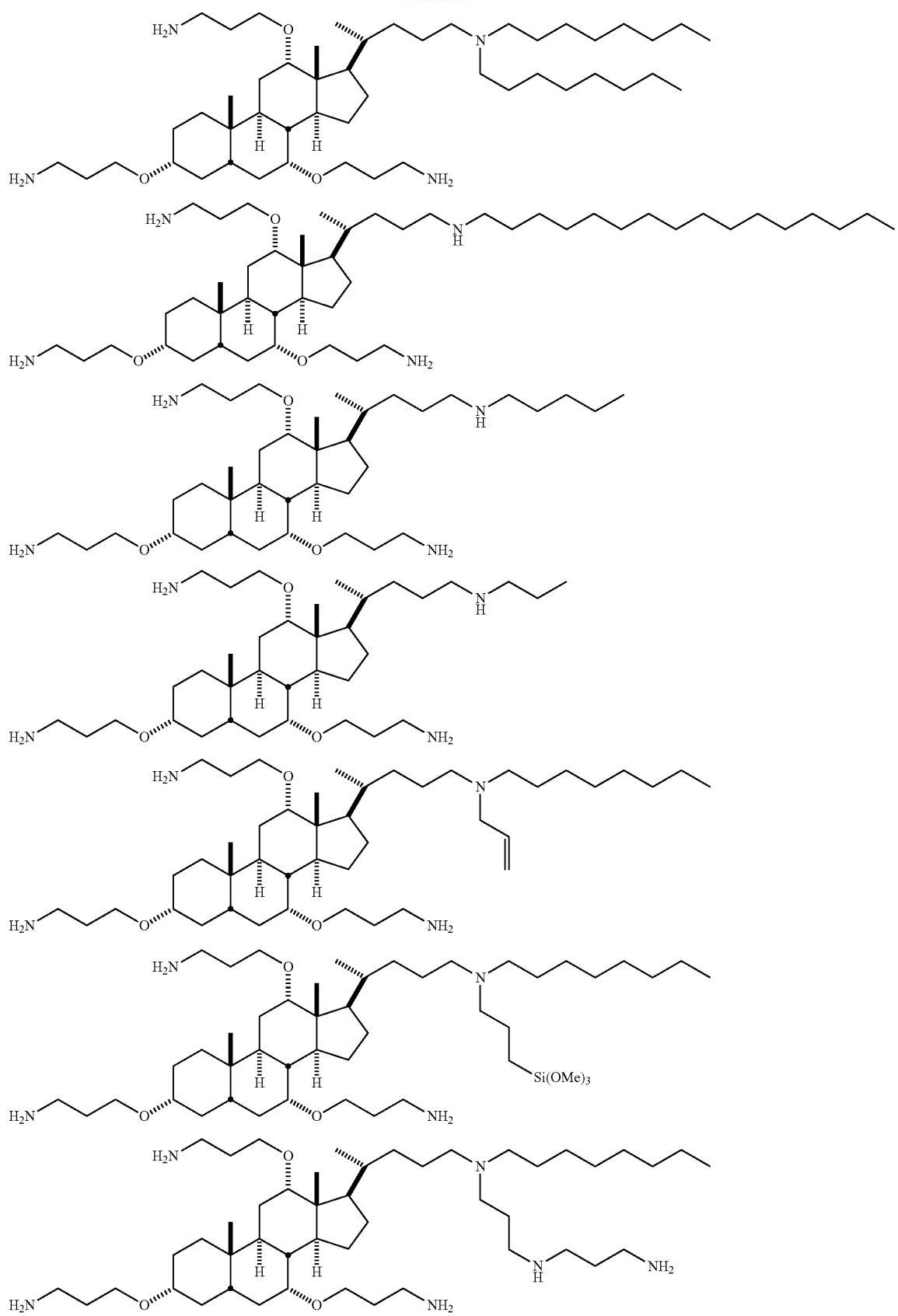

-continued
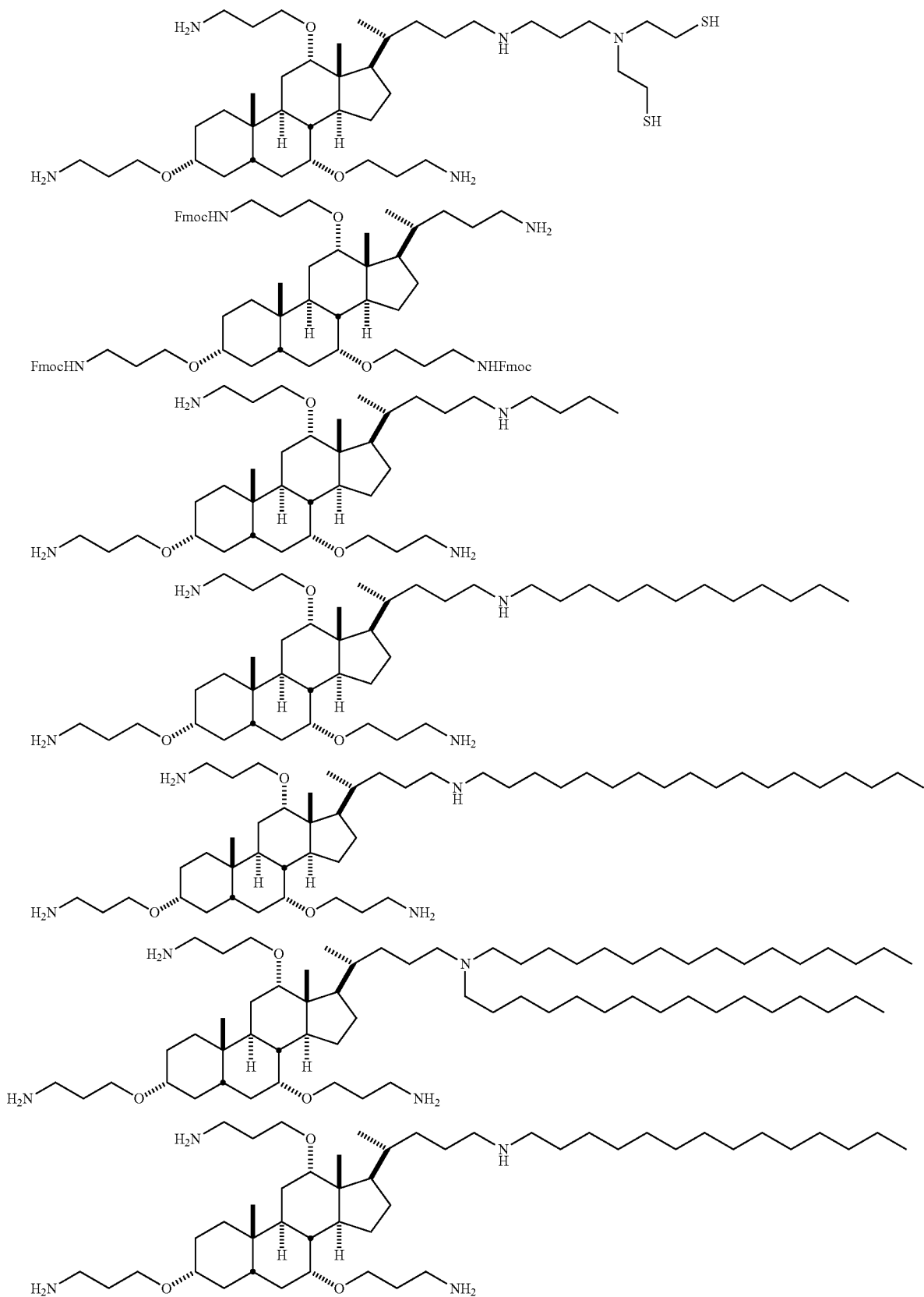

-continued
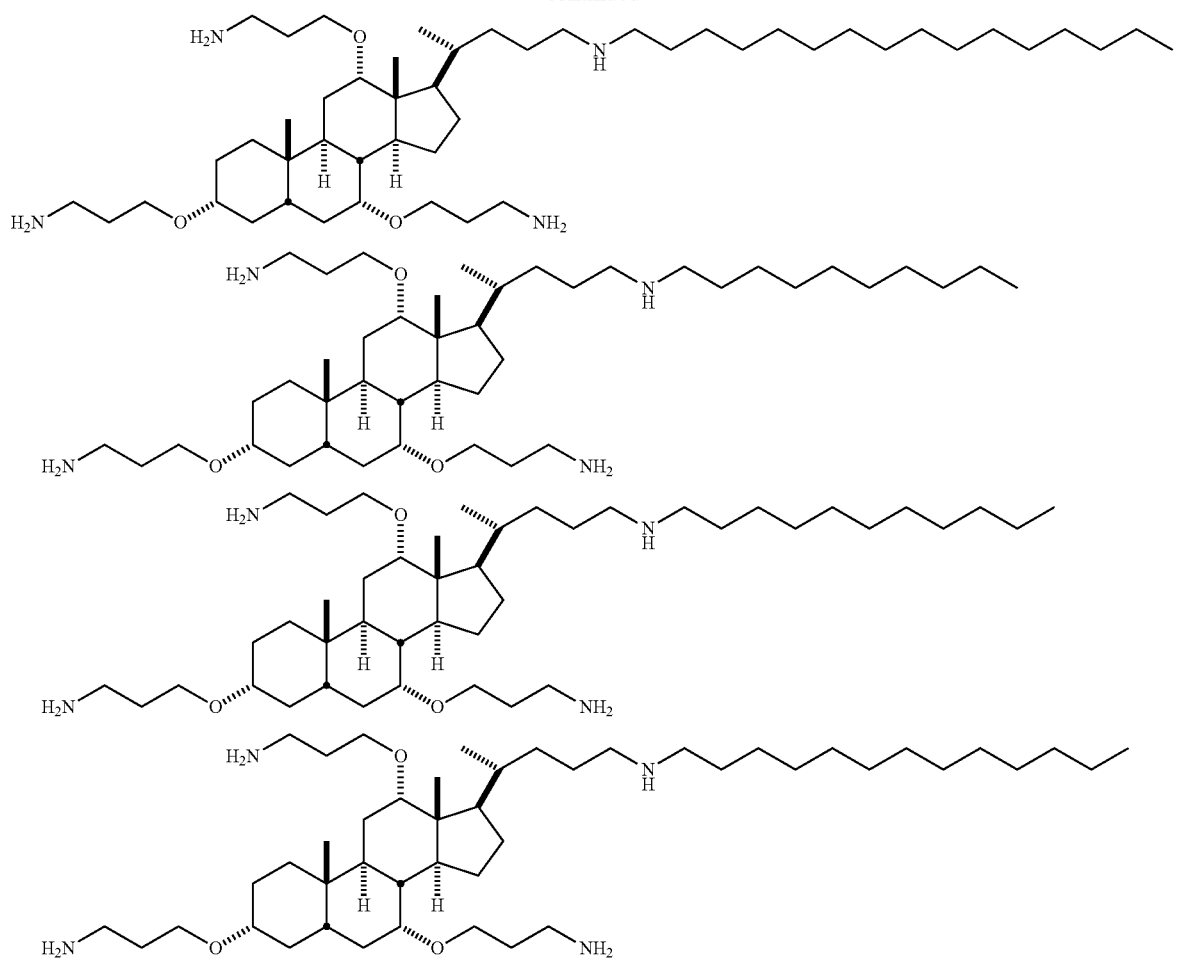
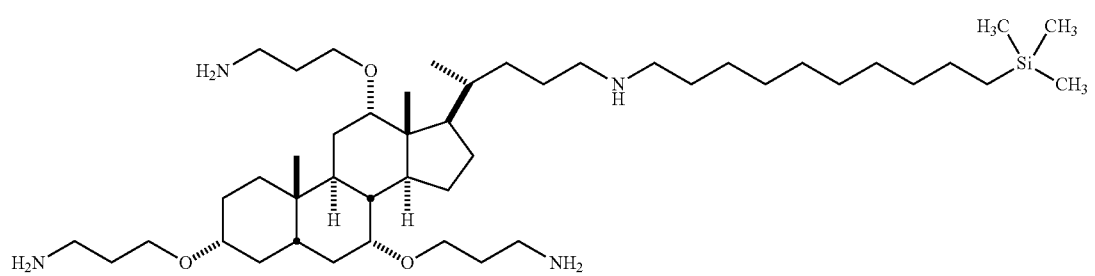
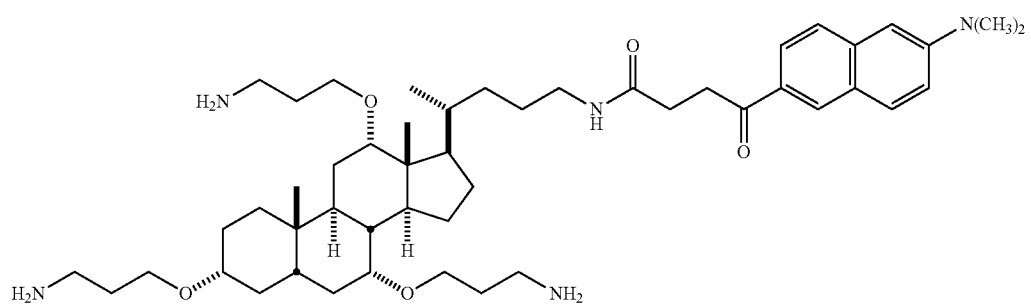

-continued

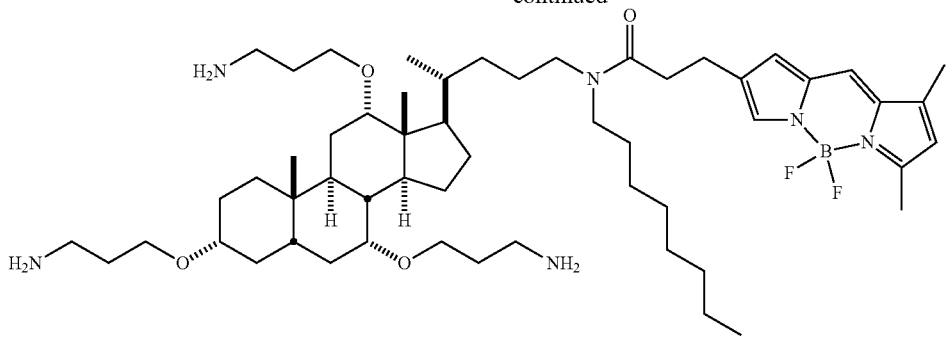

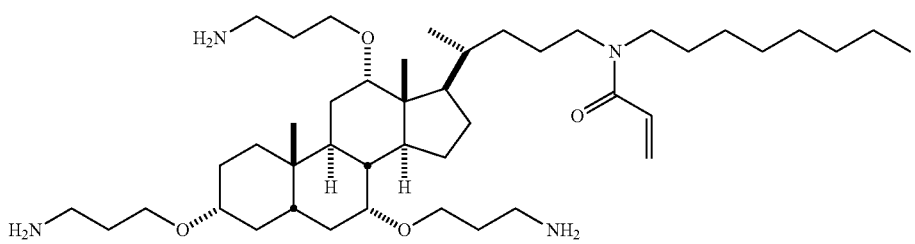

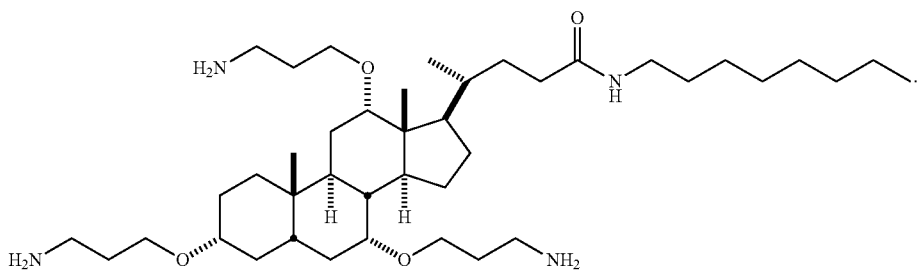

14. The method of claim 1, wherein one or more steps of the method is carried out in one or more solvents selected from the group consisting of water, acetic acid, formic acid, hydrochloric acid, hydrobromic acid, DMF, DMSO, DCM, NMP, chloroform, THF, 2-methyl-THF, benzene, toluene, trifluorotoluene, dioxane, methanol, ethanol, ethyl acetate, acetone, or any combination thereof.

15. The method of claim 1, wherein one or more steps of the method is carried out at a temperature of at least 10° C.

16. The method of claim 1, wherein the method is accomplished in less than 25 hours.

17. The method of claim 1, wherein the method provides at least one kilogram of a compound of Formula (I) or a Formula (III).

18. The method of claim 1, wherein at least part of the method is performed at ambient pressure.

19. The method of claim 1, wherein the method does not deliberately exclude the presence of oxygen.

20. The method of claim 1, wherein at least part of the method is performed in a non-oxygen-containing atmosphere.

21. The method of claim 1, wherein one or more steps of the method is performed with a mixing rate of at least 50 rpms.

22. A method of making a compound of Formula (I), comprising the steps of:

(a) reacting a compound of Formula (1) and $R_1R_2$—NH

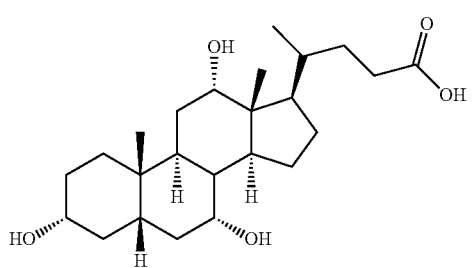

(1)

to form a compound of Formula (2):

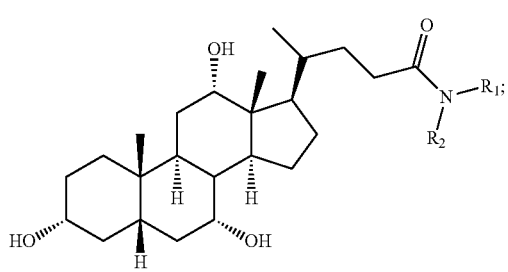

(2)

(b) reducing a compound of Formula (2) to form a compound of Formula (3):

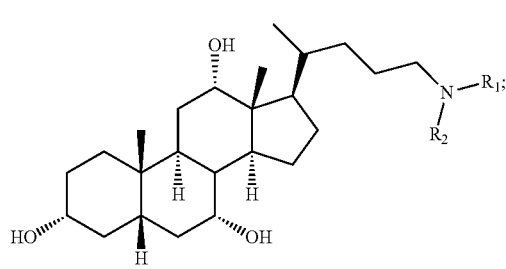
(3)

(c) protecting the compound of Formula (3) with an amine protecting group (PG) to form a compound of Formula (4):

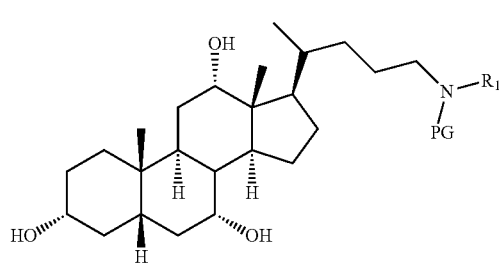
(4)

where $R_2$ is a hydrogen and is replaced with the amine protecting group, (d) reacting the compound of Formula (4) with a compound of Formula (A)

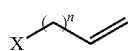
(A)

to form a compound of Formula (5):

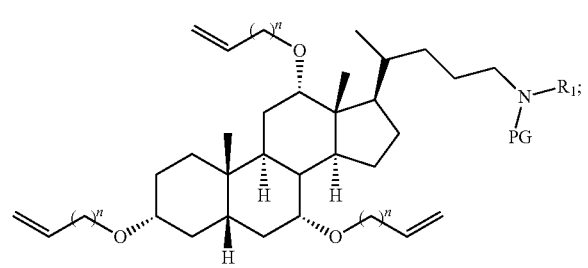
(5)

(e) subjecting the compound of Formula (5) to hydroboration and oxidation conditions, followed by reaction with a compound of Formula (B)

(B)

to form a compound of Formula (6) having three terminal sulfonate groups:

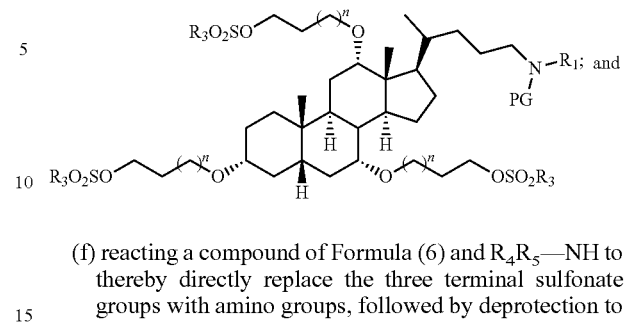
(6)

(f) reacting a compound of Formula (6) and $R_4R_5$—NH to thereby directly replace the three terminal sulfonate groups with amino groups, followed by deprotection to form a compound of Formula (I):

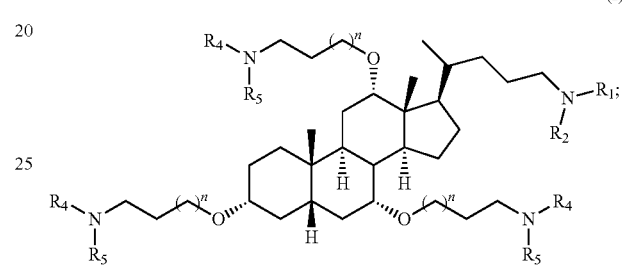
(I)

wherein:
X is independently selected from the group consisting of —F, —Cl, —Br, —I, tosylate, brosylate, nosylate, mesylate, and triflate;
n is an integer from 1 to 25;
$R_1$, $R_2$, $R_4$, and $R_5$ are independently selected from the group consisting of hydrogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, optionally substituted (5 to 10 membered heterocyclyl)-$C_1$-$C_6$ alkyl, an amine protecting group, and an optionally substituted amide; and
$R_3$ is selected from the group consisting of optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, optionally substituted amido, and optionally substituted (5 to 10 membered heterocyclyl)-$C_1$-$C_6$ alkyl,
wherein if substituted, $R_1$, $R_2$, $R_3$, $R_4$ and/or $R_5$ include a substitution selected from the group consisting of $C_1$-$C_{24}$ alkyl, $C_1$-$C_{24}$ alkenyl, $C_1$-$C_{24}$ alkynyl, $C_1$-$C_{24}$ heteroalkyl, $C_3$-$C_{10}$ carbocyclyl, $C_3$-$C_{10}$-carbocyclyl-$C_1$-$C_6$-alkyl, heterocyclyl, heterocyclyl-$C_1$-$C_6$-alkyl, aryl, aryl($C_1$-$C_6$)alkyl, 5-10 membered heteroaryl, 5-10 membered heteroaryl($C_1$-$C_6$)alkyl, halo, cyano, hydroxy, $C_1$-$C_6$ alkoxy, $C_1$-$C_6$ alkoxy($C_1$-$C_6$)alkyl (i.e., ether), aryloxy, sulfhydryl (mercapto), halo($C_1$-$C_6$) alkyl, halo($C_1$-$C_6$)alkoxy, $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, amido, S-sulfonamido, N-sulfonamido, C-carboxy, O-carboxy, acyl, cyanato, isocyanato, thiocyanato, isothiocyanato, sulfinyl, sulfonyl, and oxo (=O), and wherein if one or more of $R_1$, $R_2$, $R_3$, $R_4$, or $R_5$ includes a heterocyclyl, the heterocyclyl is selected from the group consisting of azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazol idinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

23. The method of claim 22, wherein the method provides at least one kilogram of the compound of Formula (I).

24. The method of claim 22, wherein at least part of the method is performed in a non-oxygen-containing atmosphere.

25. A method of making a compound of Formula (III), comprising the steps of:
(a) reacting a compound of Formula (1) and $R_1R_2$—NH (1)

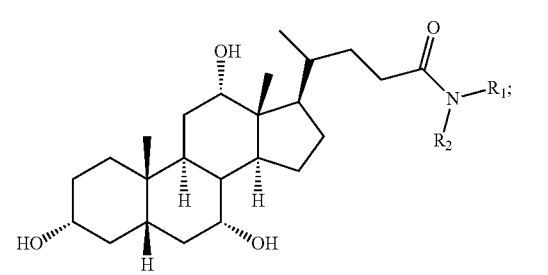

to form a compound of Formula (2):

(2)

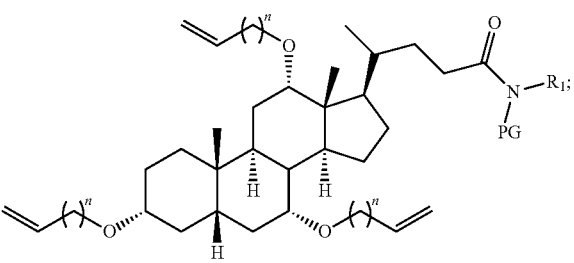

(b) optionally protecting a compound of Formula (2) with an amine protecting group (PG) to form a compound of Formula (10):

(10)

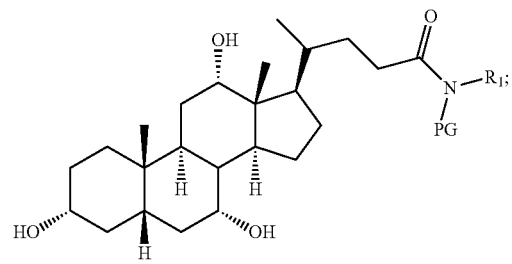

where $R_2$ is a hydrogen and is replaced with the amine protecting group;

(c) reacting a compound of Formula (2) or Formula (10) with a compound of Formula (A) to form a compound of Formula (11a) or (11b):

(11a)

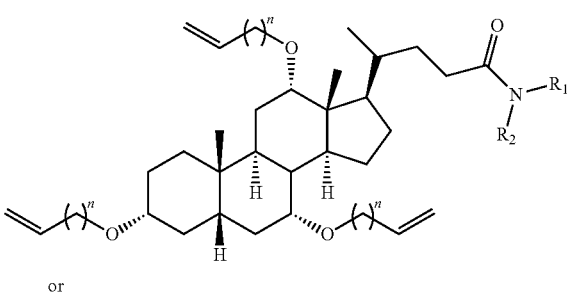

or (11b)

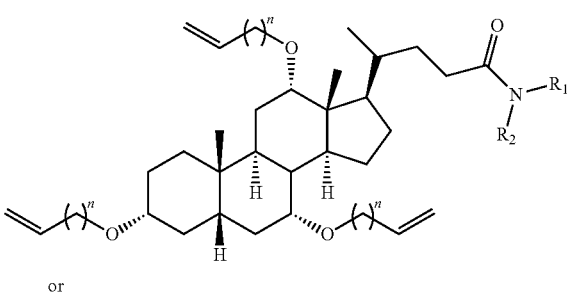

(d) subjecting a compound of Formula (11a) or (11b) to hydroboration and oxidation conditions, followed by reaction with a compound of Formula (B) to form a compound of Formula (12a) or (12b) having three terminal sulfonate groups:

(12a)

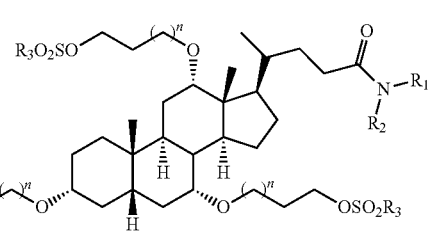

or

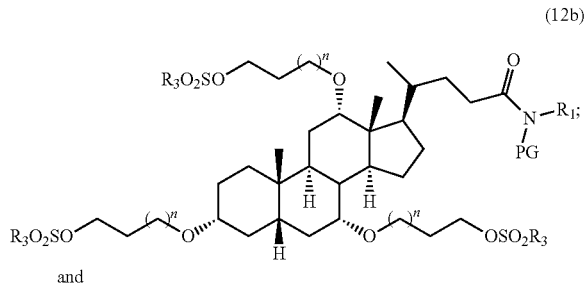

(12b)

and (e) reacting a compound of Formula (12a) or (12b) and $R_4R_5$—NH to thereby directly replace the tree terminal sulfonate groups with amino groups, followed by optional deprotection to form a compound of Formula (III):

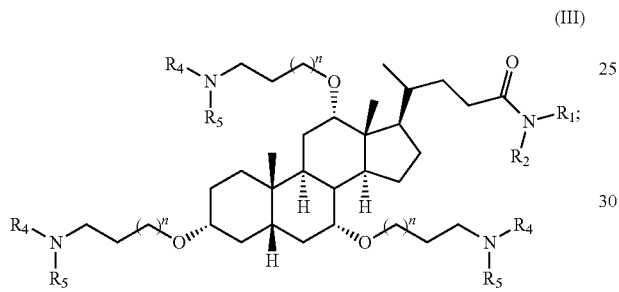

(III)

wherein:
X is independently selected from the group consisting of —F, —Cl, —Br, —I, tosylate, brosylate, nosylate, mesylate, and triflate;
n is an integer from 1 to 25;
$R_1$, $R_2$, $R_4$, and $R_5$ are independently selected from the group consisting of hydrogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, optionally substituted (5 to 10 membered heterocyclyl)-$C_1$-$C_6$ alkyl, an amine protecting group, and an optionally substituted amide; and $R_3$ is selected from the group consisting of optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, optionally substituted amido, and optionally substituted (5 to 10 membered heterocyclyl)-$C_1$-$C_6$ alkyl wherein if substituted, $R_1$, $R_2$, $R_3$, $R_4$ and/or $R_5$ include a substitution selected from the group consisting of $C_1$-$C_{14}$ alkyl, $C_1$-$C_{24}$ alkenyl, $C_1$-$C_{24}$ alkynyl, $C_1$-$C_{24}$ heteroalkyl, $C_3$-$C_{10}$ carbocyclyl, $C_3$-$C_{10}$-carbocyclyl-$C_1$-$C_6$-alkyl, heterocyclyl, heterocyclyl-$C_1$-$C_6$-alkyl, aryl, aryl($C_1$-$C_6$)alkyl, 5-10 membered heteroaryl, 5-10 membered heteroaryl($C_1$-$C_6$)alkyl, halo, cyano, hydroxy, $C_1$-$C_6$ alkoxy, $C_1$-$C_6$ alkoxy($C_1$-$C_6$)alkyl (i.e., ether), aryloxy, sulfhydryl (mercapto), halo($C_1$-$C_6$) alkyl, halo($C_1$-$C_6$)alkoxy, $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, amido, S-sulfonamido, N-sulfonamido, C-carboxy, O-carboxy, acyl, cyanato, isocyanato, thiocyanato, isothiocyanato, sulfinyl, sulfonyl, and oxo (=O), and wherein if one or more of $R_1$, $R_2$, $R_3$, $R_4$, or $R_5$ includes a heterocyclyl, the heterocyclyl is selected from the group consisting of azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazol idinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

26. The method of claim 24, wherein the method provides at least one kilogram of the compound of Formula (III).

27. The method of claim 24, wherein at least part of the method is performed in a non-oxygen-containing atmosphere.

* * * * *